US012590063B2

(12) United States Patent
Yoshida et al.

(10) Patent No.: US 12,590,063 B2
(45) Date of Patent: Mar. 31, 2026

(54) PHENOL DERIVATIVE

(71) Applicant: Sumitomo Pharma Co., Ltd., Osaka (JP)

(72) Inventors: Kozo Yoshida, Osaka (JP); Hiroyuki Kitano, Osaka (JP); Yuki Mizukami, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 465 days.

(21) Appl. No.: 18/043,864

(22) PCT Filed: Sep. 3, 2021

(86) PCT No.: PCT/JP2021/032483
§ 371 (c)(1),
(2) Date: Mar. 2, 2023

(87) PCT Pub. No.: WO2022/050385
PCT Pub. Date: Mar. 10, 2022

(65) Prior Publication Data
US 2023/0312474 A1 Oct. 5, 2023

(30) Foreign Application Priority Data
Sep. 7, 2020 (JP) ................................. 2020-149973

(51) Int. Cl.
*C07D 213/75* (2006.01)
*A61P 1/06* (2006.01)
(Continued)

(52) U.S. Cl.
CPC .............. *C07D 213/75* (2013.01); *A61P 1/06* (2018.01); *C07C 233/29* (2013.01);
(Continued)

(58) Field of Classification Search
None
See application file for complete search history.

(56) References Cited

U.S. PATENT DOCUMENTS

| | | | | |
|---|---|---|---|---|
| 2011/0288280 | A1 | 11/2011 | Hosoya et al. | |
| 2017/0057982 | A1* | 3/2017 | Yang | A61P 29/00 |
| 2021/0206718 | A1* | 7/2021 | Li | C07D 231/12 |

FOREIGN PATENT DOCUMENTS

| | | | |
|---|---|---|---|
| GB | 2 276 161 | A | 9/1994 |
| GB | 2 276 163 | A | 9/1994 |

(Continued)

OTHER PUBLICATIONS

Tomsen, Noemi et al. "Acute and subacute effects of oropharyngeal sensory stimulation with TRPV1 agonists in older patients with oropharyngeal dysphagia: a biomechanical and neurophysiological randomized pilot study," Therapeutic Advances in Gastroenterology, vol. 12, 2019, pp. 1-13.

(Continued)

*Primary Examiner* — Bethany P Barham
(74) *Attorney, Agent, or Firm* — Oblon, McClelland, Maier & Neustadt, L.L.P.

(57) ABSTRACT

A compound represented by formula (2) or pharmaceutically acceptable salt thereof:

[Chemical Formula 1]

(2)

(Continued)

wherein $R^1$ represents a hydrogen atom or the like; $R^2$ represents a methoxy group or the like; $R^3$ represents a hydrogen atom or the like; $R^4$ represents an optionally substituted $C_{1-6}$ alkyl group or the like; m represents 0, 1, or 2; n represents 0, 1, 2, or 3; $L^1$ represents —NH—C(═O)—, —C(═O)—NH—, or the like; $L^2$ represents a single bond or the like; X represents optionally substituted phenyl or the like; Y represents optionally substituted phenyl or the like; and X and Y are bonded at a carbon atom on each ring.

27 Claims, 1 Drawing Sheet

(51) Int. Cl.

*C07C 233/29* (2006.01)
*C07C 233/73* (2006.01)
*C07D 309/06* (2006.01)
*C07D 333/24* (2006.01)

(52) U.S. Cl.

CPC .......... *C07C 233/73* (2013.01); *C07D 309/06* (2013.01); *C07D 333/24* (2013.01)

(56) References Cited

FOREIGN PATENT DOCUMENTS

| | | | | |
|---|---|---|---|---|
| JP | 2004-339061 A | | 12/2004 | |
| JP | 2006-205708 A | | 8/2006 | |
| JP | 2007-509915 A | | 4/2007 | |
| JP | 2008-539253 A | | 11/2008 | |
| JP | 2011-500839 A | | 1/2011 | |
| JP | 2013-125180 A | | 6/2013 | |
| WO | WO 02/100819 A1 | | 12/2002 | |
| WO | WO 03/055848 A2 | | 7/2003 | |
| WO | WO 2005/051390 A1 | | 6/2005 | |
| WO | WO 2006/115168 A1 | | 11/2006 | |
| WO | WO 2006/116485 A2 | | 11/2006 | |
| WO | WO 2008/136378 A1 | | 11/2008 | |
| WO | WO 2009/055629 A2 | | 4/2009 | |
| WO | WO 2009/136625 A1 | | 11/2009 | |
| WO | WO 2010/090318 A1 | | 8/2010 | |
| WO | WO 2011/058932 A1 | | 5/2011 | |
| WO | WO 2011/058933 A1 | | 5/2011 | |
| WO | WO-2021068951 A1 | * | 4/2021 | ................ A61P 9/00 |
| WO | WO-2021094974 A1 | * | 5/2021 | ........... C07D 471/08 |

OTHER PUBLICATIONS

International Preliminary Report on Patentability and Written Opinion issued Mar. 16, 2023, in PCT/JP2021/032483, 6 pages.
International Search Report issued Nov. 2, 2021 in PCT/JP2021/032483, filed on Sep. 3, 2021, 3 pages.
Nakazawa, H. et al., "Risk of Aspiration Pneumonia in the Elderly", Chest, 1993, vol. 103, pp. 1636-1637.
Sekizawa, K. et al., "Lack of cough reflex in aspiration pneumonia", LANCET, 1990, vol. 355, pp. 1228-1229.
Nakayama, K. et al., "ACE Inhibitor and Swallowing Reflex", Chest, 1998, vol. 113, No. 5, p. 1425.
Funahashi, H. et al., "Four Cases of Ischemic Cerebral Infarction in the Chronic Stage with Aspiration Pneumonia Teated with Cilostazol", Kyusyu Neuropsychiatry, 2012, vol. 58, No. 1, pp. 14-21 (with Machine Generated Translation), 19 total pages.
Nakashima, T. et al., "Nicergoline Improves Dysphagia by Upregulating Substance P in the Elderly", Medicine, 2011, vol. 90, No. 4, pp. 279-283.
Iwasaki, K. et al., "The Traditional Chinese Medicine Banxia Houpo Tang improves swallowing reflex", Phytomedicine, 1999, vol. 6, No. 2, pp. 103-106.
Ebihara, T. et al., "Capsaicin and swallowing reflex", LANCET, 1993, vol. 341, p. 432.
Fosgerau, K. et al., "Drug-induced mild therapeutic hypothermia obtained by administration of a transient receptor potential vanilloid Type 1 agonist", BMC Cardiovascular Disorders, 2010, vol. 10, pp. 51-60.
Caterina, M. et al., "The capsaicin receptor: a heat-activated ion channel in the pain pathway", Nature, 1997, vol. 389, pp. 816-824.
Sharma, Padam N. et al., "Reaction of Alcohols and Amines with Diacetyldihydrofluorescein (DADF): Conversion into Erythrosinederivatives on TLC-Plates by Ammonia and Iodine Vapors", Helvetica Chimica Acta, 1984, vol. 67, No. 1, pp. 301-304.
Ranjith, Jala et al., "Intramolecular oxyacetoxylation of Nallylamides: an expeditious synthesis of oxazolines and oxazines by using a Phl(OAc)2/hydrogen fluoride-pyridine system", Organic & Biomolecular Chemistry, 2016, vol. 14, No. 42, pp. 10074-10079 (8 total pages).
Ganesh, Thota et al., "Synthesis and SAR study of N-(4-hydroxy-3-(2-hydroxynaphthalene-1-yl)phenyl)-arylsulfonamides: Heat shock protein 90 (Hsp90) inhibitors with submicromolar activity in an in vitro assay", Bioorganic & Medicinal Chemistry Letters, 2008, vol. 18, No. 18, pp. 4982-4987.
Zhang, Yun Zhi et al., "C-Glycosyl Amino-Substituted Hydro- and Benzoquinones: Synthesis and Preliminary Biological Evaluation", Synthesis, 2007, No. 22, pp. 3473-3488 (18 total pages).
"Registry STN [online], Sep. 2, 2020, Sep. 10, 2015, Jun. 5, 2002, [retrieved on Oct. 8, 2021], CAS registration Nos. 2470155-09-8, 1805003-26-2, 425629-78-3" (3 pages).

* cited by examiner

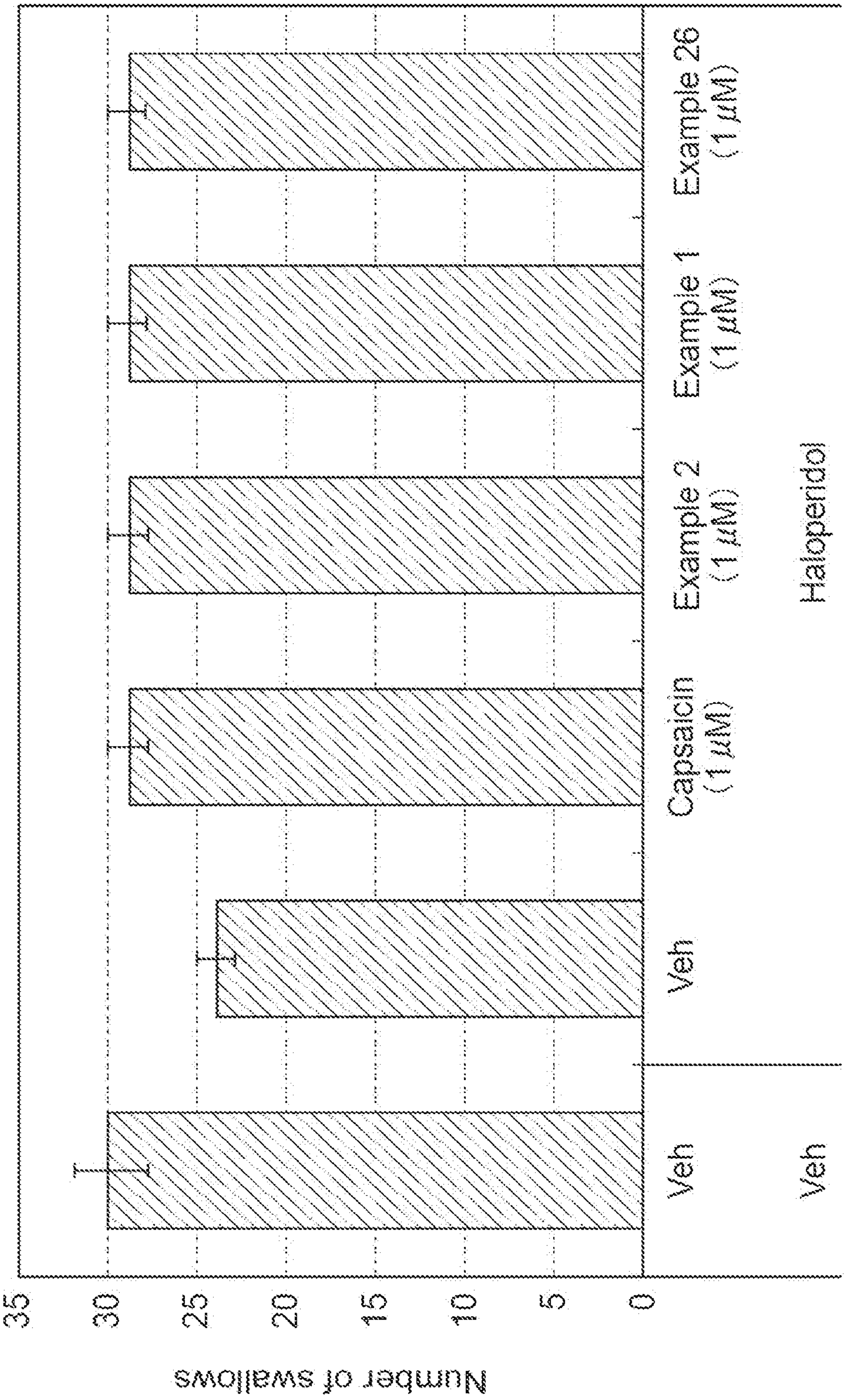
Number of swallows
0
5
10
15
20
25
30
35
Veh
Veh
Veh
Capsaicin (1 μM)
Example 2 (1 μM)
Example 1 (1 μM)
Example 26 (1 μM)
Haloperidol

PHENOL DERIVATIVE

CROSS-REFERENCE TO RELATED APPLICATIONS

The present application is a 35 U.S.C. § 371 national stage patent application of International patent application PCT/JP2021/032483, filed on Sep. 3, 2021, which is based on and claims the benefits of priority to Japanese Application No. 2020-149973, filed on Sep. 7, 2020. The entire contents of these applications are incorporated herein by reference.

TECHNICAL FIELD

The present invention relates to a phenol derivative and a pharmaceutically acceptable salt thereof useful as a medicament, and to a pharmaceutical composition comprising them as an active ingredient, or a therapeutic drug for dysphagia that can improve the swallowing reflex.

BACKGROUND ART

The swallowing action is composed of five phases: the preceding phase of recognizing food; the preparatory phase of intaking the food into the mouth and chewing it; the oral phase of sending the food into the pharynx with the tongue; the pharyngeal phase in which the swallowing reflex is induced by the stimulation of the food to send the food into the esophagus; and the esophageal phase of delivering the food from the esophagus to the stomach by peristaltic movement. When failure occurs in any of these movements, smooth swallowing action does not take place, resulting in dysphagia. Abnormalities or decreases in the swallowing reflex during the pharyngeal phase are brought about by various agents, cerebrovascular diseases and neurodegenerative diseases, and also by aging (Non Patent Literatures 1 and 2).

As treatment methods for dysphagia, swallowing instruction, rehabilitation, and surgical treatments are carried out. For delaying the swallowing reflex, it is recommended to select a food form with high viscosity. In rehabilitation, thermal-tactile stimulation is used as a method for eliciting the swallowing reflex, and stretching of the swallowing-related organs and swallowing pattern training are carried out. The efficacy of each of the above has not been well verified through randomized controlled trials, and further investigation is still needed to determine the effectiveness. When the above methods are not successful, surgery to improve swallowing function is considered, but it should be performed with caution because it is invasive and may not have the desired effect. Accordingly, there is a need for a therapeutic method that can clearly demonstrate effectiveness for dysphagia.

Agents that have been reported to have an improving effect on the swallowing reflex include an angiotensin converting enzyme (ACE) inhibitor (Non Patent Literature 3), cilostazol (Non Patent Literature 4), nicergoline (Non Patent Literature 5), and hangekobokuto (Non Patent Literature 6). These agents raise the amount of substance P released in the periphery and are thus likely to elicit the swallowing reflex, and as a result, are expected to be effective in preventing pneumonia, but their effectiveness is uncertain. Therefore, the creation of a therapeutic drug for dysphagia is desired.

In the meantime, ingredients that are used as supplements, such as capsaicin, black pepper, and menthol, have also been reported to improve the swallowing reflex. They act on transient receptor potential (TRP) channels and thus release substance P. Among them, capsaicin, as a TRPV1 agonist, has been reported to strongly improve the swallowing reflex (Non Patent Literature 7), and supplements that are expected to have an improving effect on swallowing are also on the market. However, it is not widely used because it is not a pharmaceutical product or for other reasons.

Compounds described in Patent Literatures 1 to 5, for example, are disclosed as TRPV1 agonists, but they are also reported to have potential side effects such as stimulatory properties and hypothermia due to systemic administration (Non Patent Literatures 8 and 9). Therefore, the creation of a TRPV1 agonist with excellent safety is desired.

CITATION LIST

Patent Literature

Patent Literature 1: International Publication No. WO 2009/136625
Patent Literature 2: International Publication No. WO 2011/058932
Patent Literature 3: International Publication No. WO 2011/058933
Patent Literature 4: International Publication No. WO 2002/100819
Patent Literature 5: International Publication No. WO 2006/115168

Non Patent Literature

Non Patent Literature 1: Nakazawa, H. et al. Chest. 1993, 103, 1636-1637.
Non Patent Literature 2: Sekizawa, K. et al. LANCET. 1990, 355, 1228-1229.
Non Patent Literature 3: Nakayama, K. et al. Chest. 1998, 113(5), 1425.
Non Patent Literature 4: Funahashi, H. et al. Kyusyu Neuropsychiatry. 2012, 58, 14-21.
Non Patent Literature 5: Nakashima, T. et al. Medicine. 2011, 90(4), 279-283.
Non Patent Literature 6: Iwasaki, K. et al. Phytomedicine. 1999, 6(2), 103-106.
Non Patent Literature 7: Ebihara, T. et al. LANCET. 1993, 341, 432.
Non Patent Literature 8: Fosgerau, K. et al. BMC Cardiovascular Disorders. 2010, 10, 51.
Non Patent Literature 9: Caterina, M. et al. Nature. 1997, 389, 816-824.

SUMMARY OF INVENTION

Technical Problem

An object of the present disclosure is to provide a compound that is useful as a therapeutic drug for dysphagia, improves the swallowing reflex, and has high safety.

Solution to Problem

As a result of diligent studies, the present inventors have found that a compound represented by the following formula (1) has TRPV1-agonistic properties and exhibits an improving effect on dysphagia, and also has antedrug-like properties, thereby completing the present disclosure. According to the present disclosure, the phenol derivative represented by the following formula (1) (hereinafter, also referred to as "compound of the present disclosure") is provided.

That is, the present disclosure is as follows.

(Item 1)

A compound represented by formula (1) or pharmaceutically acceptable salt thereof:

[Chemical Formula 1]

(1)

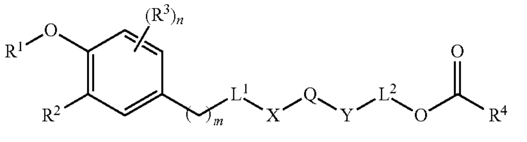

wherein $R^1$ represents a hydrogen atom, an optionally substituted $C_{1-6}$ alkyl group, an optionally substituted $C_{1-6}$ alkylcarbonyl group, or an optionally substituted $C_{6-10}$ arylcarbonyl group;

$R^2$ represents a methoxy group, a hydroxyl group, or a hydrogen atom;

$R^3$ represents a hydrogen atom, a halogen atom, an optionally substituted $C_{1-6}$ alkyl group, an optionally substituted $C_{1-4}$ alkoxy group, an optionally substituted $C_{6-10}$ aryl group, or a formyl group;

$R^4$ represents an optionally substituted $C_{1-6}$ alkyl group, an optionally substituted $C_{3-7}$ alicyclic group, an optionally substituted $C_{2-6}$ alkenyl group, an optionally substituted $C_{2-6}$ alkynyl group, an optionally substituted $C_{6-10}$ aryl group, an optionally substituted $C_{1-6}$ alkoxy group, an optionally substituted $C_{3-7}$ alicyclic oxy group, an optionally substituted $C_{6-10}$ aryloxy group, or an optionally substituted 4- to 7-membered non-aryl heterocyclic group;

m represents 0, 1, or 2;

n represents 0, 1, 2, or 3;

$L^1$ represents —NH—C(=O)—, —C(=O)—NH—, —O—C(=O)—, —C(=O)—O—, —NH—C(=S)—, —C(—S)—NH—, —NH—C(=O)—$CH_2$—, —C(—O)—NH—$CH_2$—, —NH—C(=O)—$CH_2$—$CH_2$—, —C(=O)—NH—$CH_2$—$CH_2$—, —$SO_2$—NH—, —NH—$SO_2$—, —NH—C(=O)—O—, or —O—C(=O)—NH—;

Q represents a single bond, —O—, —S—, —$SO_2$—, —$NR^5$—, or —$CR^6R^7$—;

$L^2$ represents a single bond or an optionally substituted $C_{1-6}$ alkyl group;

X represents an optionally substituted $C_{6-10}$ aryl group or an optionally substituted 5- to 10-membered heteroaryl group;

Y represents an optionally substituted $C_{6-10}$ aryl group, an optionally substituted 5- to 10-membered heteroaryl group, an optionally substituted $C_{3-7}$ alicyclic group, or an optionally substituted 4- to 7-membered non-aryl heterocyclic group; and $R^5$, $R^6$, and $R^7$ each independently represent a hydrogen atom, an optionally substituted $C_{3-6}$ alicyclic group, or an optionally substituted $C_{1-6}$ alkyl group.

(Item 2)

The compound or pharmaceutically acceptable salt thereof according to item 1, wherein $L^1$ is —NH—C(=O)—, —C(=O)—NH—, —NH—C(=S)—, —C(=S)—NH—, —NH—C(=O)—$CH_2$—, —C(=O)—NH—$CH_2$—, —NH—C(=O)—$CH_2$—$CH_2$—, —C(=O)—NH—$CH_2$—$CH_2$—, —$SO_2$—NH—, —NH—$SO_2$—, —NH—C(=O)—O—, or —O—C(=O)—NH—.

(Item 3)

The compound or pharmaceutically acceptable salt thereof according to item 1 or 2, wherein Q is a single bond.

(Item 4)

The compound or pharmaceutically acceptable salt thereof according to any one of items 1 to 3, wherein X is an optionally substituted phenyl group or an optionally substituted 6-membered heteroaryl group.

(Item 5)

The compound or pharmaceutically acceptable salt thereof according to any one of items 1 to 4, wherein Y is an optionally substituted phenyl group, an optionally substituted 5-membered or 6-membered heteroaryl group, an optionally substituted $C_{3-7}$ alicyclic group, or an optionally substituted 4- to 7-membered non-aryl heterocyclic group.

(Item 6)

The compound or pharmaceutically acceptable salt thereof according to item 1, represented by formula (2):

[Chemical Formula 2]

(2)

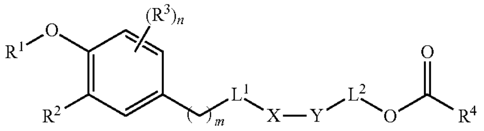

wherein $R^1$ represents a hydrogen atom, a $C_{1-6}$ alkyl group (the $C_{1-6}$ alkyl group is optionally substituted with one to three substituents that are the same or different, selected from the group consisting of a hydroxyl group, a carboxyl group, and —$NR^{11}R^{12}$), an optionally substituted $C_{1-6}$ alkylcarbonyl group, or an optionally substituted $C_{6-10}$ arylcarbonyl group;

$R^2$ represents a methoxy group, a hydroxyl group, or a hydrogen atom;

$R^3$ represents a hydrogen atom, a halogen atom, an optionally substituted $C_{1-6}$ alkyl group, an optionally substituted $C_{1-4}$ alkoxy group, an optionally substituted $C_{6-10}$ aryl group, or a formyl group;

$R^4$ represents an optionally substituted $C_{1-6}$ alkyl group, an optionally substituted $C_{3-7}$ alicyclic group, an optionally substituted $C_{2-6}$ alkenyl group, an optionally substituted $C_{2-6}$ alkynyl group, an optionally substituted $C_{6-10}$ aryl group, an optionally substituted $C_{1-6}$ alkoxy group, an optionally substituted $C_{3-7}$ alicyclic oxy group, an optionally substituted $C_{6-10}$ aryloxy group, or an optionally substituted 4- to 7-membered non-aryl heterocyclic group;

when $R^4$ is an optionally substituted 4- to 7-membered non-aryl heterocyclic group, a carbon atom on the non-aryl heterocycle is bonded to the carbonyl group;

$R^{11}$ represents a hydrogen atom, an optionally substituted $C_{1-3}$ alkyl group, a formyl group, an optionally substituted $C_{1-3}$ alkylcarbonyl group, an optionally substituted $C_{1-4}$ alkoxycarbonyl group, or an optionally substituted $C_{6-10}$ arylcarbonyl group;

$R^{12}$ represents a hydrogen atom or an optionally substituted $C_{1-3}$ alkyl group;

m represents 0, 1, or 2;

n represents 0, 1, 2, or 3;

$L^1$ represents —NH—C(═O)—, —C(═O)—NH—, —NH—C(═S)—, —C(═S)—NH—, —NH—C(═O)—$CH_2$—, —C(═O)—NH—$CH_2$—, —NH—C(═O)—$CH_2$—$CH_2$—, —C(═O)—NH—$CH_2$—$CH_2$—, —$SO_2$—NH—, —NH—$SO_2$—, —NH—C(═O)—O—, or —O—C(═O)—NH—;

$L^2$ represents a single bond or an optionally substituted $C_{1-6}$ alkyl group;

X represents an optionally substituted phenyl group or an optionally substituted 6-membered heteroaryl group;

Y represents an optionally substituted phenyl group, an optionally substituted 5-membered or 6-membered heteroaryl group, an optionally substituted $C_{3-7}$ alicyclic group, or an optionally substituted 4- to 7-membered non-aryl heterocyclic group; and X and Y are bonded at a carbon atom on each ring, provided that the following compounds are excluded:

1) a compound represented by formula (W-1):

[Chemical Formula 3]

(W-1)

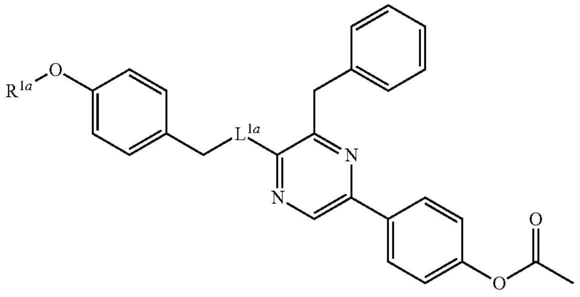

wherein $R^{1a}$ is a hydrogen atom or an acetyl group; and $L^{1a}$ is —C(═O)—NH— or —$SO_2$—NH—;

2) a compound represented by formula (W-2):

[Chemical Formula 4]

(W-2)

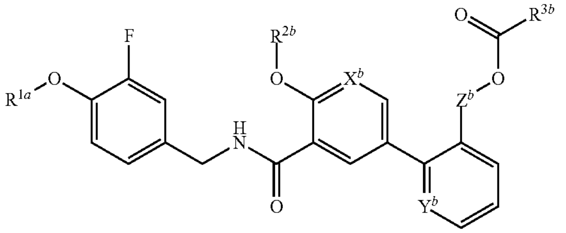

wherein $R^{1b}$ is a methyl group or —$CD_3$;

$R^{2b}$ is the following formula (W-2A), (W-2B), (W-2C), (W-2D), or (W-2R):

[Chemical Formula 5]

(W-2A)

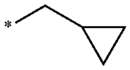

(W-2B)

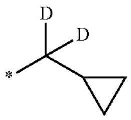

(W-2C)

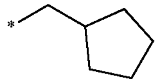

(W-2D)

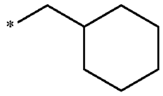

(W-2R)

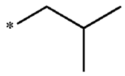

wherein * represents a bonding position with O;

$R^{3b}$ is the following formula (W-2E), (W-2F), (W-2G), (W-2H), (W-2I), (W-2J), (W-2K), (W-2L), (W-2M), (W-2N), (W-20), (W-2P), or (W-2Q):

[Chemical Formula 6]

(W-2E)

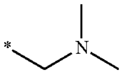

(W-2F)

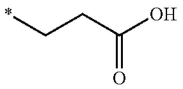

(W-2G)

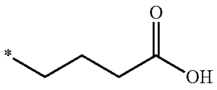

(W-2H)

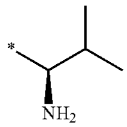

(W-2I)

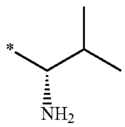

(W-2J)

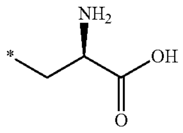

(W-2K)

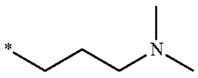

-continued (W-2L)

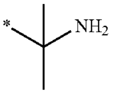

(W-2M)

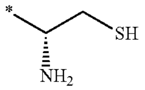

(W-2N)

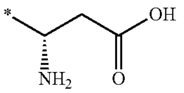

(W-2O)

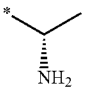

(W-2P)

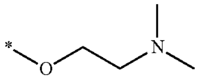

(W-2Q)

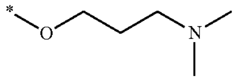

wherein * represents a bonding position with C═O;

$X^b$ is CH or N;

$Y^b$ is CH or N; and $Z^b$ is —$CH_2$— or —CHD-;

3) 4'-{[2-(3,4-dimethoxyphenyl)ethyl]carbamoyl}[1,1'-biphenyl]-4-yl acetate;

4) 2'-(2-{[2-(3,4-dimethoxyphenyl)ethyl]amino}-2-oxoethyl)-4,4',5,5'-tetramethoxy[1,1'-biphenyl]-2-yl acetate;

5) (2'-{[2-(3,4-dimethoxyphenyl)ethyl]carbamoyl}-4,4',5,5'-tetramethoxy[1,1'-biphenyl]-2-yl)methyl benzoate;

6) 6-[4-methoxy-2-(2-{4-[2-(piperidin-1-yl)ethoxy]phenyl}acetamido)phenyl]-5,6,7,8-tetrahydronaphthalen-2-yl 2,2-dimethylpropanoate;

7) 4'-{[(4-methoxyphenyl)methyl]sulfamoyl}[1,1'-biphenyl]-4-yl acetate;

8) 4'-{[(4-methoxyphenyl)methyl]sulfamoyl}[1,1'-biphenyl]-4-yl benzoate;

9) 4'-{[(4-methoxyphenyl)methyl]sulfamoyl}[1,1'-biphenyl]-4-yl 4-chlorobenzoate;

10) 4'-{[(4-methoxyphenyl)methyl]sulfamoyl}[1,1'-biphenyl]-4-yl 2-chlorobenzoate;

11) 4'-{[(4-methoxyphenyl)methyl]sulfamoyl}[1,1'-biphenyl]-4-yl 3-nitrobenzoate; and 12) 4'-{[(4-methoxyphenyl)methyl]sulfamoyl}[1,1'-biphenyl]-4-yl 2,4-dichlorobenzoate.

(Item 7)

The compound or pharmaceutically acceptable salt thereof according to any one of items 1 to 6, wherein $R^3$ is a hydrogen atom.

(Item 8)

The compound or pharmaceutically acceptable salt thereof according to any one of items 1 to 7, wherein m is 1 or 2.

(Item 9)

The compound or pharmaceutically acceptable salt thereof according to any one of items 1 to 8, wherein m is 1.

(Item 10)

The compound or pharmaceutically acceptable salt thereof according to any one of items 1 to 9, wherein $R^1$ is a hydrogen atom.

(Item 11)

The compound or pharmaceutically acceptable salt thereof according to any one of items 1 to 10, wherein $R^2$ is a methoxy group.

(Item 12)

The compound or pharmaceutically acceptable salt thereof according to any one of items 1 to 11, wherein $L^1$ is —NH—C(═O)— or —C(═O)—NH—.

(Item 13)

The compound or pharmaceutically acceptable salt thereof according to any one of items 1 to 12, wherein $L^2$ is a single bond.

(Item 14)

The compound or pharmaceutically acceptable salt thereof according to any one of items 1 to 13, wherein X is the following formula (A):

[Chemical Formula 7]

(A)

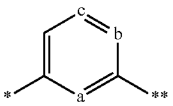

wherein * represents a bonding position with $L^1$ and ** represents a bonding position with Q or Y;

a is $CR^8$ or N;

b is $CR^9$ or N;

c is $CR^{10}$ or N; and $R^8$, $R^9$, and $R^{10}$ are each independently a hydrogen atom, a halogen atom, a cyano group, a $C_{1-6}$ alkylsulfonyl group, an optionally substituted $C_{1-6}$ alkyl group, or an optionally substituted $C_{1-6}$ alkoxy group.

(Item 15)

The compound or pharmaceutically acceptable salt thereof according to any one of items 1 to 14, wherein X is formula (A); and wherein (1) when a is N, b is $CR^9$ and c is $CR^{10}$, (2) when b is N, a is $CR^8$ and c is $CR^{10}$, and (3) when c is N, a is $CR^8$ and b is $CR^9$.

(Item 16)

The compound or pharmaceutically acceptable salt thereof according to any one of items 1 to 14, wherein X is formula (A); and wherein c is $CR^{10}$, and (1) when a is N, b is $CR^9$ and (2) when b is N, a is $CR^8$.

(Item 17)

The compound or pharmaceutically acceptable salt thereof according to any one of items 1 to 14, wherein X is formula (A); and wherein c is CH, and (1) when a is N, b is CH and (2) when b is N, a is CH.

(Item 18)

The compound or pharmaceutically acceptable salt thereof according to any one of items 1 to 14, wherein X is formula (A); and wherein a, b, and c are CH.

(Item 19)

The compound or pharmaceutically acceptable salt thereof according to any one of items 1 to 18, wherein Y is an optionally substituted phenyl group, an optionally substituted 6-membered heteroaryl group, or an optionally substituted $C_3$-7 alicyclic group.

(Item 20)

The compound or pharmaceutically acceptable salt thereof according to any one of items 1 to 19, wherein Y is an optionally substituted phenyl group or an optionally substituted cyclohexyl group.

(Item 21)

The compound or pharmaceutically acceptable salt thereof according to any one of items 1 to 20, wherein Y is the following formula (B) or (C):

[Chemical Formula 8]

(B)

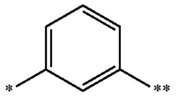

(C)

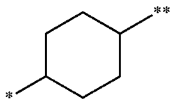

wherein * represents a bonding position with X or Q and ** represents a bonding position with $L^2$ or the oxygen atom.

(Item 22)

The compound or pharmaceutically acceptable salt thereof according to any one of items 1 to 21, wherein $R^4$ is an optionally substituted $C_{1-6}$ alkyl group, an optionally substituted $C_{3-7}$ alicyclic group, an optionally substituted $C_{2-6}$ alkenyl group, an optionally substituted $C_{2-6}$ alkynyl group, or an optionally substituted $C_{6-10}$ aryl group.

(Item 23)

The compound or pharmaceutically acceptable salt thereof according to any one of items 1 to 22, wherein $R^4$ is an optionally substituted $C_{1-6}$ alkyl group, an optionally substituted $C_{3-7}$ alicyclic group, or an optionally substituted $C_{6-10}$ aryl group.

(Item 24)

The compound or pharmaceutically acceptable salt thereof according to any one of items 1 to 23, wherein $R^4$ is a $C_{1-6}$ alkyl group, a $C_{3-7}$ alicyclic group, or a $C_{6-10}$ aryl group (the $C_{1-6}$ alkyl group, $C_{3-7}$ alicyclic group, and $C_{6-10}$ aryl group are optionally substituted with one to three substituents that are the same or different, selected from the group consisting of a fluorine atom, a chlorine atom, a $C_{1-6}$ alkyl group, a $C_{3-7}$ alicyclic group, a $C_{6-10}$ aryl group, a 5-membered or 6-membered heteroaryl group, and a 4- to 10-membered non-aryl heterocyclic group).

(Item 25)

The compound or pharmaceutically acceptable salt thereof according to any one of items 1 to 24, wherein $R^4$ is a methyl group, an ethyl group, an isopropyl group, a cyclohexyl group, a cyclohexylmethyl group, a phenyl group, or a benzyl group (the methyl group, ethyl group, isopropyl group, cyclohexyl group, cyclohexylmethyl group, phenyl group, and benzyl group are optionally substituted with one to three substituents that are the same or different, selected from the group consisting of a fluorine atom, a chlorine atom, and a $C_{1-6}$ alkyl group).

(Item 26)

The compound or pharmaceutically acceptable salt thereof according to any one of items 1 to 25, wherein $R^4$ is a methyl group, an ethyl group, an isopropyl group, a cyclohexyl group, or a phenyl group (the methyl group, ethyl group, isopropyl group, cyclohexyl group, and phenyl group are optionally substituted with one to three substituents that are the same or different, selected from the group consisting of a fluorine atom, a chlorine atom, and a $C_{1-6}$ alkyl group).

(Item 27)

The compound or pharmaceutically acceptable salt thereof according to item 1, selected from the following compounds:

3-{6-[2-(4-hydroxy-3-methoxyphenyl)acetamido]pyridin-2-yl}phenyl 2-methylpropanoate (Example 1);

cis-4-{3-[2-(4-hydroxy-3-methoxyphenyl)acetamido]phenyl}cyclohexyl cyclohexanecarboxylate (Example 2);

3'-[2-(4-hydroxy-3-methoxyphenyl)acetamido][1,1'-biphenyl]-4-yl benzoate (Example 3);

3'-[2-(4-hydroxy-3-methoxyphenyl)acetamido][1,1'-biphenyl]-4-yl 2-methylpropanoate (Example 4);

cis-4-{3-[2-(4-hydroxy-3-methoxyphenyl)acetamido]phenyl}cyclohexyl cyclohexylacetate (Example 5);

cis-4-{3-[2-(4-hydroxy-3-methoxyphenyl)acetamido]phenyl}cyclohexyl phenoxyacetate (Example 6);

cis-4-{3-[2-(4-hydroxy-3-methoxyphenyl)acetamido]phenyl}cyclohexyl (3,5-difluorophenyl)acetate (Example 7);

cis-4-{3-[2-(4-hydroxy-3-methoxyphenyl)acetamido]phenyl}cyclohexyl (4-fluorophenyl)acetate (Example 8);

cis-4-{3-[2-(4-hydroxy-3-methoxyphenyl)acetamido]phenyl}cyclohexyl (3-methylphenyl)acetate (Example 9);

cis-4-{3-[2-(4-hydroxy-3-methoxyphenyl)acetamido]phenyl}cyclohexyl (2-chlorophenyl)acetate (Example 10);

cis-4-{3-[2-(4-hydroxy-3-methoxyphenyl)acetamido]phenyl}cyclohexyl (oxa-4-yl)acetate (Example 11);

cis-4-{3-[2-(4-hydroxy-3-methoxyphenyl)acetamido]phenyl}cyclohexyl acetate (Example 12);

cis-4-{3-[2-(4-hydroxy-3-methoxyphenyl)acetamido]phenyl}cyclohexyl (thiophen-2-yl)acetate (Example 13);

cis-4-{3-[2-(4-hydroxy-3-methoxyphenyl)acetamido]phenyl}cyclohexyl (4-chlorophenyl)acetate (Example 14);

cis-4-{3-[2-(4-hydroxy-3-methoxyphenyl)acetamido]phenyl}cyclohexyl (2-fluorophenyl)acetate (Example 15);

3'-[2-(4-hydroxy-3-methoxyphenyl)acetamido][1,1'-biphenyl]-3-yl propanoate (Example 16);

cis-4-{3-[2-(4-hydroxy-3-methoxyphenyl)acetamido]phenyl}cyclohexyl 2-methylpropanoate (Example 17);

3'-[2-(4-hydroxy-3-methoxyphenyl)acetamido][1,1'-biphenyl]-3-yl phenylacetate (Example 18);

2'-fluoro-5'-[2-(4-hydroxy-3-methoxyphenyl)acetamido][1,1'-biphenyl]-3-yl 2-methylpropanoate (Example 19);

3'-[2-(4-hydroxy-3-methoxyphenyl)acetamido]-4'-methoxy[1,1'-biphenyl]-3-yl 2-methylpropanoate (Example 20);

3'-[2-(4-hydroxy-3-methoxyphenyl)acetamido]-2'-methoxy[1,1'-biphenyl]-3-yl 2-methylpropanoate (Example 21);

4'-fluoro-3'-[2-(4-hydroxy-3-methoxyphenyl)acetamido][1,1'-biphenyl]-3-yl 2-methylpropanoate (Example 22);

2'-fluoro-3'-[2-(4-hydroxy-3-methoxyphenyl)acetamido][1,1'-biphenyl]-3-yl 2-methylpropanoate (Example 23);

3'-[2-(4-hydroxy-3-methoxyphenyl)acetamido][1,1'-biphenyl]-3-yl 2-methylpropanoate (Example 24);

3-{2-[2-(4-hydroxy-3-methoxyphenyl)acetamido]pyridin-4-yl}phenyl 2-methylpropanoate (Example 25);

3-{4-[2-(4-hydroxy-3-methoxyphenyl)acetamido]pyridin-2-yl}phenyl 2-methylpropanoate (Example 26);

3'-[2-(4-hydroxy-3-methoxyphenyl)acetamido][1,1'-biphenyl]-3-yl (4-methylphenyl)acetate (Example 27);

3'-[2-(4-hydroxy-3-methoxyphenyl)acetamido][1,1'-biphenyl]-3-yl (2-fluorophenyl)acetate (Example 28);

3'-[2-(4-hydroxy-3-methoxyphenyl)acetamido][1,1'-biphenyl]-3-yl (oxa-4-yl)acetate (Example 29);

3'-[2-(4-hydroxy-3-methoxyphenyl)acetamido][1,1'-biphenyl]-3-yl cyclohexylacetate (Example 30);

3-{4-[2-(4-hydroxy-3-methoxyphenyl)acetamido]pyridin-2-yl}phenyl cyclohexylacetate (Example 31);

3-{6-[2-(4-hydroxy-3-methoxyphenyl)acetamido]pyridin-2-yl}phenyl cyclohexylacetate (Example 32);

3-{4-[2-(4-hydroxy-3-methoxyphenyl)acetamido]pyridin-2-yl}phenyl cyclohexanecarboxylate hydrochloride (Example 33);

3-{6-[2-(4-hydroxy-3-methoxyphenyl)acetamido]pyridin-2-yl}phenyl cyclohexanecarboxylate (Example 34);

cis-4-{3-[2-(4-hydroxy-3-methoxyphenyl)acetamido]phenyl}cyclohexyl phenylacetate (Example 35);

trans-4-{3-[2-(4-hydroxy-3-methoxyphenyl)acetamido]phenyl}cyclohexyl phenylacetate (Example 36);

trans-4-{3-[2-(4-hydroxy-3-methoxyphenyl)acetamido]phenyl}cyclohexyl cyclohexanecarboxylate (Example 37);

trans-4-{3-[2-(4-hydroxy-3-methoxyphenyl)acetamido]phenyl}cyclohexyl acetate (Example 38);

4-(2-{3-[(cis)-4-(acetyloxy)cyclohexyl]anilino}-2-oxoethyl)-2-methoxyphenyl acetate (Example 39);

4-(2-{3-[(trans)-4-(acetyloxy)cyclohexyl]anilino}-2-oxoethyl)-2-methoxyphenyl acetate (Example 40);

cis-4-{4-[2-(4-hydroxy-3-methoxyphenyl)acetamido]pyridin-2-yl}cyclohexyl acetate (Example 41);

cis-4-(3-{[(4-hydroxy-3-methoxyphenyl)methyl]carbamoyl}phenyl)cyclohexyl acetate (Example 42);

4-[2-({2-[(cis)-4-(acetyloxy)cyclohexyl]pyridin-4-yl}amino)-2-oxoethyl]-2-methoxyphenyl acetate (Example 43);

3'-1{[(4-hydroxy-3-methoxyphenyl)methyl]carbamoyl}[1,1'-biphenyl]-3-yl 2-methylpropanoate (Example 44);

3'-{[(4-hydroxy-3-methoxyphenyl)methyl]carbamoyl}[1,1'-biphenyl]-3-yl cyclohexylacetate (Example 45);

3-(4-{[(4-hydroxy-3-methoxyphenyl)methyl]carbamoyl}pyridin-2-yl)phenyl 2-methylpropanoate (Example 46);

3-(6-{[(4-hydroxy-3-methoxyphenyl)methyl]carbamoyl}pyridin-2-yl)phenyl 2-methylpropanoate (Example 47);

trans-4-{3-[2-(4-hydroxy-3-methoxyphenyl)acetamido]phenyl}cyclohexyl 2-methylpropanoate (Example 48); and 3-{4-[2-(4-hydroxy-3-methoxyphenyl)acetamido]pyridin-2-yl}phenyl 2-methylpropanoate hydrochloride (Example 49).

(Item 28)

The compound or pharmaceutically acceptable salt thereof according to item 1, selected from the following compounds:

3-{6-[2-(4-hydroxy-3-methoxyphenyl)acetamido]pyridin-2-yl}phenyl 2-methylpropanoate (Example 1);

cis-4-{3-[2-(4-hydroxy-3-methoxyphenyl)acetamido]phenyl}cyclohexyl cyclohexanecarboxylate (Example 2);

cis-4-{3-[2-(4-hydroxy-3-methoxyphenyl)acetamido]phenyl}cyclohexyl (3-methylphenyl)acetate (Example 9);

cis-4-{3-[2-(4-hydroxy-3-methoxyphenyl)acetamido]phenyl}cyclohexyl (2-chlorophenyl)acetate (Example 10);

cis-4-{3-[2-(4-hydroxy-3-methoxyphenyl)acetamido]phenyl}cyclohexyl acetate (Example 12);

cis-4-{3-[2-(4-hydroxy-3-methoxyphenyl)acetamido]phenyl}cyclohexyl (2-fluorophenyl)acetate (Example 15);

cis-4-{3-[2-(4-hydroxy-3-methoxyphenyl)acetamido]phenyl}cyclohexyl 2-methylpropanoate (Example 17);

2'-fluoro-5'-[2-(4-hydroxy-3-methoxyphenyl)acetamido][1,1'-biphenyl]-3-yl 2-methylpropanoate (Example 19);

3'-[2-(4-hydroxy-3-methoxyphenyl)acetamido][1,1'-biphenyl]-3-yl 2-methylpropanoate (Example 24);

3-{4-[2-(4-hydroxy-3-methoxyphenyl)acetamido]pyridin-2-yl}phenyl 2-methylpropanoate (Example 26);

3-(4-{[(4-hydroxy-3-methoxyphenyl)methyl]carbamoyl}pyridin-2-yl)phenyl 2-methylpropanoate (Example 46); and 3-{4-[2-(4-hydroxy-3-methoxyphenyl)acetamido]pyridin-2-yl}phenyl 2-methylpropanoate hydrochloride (Example 49).

(Item 29)

A medicament comprising the compound or pharmaceutically acceptable salt thereof according to any one of items 1 to 28 as an active ingredient.

(Item 30)

A therapeutic drug or prophylactic drug for a disorder or disease in which TRPV1 is involved, the drug comprising the compound or pharmaceutically acceptable salt thereof according to any one of items 1 to 28 as an active ingredient.

(Item 31)

The therapeutic drug or prophylactic drug according to item 30, wherein the disorder or disease in which TRPV1 is involved is dysphagia.

(Item 32)

A pharmaceutical composition comprising the compound or pharmaceutically acceptable salt thereof according to any one of items 1 to 28.

(Item 33)

The pharmaceutical composition according to item 32, wherein the composition is for treating or preventing a disorder or disease in which TRPV1 is involved.

(Item 34)

The pharmaceutical composition according to item 32, wherein the composition is for treating or preventing dysphagia.

(Item 35)

A method for treating or preventing a disorder or disease in which TRPV1 is involved, the method comprising administering a therapeutically or prophylactically effective amount of the compound or pharmaceutically acceptable salt thereof according to any one of items 1 to 28 to a patient in need thereof.

(Item 36)

Use of the compound or pharmaceutically acceptable salt thereof according to any one of items 1 to 28 for the manufacture of a therapeutic drug or prophylactic drug for a disorder or disease in which TRPV1 is involved.

(Item 37)

The compound or pharmaceutically acceptable salt thereof according to any one of items 1 to 28, wherein the compound or pharmaceutically acceptable salt thereof is for use in treatment or prevention of a disorder or disease in which TRPV1 is involved.

(Item 38)

A pharmaceutical composition prepared by combining the compound or pharmaceutically acceptable salt thereof according to any one of items 1 to 28 and one or more other agents.

(Item 39)

A pharmaceutical composition comprising the compound or pharmaceutically acceptable salt thereof according to any one of items 1 to 28, the composition is for use in combination with one or more other agents to treat or prevent a disorder or disease in which TRPV1 is involved.

In the present disclosure, it is intended that, in addition to the explicitly stated combinations, one or more of the above characteristics may be provided in further combinations. Still further embodiments and advantages of the present disclosure will be recognized by those skilled in the art upon reading and understanding the following detailed description as necessary.

Advantageous Effects of Invention

Since the compound of the present disclosure exhibits TRPV1-agonistic properties, it is useful as a therapeutic drug for dysphagia induced by agents, dysphagia in the context of neurodegenerative diseases such as Parkinson's disease, and dysphagia in which the swallowing reflex is decreased due to various causes such as cerebrovascular diseases and aging.

BRIEF DESCRIPTION OF DRAWINGS

FIG. 1 shows the effect of improving swallowing in rat haloperidol-induced dysphagia model in Test Example 2. The vertical axis represents the number of swallows (times) and is shown as mean±standard error. The horizontal axis represents the group name (treatment agent).

DESCRIPTION OF EMBODIMENTS

Hereinafter, the present disclosure will be described in further detail. It should be understood that, throughout the present specification, expressions in the singular form encompass the concept of the plural form thereof as well, unless otherwise noted. Accordingly, it should be understood that singular articles (for example, "a", "an", "the", and the like in English) encompass the concept of the plural form thereof as well, unless otherwise noted. In addition, it should be understood that terms used herein are to be used in the sense normally used in the art, unless otherwise noted. Accordingly, unless otherwise defined, all technical terms and scientific and technological terms used herein have the same meaning as generally understood by those skilled in the art to which the present invention pertains. In case of conflict, the present specification (including definitions) shall prevail.

The number of substituents in the groups defined by "optionally substituted" or "substituted" is not particularly limited as long as they can be substituted. In addition, except when there is a special indication, description for each group is applicable to cases where the group is a part of another group or a substituent thereof.

The substituent in "optionally substituted" may be selected from substituent group α consisting of the following, and substitution may take place with one to five substituents that are the same or different. Although not particularly limited by the type of substituent, when the atom to which the substituent is bonded is an oxygen atom, a nitrogen atom, or a sulfur atom, the substituent is limited to those in which the bonding atom is a carbon atom from among the substituents below.

Substituent group α is a group consisting of the following:

1) a halogen atom;
2) a hydroxyl group;
3) a carboxyl group;
4) a cyano group;
5) a $C_{1-6}$ alkyl group;
6) a $C_{2-6}$ alkenyl group;
7) a $C_{2-6}$ alkynyl group;
8) a $C_{1-6}$ alkoxy group;
9) a $C_{1-6}$ alkylthio group;
10) a $C_{1-6}$ alkylcarbonyl group;
11) a $C_{1-6}$ alkylsulfonyl group;

(provided that each substituent of 5) to 11) is optionally substituted with one to five substituents that are the same or different, selected from substituent group β)

12) a $C_{3-10}$ alicyclic group;
13) a $C_{3-10}$ alicyclic oxy group;
14) a $C_{6-10}$ aryloxy group;
15) a 5-membered or 6-membered heteroaryloxy group;
16) a 4- to 10-membered non-aryl heterocyclic oxy group;
17) a $C_{3-10}$ alicyclic thio group;
18) a $C_{6-10}$ arylthio group;
19) a 5-membered or 6-membered heteroarylthio group;
20) a 4- to 10-membered non-aryl heterocyclic thio group;
21) a $C_{6-10}$ aryl group;
22) a 5-membered or 6-membered heteroaryl group;
23) a 4- to 10-membered non-aryl heterocyclic group;
24) a $C_{3-10}$ alicyclic carbonyl group;
25) a $C_{6-10}$ arylcarbonyl group;
26) a 5-membered or 6-membered heteroarylcarbonyl group;
27) a 4- to 10-membered non-aryl heterocyclic carbonyl group;
28) a $C_{3-10}$ alicyclic sulfonyl group;
29) a $C_{6-10}$ arylsulfonyl group;
30) a 5-membered or 6-membered heteroarylsulfonyl group;
31) a 4- to 10-membered non-aryl heterocyclic sulfonyl group;

(provided that each substituent of 12) to 31) is optionally substituted with one to five substituents that are the same or different, selected from a $C_{1-6}$ alkyl group and substituent group β)

32) $—NR^{16}R^{17}$;
33) $—SO_2—NR^{10b}R^{11b}$;
34) $—NR^{10c}—C(═O)R^{11c}$;
35) $—NR^{10d}—C(═O)OR^{11d}$.
36) $—NR^{12a}—C(═O)NR^{10e}R^{11e}$;
37) $—NR^{10f}—C(═S)R^{11f}$;
38) $—NR^{10g}—C(═S)OR^{11g}$;
39) $—NR^{12b}—C(═S) NR^{10h}R^{11h}$;
40) $—NR^{10i}—SO_2—R^{11i}$;
41) $—NR^{12c}—SO_2—NR^{10j}R^{11j}$;
42) $—C(═O)OR^{10k}$;
43) $—C(═O)NR^{10l}R^{11k}$;
44) $—C(═O)NR^{10m}OR^{11l}$;
45) $—C(═O) NR^{12d}—NR^{10n}R^{11m}$;
46) $—C(═S)OR^{10o}$;

47) $—C(=S)NR^{10p}R^{11n}$;
48) $—C(=S)NR^{10q}OR^{11o}$;
49) $—C(=S)NR^{12e}—NR^{10r}R^{11p}$;
50) $—C(=NR^{13a})R^{10s}$;
51) $—C(=NR^{13b})CHO$;
52) $—C(=NR^{13c})NR^{10t}R^{11q}$;
53) $—C(=NR^{13d})NR^{12f}—NR^{10u}R^{11r}$;
54) $—NR^{17c}—C(=NR^{13k})R^{17d}$;
55) $—NR^{12g}—C(=NR^{13e})—NR^{10v}R^{11s}$;
56) $—NR^{14}—C(=NR^{13f})NR^{12h}—NR^{10w}R^{11t}$;
57) $—OC(=O)R^{10x}$;
58) $—OC(=O)OR^{10y}$;
59) $—OC(=O)NR^{10z1}R^{11u}$;
60) $—NR^{12i}—NR^{10z2}R^{11v}$;
61) $—NR^{10z3}OR^{11w}$;
62) $—C(=N—OR^{13a})R^{10s}$,
63) $—C(=N—OR^{13b})CHO$;
64) $—C(=N—OR^{13c})NR^{10t}R^{11q}$;
65) $—C(=N—OR^{13d})NR^{12f}—NR^{10u}R^{11r}$; and
66) $—C(=O)H$, substituent group β is a group consisting of the following:

1) a halogen atom;
2) a hydroxyl group;
3) a carboxyl group;
4) a cyano group;
5) a $C_{3-10}$ alicyclic group;
6) a $C_{1-6}$ alkoxy group;
7) a $C_{3-10}$ alicyclic oxy group;
8) a $C_{1-6}$ alkylthio group;
9) a 5-membered or 6-membered heteroarylthio group;
10) a $C_{6-10}$ aryl group;
11) a 5-membered or 6-membered heteroaryl group;
12) a 4- to 10-membered non-aryl heterocyclic group;
13) a $C_{1-6}$ alkylcarbonyl group;
14) a $C_{3-10}$ alicyclic carbonyl group;
15) a $C_{6-10}$ arylcarbonyl group;
16) a 5-membered or 6-membered heteroarylcarbonyl group;
17) a 4- to 10-membered non-aryl heterocyclic carbonyl group;
18) $—NR^{15a}R^{16a}$;
19) $—SO_2—NR^{15b}R^{16b}$;
20) $—NR^{15c}—C(=O)R^{16c}$;
21) $—NR^{17a}—C(=O)NR^{15d}R^{16d}$;
22) $—C(=O) NR^{15e}R^{16e}$;
23) $—C(=NR^{13g})R^{15f}$;
24) $—C(=NR^{13h})NR^{15g}R^{16f}$;
25) $—NR^{16g}—C(=NR^{13i})R^{15h}$;
26) $—NR^{17b}—C(=NR^{13j})—NR^{15i}R^{16h}$;
27) $—C(=N—OR^{13g})R^{15f}$; and
28) $—C(=N—OR^{13h})NR^{15g}R^{16f}$ (provided that each substituent of 5) to 17) among substituent group β is optionally substituted with one to five substituents selected from the group consisting of a halogen atom, a hydroxyl group, a cyano group, a carboxyl group, and $—NR^{18a}R^{18b}$), $R^{13a}$, $R^{13b}$, $R^{13c}$, $R^{13d}$, $R^{13e}$, $R^{13f}$, $R^{13g}$, $R^{13h}$, $R^{13i}$, $R^{13j}$, and $R^{13k}$ are each independently a hydrogen atom, a hydroxyl group, a $C_{1-6}$ alkyl group, or a $C_{1-6}$ alkoxy group, $R^{10a}$, $R^{10b}$, $R^{10c}$, $R^{10d}$, $R^{10e}$, $R^{10f}$, $R^{10g}$, $R^{10h}$, $R^{10i}$, $R^{10j}$, $R^{10k}$, $R^{10l}$, $R^{10m}$, $R^{10n}$, $R^{10o}$, $R^{10p}$, $R^{10q}$, $R^{10r}$, $R^{10s}$, $R^{10t}$, $R^{10u}$, $R^{10v}$, $R^{10w}$, $R^{10x}$, $R^{10y}$, $R^{10z1}$, $R^{10z2}$, $R^{10z3}$, $R^{11a}$, $R^{11b}$, $R^{11c}$, $R^{11d}$, $R^{11c}$, $R^{11f}$, $R^{11g}$, $R^{11h}$, $R^{11i}$, $R^{11j}$, $R^{11k}$, $R^{11l}$, $R^{11m}$, $R^{11n}$, $R^{11o}$, $R^{11p}$, $R^{11q}$, $R^{11r}$, $R^{11s}$, $R^{11t}$, $R^{11u}$, $R^{11v}$, $R^{11w}$, $R^{12a}$, $R^{12b}$, $R^{12c}$, $R^{12d}$, $R^{12e}$, $R^{12f}$, $R^{12g}$, $R^{12h}$, $R^{12i}$, $R^{14}$, $R^{15a}$, $R^{15b}$, $R^{15c}$, $R^{15d}$, $R^{15e}$, $R^{15f}$, $R^{15g}$, $R^{15h}$, $R^{15i}$, $R^{16a}$, $R^{16b}$, $R^{16c}$, $R^{16d}$, $R^{16e}$, $R^{16f}$, $R^{16g}$, $R^{16h}$, $R^{17a}$, $R^{17b}$, $R^{17c}$, and $R^{17d}$ are each independently a hydrogen atom or a $C_{1-6}$ alkyl group (the group is optionally substituted with one to three substituents selected from the group consisting of a hydroxyl group, a cyano group, a $C_{1-6}$ alkoxy group, and $—NR^{18a}R^{18b}$), and $R^{18a}$ and $R^{18b}$ are each independently a hydrogen atom or a $C_{1-6}$ alkyl group.

Preferred examples of the substituent in "optionally substituted" include the following substituents.

Substituent group α is preferably a group consisting of the following:

1) a halogen atom;
2) a hydroxyl group;
3) a carboxyl group;
4) a cyano group;
5) a $C_{1-6}$ alkyl group;
6) a $C_{1-6}$ alkoxy group;
7) a $C_{1-6}$ alkylthio group;
8) a $C_{1-6}$ alkylcarbonyl group;

(provided that each substituent of 5) to 8) is optionally substituted with one to five substituents that are the same or different, selected from substituent group β)

9) a $C_{3-10}$ alicyclic group;
10) a $C_{3-10}$ alicyclic oxy group;
11) a $C_{6-10}$ aryloxy group;
12) a 5-membered or 6-membered heteroaryloxy group;
13) a 4- to 10-membered non-aryl heterocyclic oxy group;
14) a $C_{3-10}$ alicyclic thio group;
15) a $C_{6-10}$ arylthio group;
16) a 5-membered or 6-membered heteroarylthio group;
17) a 4- to 10-membered non-aryl heterocyclic thio group;
18) a $C_{6-10}$ aryl group;
19) a 5-membered or 6-membered heteroaryl group;
20) a 4- to 10-membered non-aryl heterocyclic group;
21) a $C_{3-10}$ alicyclic carbonyl group;
22) a $C_{6-10}$ arylcarbonyl group;
23) a 5-membered or 6-membered heteroarylcarbonyl group;
24) a 4- to 10-membered non-aryl heterocyclic carbonyl group; (provided that each substituent of 9) to 24) is optionally substituted with one to five substituents that are the same or different, selected from a $C_{1-6}$ alkyl group and substituent group β)
25) $—NR^{10a}R^{11a}$;
26) $—SO_2—NR^{10b}R^{11b}$;
27) $—NR^{10c}—C(=O)R^{11c}$;
28) $—NR^{12a}—C(=O)NR^{10d}R_{11d}$;
29) $—NR^{10e}—SO_2—R^{11e}$;
30) $—NR^{12b}—SO_2—NR^{10f}R^{11f}$;
31) $—C(=O)NR^{10g}R^{11g}$;
32) $—C(=NR^{13a})R^{10h}$;
33) $—C(=NR^{13b})NR^{10i}R^{11h}$;
34) $—NR^{11f}—C(=NR^{13c})R^{10g}$;
35) $—NR^{12c}—C(=NR^{13d})—NR^{10j}R^{11i}$;
36) $—C(=N—OR^{13a})R^{10h}$; and
37) $—C(=N—OR^{13b})NR^{10i}R^{11h}$, substituent group β is preferably a group consisting of the following:

1) a halogen atom;
2) a hydroxyl group;
3) a cyano group;
4) a $C_{3-10}$ alicyclic group;
5) a $C_{1-6}$ alkoxy group;
6) a $C_{1-6}$ alkylthio group;

7) a 5-membered or 6-membered heteroarylthio group;
8) a 5-membered or 6-membered heteroaryl group;
9) a 4- to 10-membered non-aryl heterocyclic group;
10) a $C_{1-6}$ alkylcarbonyl group;
11) a $C_{3-10}$ alicyclic carbonyl group;
12) a $C_{6-10}$ arylcarbonyl group;
13) a 5-membered or 6-membered heteroarylcarbonyl group;
14) a 4- to 10-membered non-aryl heterocyclic carbonyl group;
15) —$NR^{15a}R^{16a}$;
16) —$NR^{15b}$—C(═O)$R^{16b}$;
17) —$NR^{17s}$—C(═O)$NR^{15c}R^{16c}$;
18) —C(═O)$NR^{15d}R^{16d}$;
19) —C(═$NR^{13e}$)$R^{15e}$;
20) —C(═$NR^{13f}$)$NR^{15f}R^{16e}$;
21) —$NR^{16f}$—C(═$NR^{13g}$)$R^{15g}$;
22) —$NR^{17b}$—C(═$NR^{13h}$)—$NR^{15h}R^{16g}$;
23) —C(═N—$OR^{13e}$)$R^{15e}$; and
24) —C(═N—$OR^{13f}$)$NR^{15f}R^{16e}$;
(provided that each substituent of 4) to 14) among substituent group 3 is optionally substituted with one to five substituents selected from the group consisting of a halogen atom, a hydroxyl group, a cyano group, a carboxyl group, and —$NR^{18a}R^{18b}$)
$R^{13a}$, $R^{13b}$, $R^{13c}$, $R^{13d}$, $R^{13e}$, $R^{13f}$, $R^{13g}$, and $R^{13h}$ are each independently a hydrogen atom, a hydroxyl group, a $C_{1-6}$ alkyl group, or a $C_{1-6}$ alkoxy group,
$R^{10a}$, $R^{10b}$, $R^{10c}$, $R^{10d}$, $R^{10e}$, $R^{10f}$, $R^{10g}$, $R^{10h}$, $R^{10i}$, $R^{10j}$, $R^{11a}$, $R^{11b}$, $R^{11c}$, $R^{11d}$, $R^{11e}$, $R^{11f}$, $R^{11g}$, $R^{11h}$, $R^{11i}$, $R^{12a}$, $R^{12b}$, $R^{12c}$, $R^{15a}$, $R^{15b}$, $R^{15c}$, $R^{15d}$, $R^{15e}$, $R^{15f}$, $R^{15g}$, $R^{15h}$, $R^{16a}$, $R^{16b}$, $R^{16c}$, $R^{16d}$, $R^{16e}$, $R^{16f}$, $R^{16g}$, $R^{17a}$, and $R^{17b}$ are each independently a hydrogen atom or a $C_{1-6}$ alkyl group (the group is optionally substituted with one to three substituents selected from the group consisting of a hydroxyl group, a cyano group, a $C_{1-6}$ alkoxy group, and —$NR^{18a}R^{18b}$) and
$R^{18a}$ and $R^{18b}$ are each independently a hydrogen atom or a $C_{1-6}$ alkyl group.

Still preferred examples of the substituent in "optionally substituted" include the following substituents.

Substituent group α is still preferably a group consisting of the following:
1) a halogen atom;
2) a hydroxyl group;
3) a cyano group;
4) a $C_{1-6}$ alkyl group;
5) a $C_{1-6}$ alkoxy group;
6) a $C_{1-6}$ alkylthio group;
7) a $C_{1-6}$ alkylcarbonyl group;
(provided that each substituent of 4) to 7) is optionally substituted with one to five substituents that are the same or different, selected from substituent group 3)
8) a 5-membered or 6-membered heteroaryloxy group;
9) a 4- to 10-membered non-aryl heterocyclic oxy group;
10) a 5-membered or 6-membered heteroarylthio group;
11) a 4- to 10-membered non-aryl heterocyclic thio group;
12) a $C_{6-10}$ aryl group;
13) a 5-membered or 6-membered heteroaryl group;
14) a 4- to 10-membered non-aryl heterocyclic group; (provided that each substituent of 4) to 14) is optionally substituted with one to five substituents that are the same or different, selected from a $C_{1-6}$ alkyl group and substituent group 3)
15) —$NR^{10a}R^{11a}$;
16) —$NR^{11b}$—C(═O)$R^{10b}$;
17) —$NR^{12a}$—C(═O)$NR^{10c}R^{11c}$;
18) —C(═O)$NR^{10d}R^{11d}$;
19) —C(═$NR^{13a}$)$R^{10e}$;
20) —C(═$NR^{13b}$)$NR^{10f}R^{11e}$;
21) —$NR^{11f}$—C═$R^{13c}$)$R^{10g}$;
22) —$NR^{12b}$—C(═$NR^{13d}$)—$N^{10h}R^{11g}$;
23) —C(═N—$OR^{13a}$)$R^{10e}$; and
24) —C(═N—$OR^{13b}$)$NR^{10f}R^{11e}$,
substituent group β is still preferably a group consisting of the following:
1) a halogen atom;
2) a hydroxyl group;
3) a cyano group;
4) —$NR^{15a}R^{16a}$;
5) —$NR^{15b}$C(═O)$R^{16b}$;
6) —$NR^{17a}$—C(═O)$NR^{15c}R^{16c}$;
7) —C(═O)$NR^{15d}R^{16d}$;
8) —C(═$NR^{13e}$)$R^{15e}$;
9) —C(═$NR^{13f}$)$NR^{15f}R^{16e}$;
10) —$NR^{16f}$—C(═$NR^{13g}$)$R^{15g}$;
11) —$NR^{17b}$—C(═$NR^{13h}$)—$NR^{15h}R^{16g}$;
12) —C(═N—$OR^{13e}$)$R^{15e}$; and
13) —C(═N—$OR^{13f}$)$NR^{15f}R^{16e}$,
$R^{13a}$, $R^{13b}$, $R^{13c}$, $R^{13d}$, $R^{13e}$, $R^{13f}$, $R^{13g}$ and $R^{13h}$ are each independently a hydrogen atom, a hydroxyl group, a $C_{1-6}$ alkyl group, or a $C_{1-6}$ alkoxy group,
$R^{10a}$, $R^{11b}$, $R^{10c}$, $R^{10d}$, $R^{10e}$, $R^{10f}$, $R^{10g}$, $R^{10h}$, $R^{11a}$, $R^{11b}$, $R^{11c}$, $R^{11d}$, $R^{11e}$, $R^{11f}$, $R^{11g}$, $R^{12a}$, $R^{12b}$, $R^{15a}$, $R^{15b}$, $R^{15c}$, $R^{15d}$, $R^{15e}$, $R^{15f}$, $R^{15g}$, $R^{15h}$, $R^{16a}$, $R^{16b}$, $R^{16c}$, $R^{16d}$, $R^{16e}$, $R^{16f}$, $R^{16g}$, $R^{17a}$, and $R^{17b}$ are each independently a hydrogen atom or a $C_{1-6}$ alkyl group (the group is optionally substituted with one to three substituents selected from the group consisting of a hydroxyl group, a cyano group, a $C_{1-6}$ alkoxy group, and —$NR^{18a}R^{18b}$), and $R^{18a}$ and $R^{18b}$ are each independently a hydrogen atom or a $C_{1-6}$ alkyl group.

The term "$C_{1-6}$" means that the number of carbon atoms is 1 to 6. The same applies to other numbers as well, and for example, the term "$C_{1-4}$" means that the number of carbon atoms is 1 to 4.

The term "heteroatom" means an oxygen atom, a nitrogen atom, a sulfur atom, or the like.

The term "halogen atom" refers to any atom other than carbon atom and hydrogen atom, and means a fluorine atom, a chlorine atom, a bromine atom, and an iodine atom. Among them, a fluorine atom and a chlorine atom are preferable. "Halogen atom" may also be referred to as "halogen".

The term "$C_{1-6}$ alkyl" or "$C_{1-6}$ alkyl group" means a linear or branched saturated hydrocarbon group having 1 to 6 carbon atoms. Examples of the $C_{1-6}$ alkyl group preferably include a "$C_{1-4}$ alkyl group", and more preferably include a "$C_{1-3}$ alkyl group". Specific examples of the "$C_{1-3}$ alkyl group" include methyl, ethyl, propyl, and 1-methylethyl. Specific examples of the "$C_{1-4}$ alkyl group" include butyl, 1,1-dimethylethyl, 1-methylpropyl, and 2-methylpropyl, in addition to those mentioned as the aforementioned specific examples of the "$C_{1-3}$ alkyl group". Specific examples of the "$C_{1-6}$ alkyl group" include pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, and hexyl, in addition to those mentioned as the aforementioned specific examples of the "$C_{1-4}$ alkyl group".

The term "$C_{2-6}$ alkenyl" or "$C_{2-6}$ alkenyl group" means a linear or branched unsaturated hydrocarbon group having 2 to 6 carbon atoms that contains one or two or more carbon-carbon double bonds. The "$C_{2-6}$ alkenyl group" is preferably a “$C_{24}$ alkenyl group”. Specific examples of the “$C_{2-6}$ alkenyl group” include, but are not limited to, a vinyl group, a 1-propylenyl group, a 2-propylenyl group, a 1-butenyl group, a 2-butenyl group, a 3-butenyl group, a 2-methyl-1-propylenyl group, and a 2-methyl-2-propylenyl group.

The term “$C_{2-6}$ alkynyl” or “$C_{2-6}$ alkynyl group” means a linear or branched unsaturated aliphatic hydrocarbon group having 2 to 6 carbon atoms that has one or two or more carbon-carbon triple bonds. The “$C_{2-6}$ alkynyl group” is preferably a “$C_{24}$ alkynyl group”. Specific examples of the “$C_{2-6}$ alkynyl group” include, but are not limited to, an ethynyl group, a 1-propynyl group, a 2-propynyl group, a 1-butynyl group, a 1-methyl-2-propynyl group, a 3-butynyl group, a 1-pentynyl group, and a 1-hexynyl group.

The term “$C_{3-10}$ alicyclic group” means a monocyclic or bicyclic monovalent non-aromatic hydrocarbon ring group having 3 to 10 carbon atoms, and those partially having an unsaturated bond, partially having a crosslinked structure, partially being spirocyclized, and having one or two or more carbonyl structures are also encompassed. The “alicyclic group” encompasses a cycloalkyl group, a cycloalkenyl group, and a cycloalkynyl group. Examples of the “$C_{3-10}$ alicyclic group” preferably include a “$C_{3-7}$ alicyclic group”, and still more preferably include a “$C_{5-6}$ alicyclic group”. Specific examples of the “$C_{5-6}$ alicyclic group” include cyclopentyl and cyclohexyl. Specific examples of the “$C_{3-7}$ alicyclic group” include cyclopropyl, cyclobutyl, and cycloheptyl, in addition to those mentioned as the aforementioned specific examples of the “$C_{5-6}$ alicyclic group”. Specific examples of the “$C_{3-10}$ alicyclic group” include cyclooctyl, cyclononyl, cyclodecyl, and adamantyl, in addition to those mentioned as the aforementioned specific examples of the “$C_{3-7}$ alicyclic group”.

Specific examples of the “$C_{3-10}$ alicyclic group” partially having a crosslinked structure include, but are not limited to, those with the structures shown below.

[Chemical Formula 9]

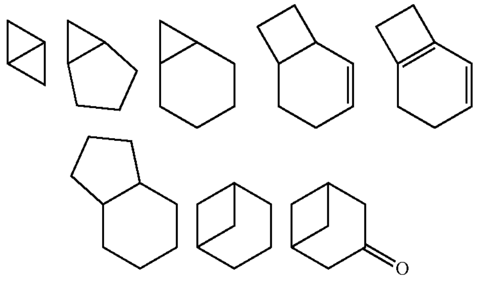

In addition, the “$C_{3-10}$ alicyclic group” also encompasses a compound that has been fused with an aromatic ring. Specific examples thereof include groups represented by the following.

[Chemical Formula 10]

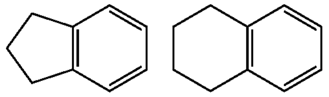

The term “$C_{6-10}$ aryl group” means a monocyclic or bicyclic aromatic hydrocarbon group having 6 to 10 carbon atoms. The “$C_{6-10}$ aryl group” may be fused at all possible positions with the aforementioned “alicyclic group” or the “non-aryl heterocyclic group” described later. Specific examples of the “$C_{6-10}$ aryl group” include a phenyl group, a 1-naphthyl group, and a 2-naphthyl group. Examples of the “$C_{6-10}$ aryl group” preferably include a phenyl group. Specific examples of the fused ring structure include groups represented by the following.

[Chemical Formula 11]

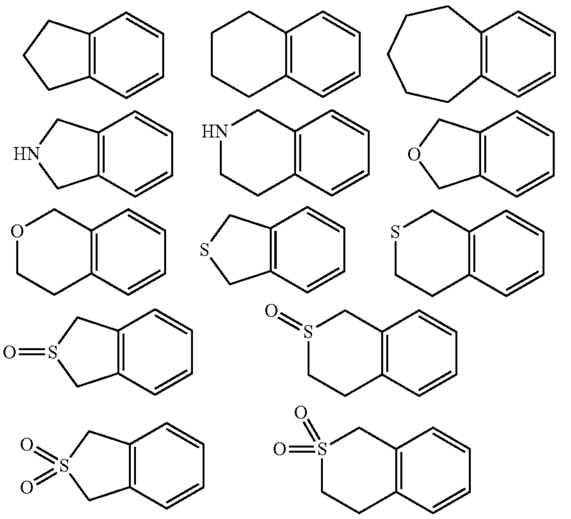

[Chemical Formula 12]

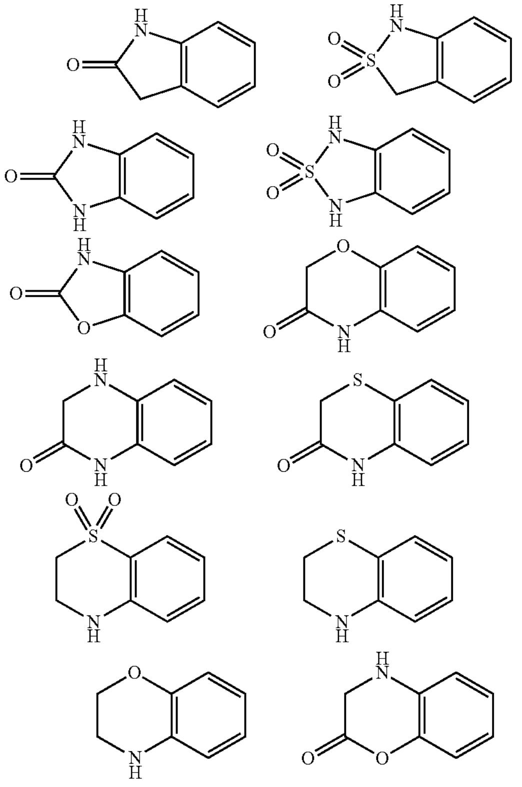

The term “5- to 10-membered heteroaryl group” means a monocyclic or bicyclic aromatic heterocyclic group constituted by 5 to 10 atoms, including 1 to 4 atoms independently selected from the group consisting of a nitrogen atom, an oxygen atom, and a sulfur atom. The “5- to 10-membered heteroaryl group" may be fused at all possible positions with the aforementioned "alicyclic group" or the "non-aryl heterocyclic group" described later. Examples of the "5- to 10-membered heteroaryl group" preferably include a "6-membered heteroaryl group", a "5-membered or 6-membered heteroaryl group", a "6- to 10-membered heteroaryl group", or a "9-membered or 10-membered heteroaryl group". Examples thereof more preferably include a "6-membered heteroaryl group" and a "5-membered or 6-membered heteroaryl group". Specific examples of the "6-membered heteroaryl group" include a pyridyl group, a pyrazinyl group, a pyrimidinyl group, and a pyridazinyl group. Specific examples of the "5-membered or 6-membered heteroaryl group" include a furyl group, a thienyl group, a pyrrolyl group, a pyrazolyl group, an oxazolyl group, a thiazolyl group, an imidazolyl group, an isoxazolyl group, a pyridyl group, a pyrazinyl group, a pyrimidinyl group, and a pyridazinyl group. Specific examples of the "6- to 10-membered heteroaryl group" include a pyridyl group, a pyrazinyl group, a pyrimidinyl group, a pyridazinyl group, a quinoxalyl group, and a triazolopyridyl group. Specific examples of the "5- to 10-membered heteroaryl group" include the aforementioned specific examples of the "6- to 10-membered heteroaryl group" and "5-membered or 6-membered heteroaryl group".

Specific examples of the "9-membered or 10-membered heteroaryl group" include, but are not limited to, those with the structures shown below.

[Chemical Formula 13]

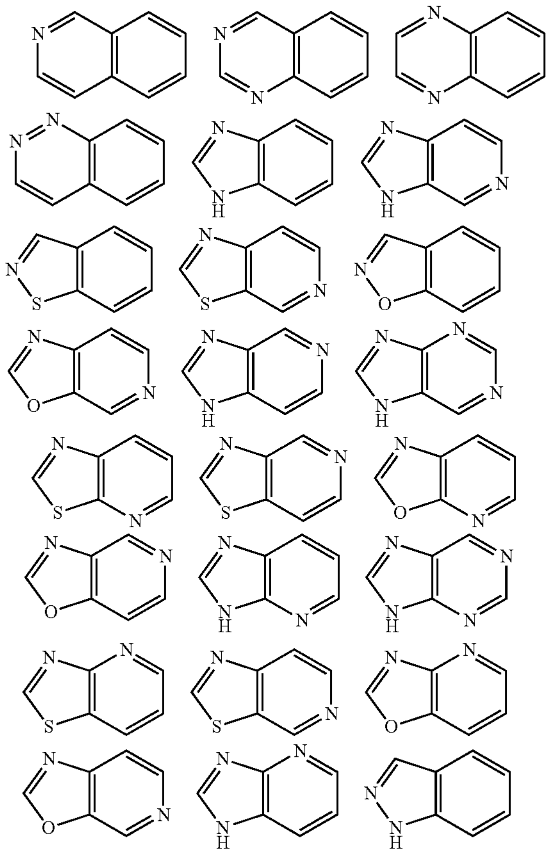

-continued

[Chemical Formula 14]

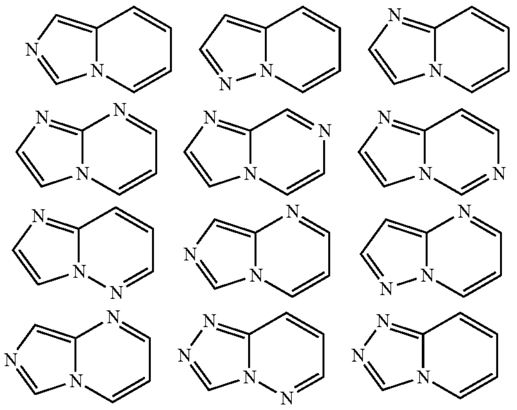

The aforementioned "5-membered or 6-membered heteroaryl group" or "5- to 10-membered heteroaryl group" may form a fused ring structure with a $C_{5-10}$ alicyclic group or with a 5- to 10-membered non-aryl heterocycle. Specific examples thereof include groups represented by the following.

[Chemical Formula 15]

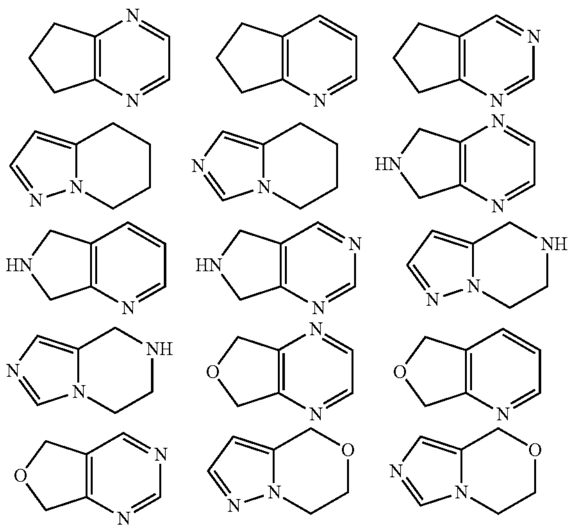

[Chemical Formula 16]

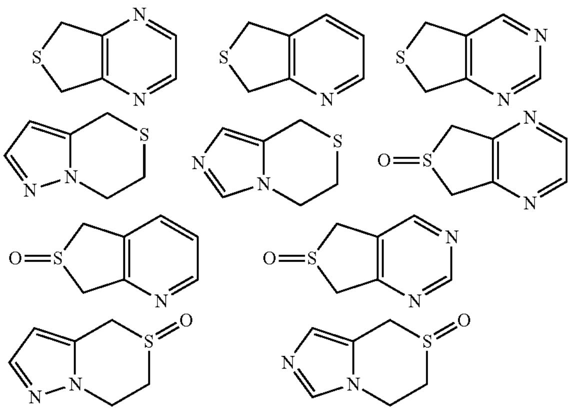

-continued

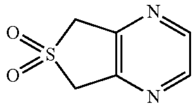 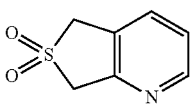

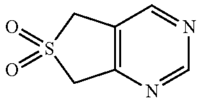 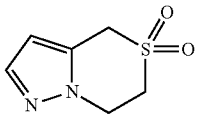

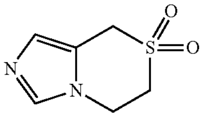

[Chemical Formula 17]

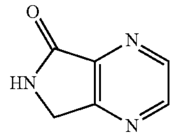 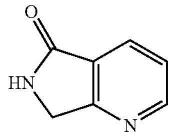

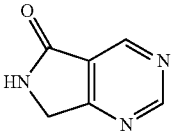 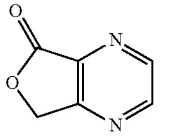

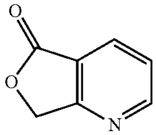 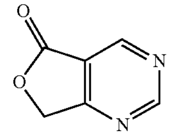

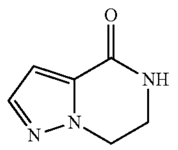 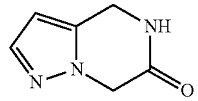

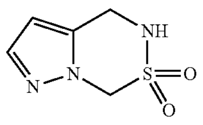 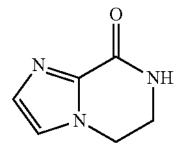

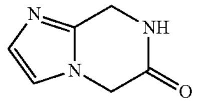 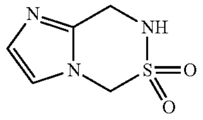

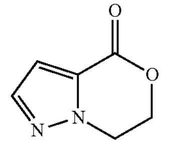 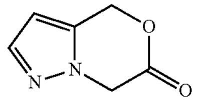

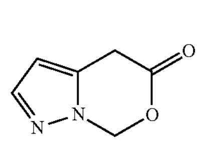 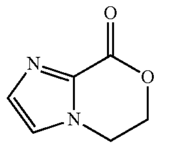

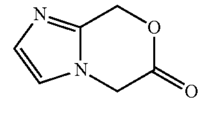 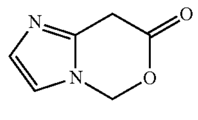

-continued

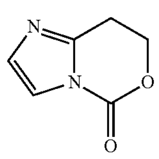 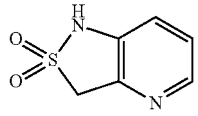

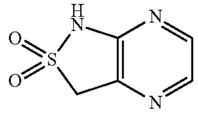 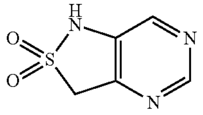

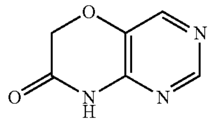 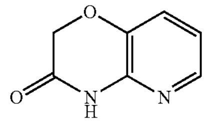

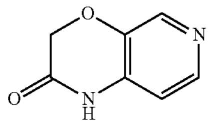 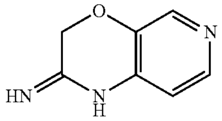

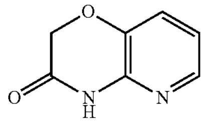 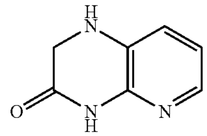

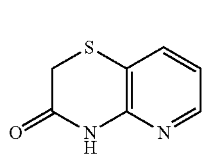 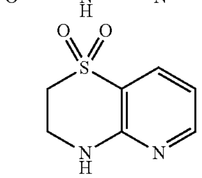

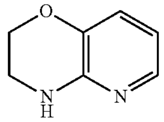 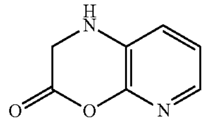

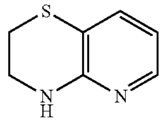

The term “4- to 10-membered non-aryl heterocyclic group” means a monocyclic or bicyclic non-aromatic heterocycle constituted by 4 to 10 atoms, including one to two heteroatoms that are the same or different independently selected from the group consisting of a nitrogen atom, an oxygen atom, and a sulfur atom, in addition to carbon atoms, and encompasses those partially having an unsaturated bond, partially having a crosslinked structure, and/or partially being spirocyclized. The “4- to 10-membered non-aryl heterocyclic group” is preferably a “4- to 7-membered non-aryl heterocyclic group”. Specific examples of the “4- to 7-membered non-aryl heterocyclic group” include an azetidinyl group, a pyrrolidinyl group, a piperidyl group, a piperazinyl group, a morpholinyl group, an oxetanyl group, a tetrahydrofuranyl group, and a tetrahydropyranyl group. Specific examples thereof preferably include an azetidinyl group, a pyrrolidinyl group, a piperidyl group, a morpholinyl group, and an oxetanyl group. The non-aryl heterocycle may form a fused ring with an aryl or with a heteroaryl. For example, when fused with a $C_{6-10}$ aryl group or with a 5-membered or 6-membered heteroaryl group, it is also encompassed in the non-aryl heterocycle. In addition, in constituting the non-aryl heterocycle, it may contain one or two or more carbonyl groups, thiocarbonyl groups, sulfinyl groups, or sulfonyl groups, and a cyclic group is also contained in the non-aryl heterocycle, such as a lactam, a thiolactam, a lactone, a thiolactone, a cyclic imide, a cyclic carbamate, and a cyclic thiocarbamate. Here, the oxygen atom in the carbonyl group, sulfinyl group, and sulfonyl group and the sulfur atom in the thiocarbonyl group are not included in the number of 4 to 10 members (ring size) and the number of heteroatoms constituting the ring. The "4- to 10-membered non-aryl heterocycle" is preferably a "4- to 7-membered non-aryl heterocycle". Specific examples of the "4- to 7-membered non-aryl heterocycle" include azetidine, pyrrolidine, piperidine, piperazine, morpholine, homopiperidine, oxetane, tetrahydrofuran, and tetrahydropyran. Specific examples of the "4- to 10-membered non-aryl heterocycle" include those with the structures shown below, in addition to those mentioned as the aforementioned specific examples of the "4- to 7-membered non-aryl heterocycle".

[Chemical Formula 18]

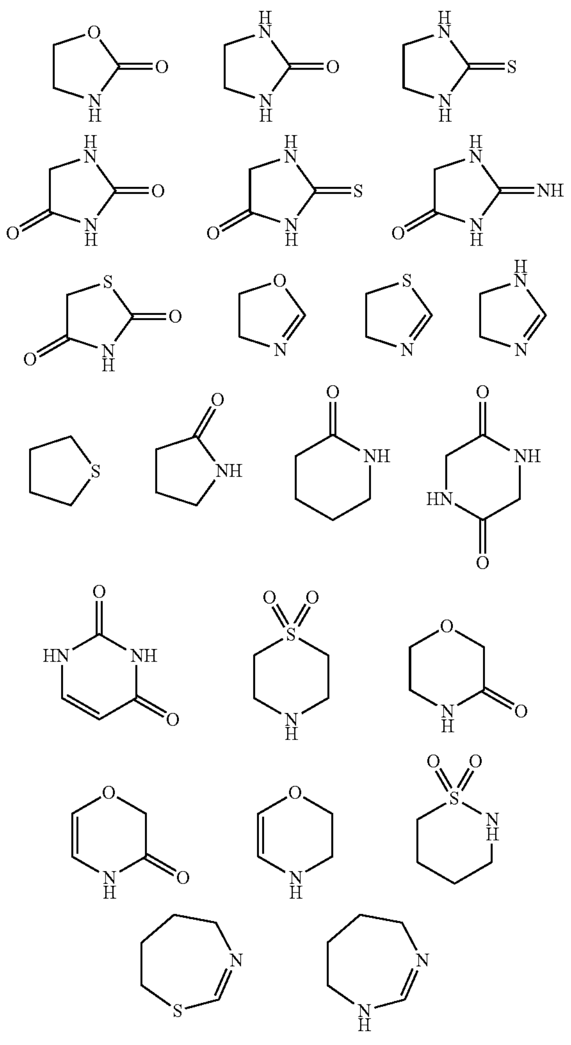

In addition, specific examples of the "4- to 10-membered non-aryl heterocycle" partially having a crosslinked and/or spiro structure include, but are not limited to, those with the structures shown below.

[Chemical Formula 19]

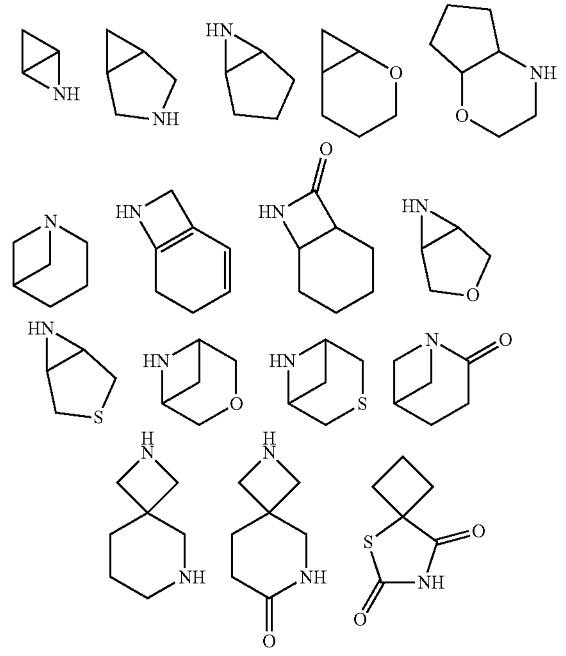

In addition, specific examples of the "4-membered non-aryl heterocycle" partially having an unsaturated bond include, but are not limited to, those with the structures shown below.

[Chemical Formula 20]

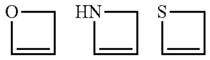

In addition, specific examples of the "5-membered non-aryl heterocycle" partially having an unsaturated bond include, but are not limited to, those with the structures shown below.

[Chemical Formula 21]

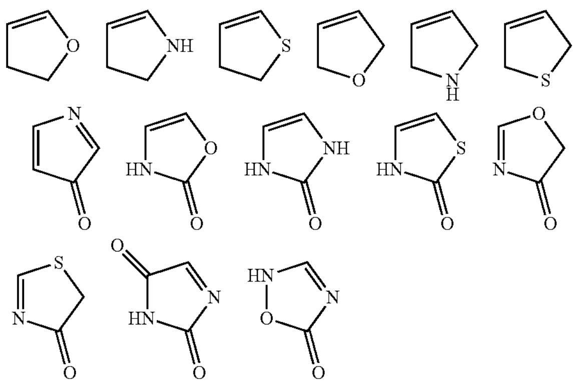

In addition, specific examples of the "5-membered non-aryl heterocycle" partially having a crosslinked structure include, but are not limited to, those with the structures shown below.

[Chemical Formula 22]

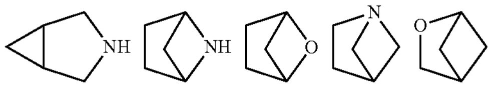

In addition, specific examples of the "5-membered non-aryl heterocycle" containing carbonyl, thiocarbonyl, and the like include, but are not limited to, those with the structures shown below.

[Chemical Formula 23]

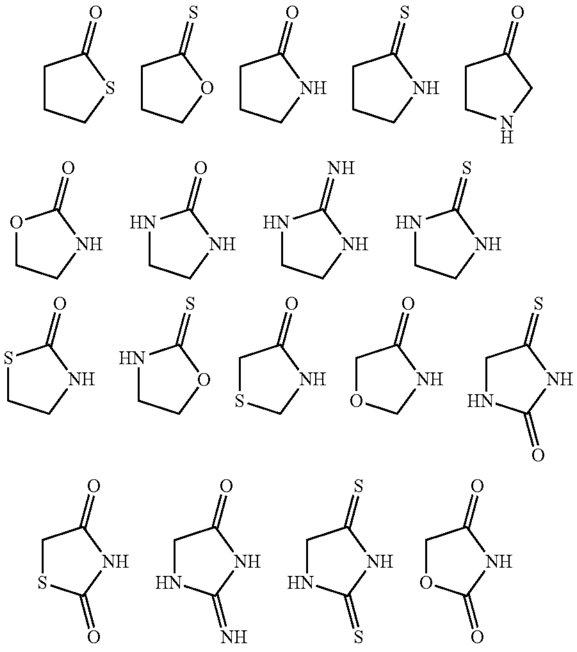

In addition, specific examples of the "6-membered non-aryl heterocycle" partially having an unsaturated bond include, but are not limited to, those with the structures shown below.

[Chemical Formula 24]

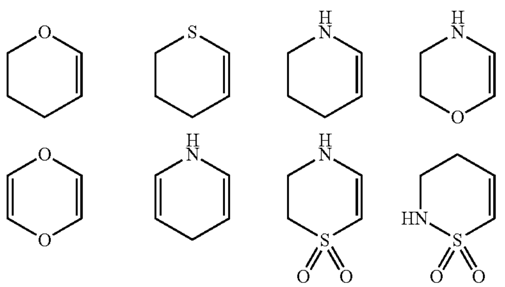

In addition, specific examples of the "6-membered non-aryl heterocycle" partially having a crosslinked structure include, but are not limited to, those with the structures shown below.

[Chemical Formula 25]

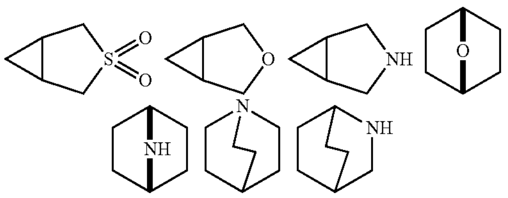

The term "$C_{1-6}$ alkoxy" or "$C_{1-6}$ alkoxy group" means a "$C_{1-6}$ alkyloxy", and the "$C_{1-6}$ alkyl" moiety is the same as the aforementioned "$C_{1-6}$ alkyl". Examples of the "$C_{1-6}$ alkoxy" preferably include a "$C_{1-4}$ alkoxy", and more preferably include a "$C_{1-3}$ alkoxy". Specific examples of the "$C_{1-3}$ alkoxy" include methoxy, ethoxy, propoxy, and 1-methylethoxy. Specific examples of the "$C_{1-4}$ alkoxy" include butoxy, 1,1-dimethylethoxy, 1-methylpropoxy, and 2-methylpropoxy, in addition to those mentioned as the aforementioned specific examples of the "$C_{1-3}$ alkyl alkoxy". Specific examples of the "$C_{1-6}$ alkoxy" include pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, and hexyloxy, in addition to those mentioned as the aforementioned specific examples of the "$C_{1-4}$ alkyl alkoxy".

The term "$C_{3-7}$ alicyclic oxy" or "$C_{3-7}$ alicyclic oxy group" means a ($C_{3-7}$ alicyclic group)-O— group, and the $C_{3-7}$ alicyclic moiety is the same as the $C_{3-7}$ alicyclic group. The "$C_{3-7}$ alicyclic oxy group" encompasses a "$C_{3-7}$ cycloalkoxy group". The "cycloalkoxy group" means a "cycloalkyloxy", and the "cycloalkyl" moiety is the same as the aforementioned "cycloalkyl". Specific examples of the "$C_{3-7}$ alicyclic oxy group" include a cyclopropoxy group, a cyclobutoxy group, a cyclopentoxy group, and a cyclohexoxy group.

The $C_{6-10}$ aryl moiety in the "$C_{6-10}$ aryloxy group" is the same as the above $C_{6-10}$ aryl group. Examples of the "$C_{6-10}$ aryloxy group" preferably include a "$C_6$ or $C_{10}$ aryloxy group". Specific examples of the "$C_{6-10}$ aryloxy group" include, but are not limited to, a phenoxy group, a 1-naphthyloxy group, and a 2-naphthyloxy group.

The 5-membered or 6-membered heteroaryl moiety in the "5-membered or 6-membered heteroaryloxy group" is the same as the above "5-membered heteroaryl group" or "6-membered heteroaryl group". Specific examples of the "5-membered or 6-membered heteroaryloxy group" include, but are not limited to, a pyrazoyloxy group, a triazoyloxy group, a thiazoyloxy group, a thiadiazoyloxy group, a pyridyloxy group, and a pyridazoyloxy group.

The 4- to 10-membered non-aryl heterocyclic moiety in the "4- to 10-membered non-aryl heterocyclic oxy group" is the same as the above "4- to 10-membered non-aryl heterocycle". The "4- to 10-membered non-aryl heterocyclic oxy group" is preferably a "4- to 6-membered non-aryl heterocyclic oxy group". Specific examples of the "4- to 10-membered non-aryl heterocyclic oxy group" include, but are not limited to, a tetrahydrofuranyloxy group, a tetrahydropyranyloxy group, an azetidinyloxy group, a pyrrolidinyloxy group, and a piperidinyloxy group.

The $C_{1-6}$ alkyl moiety in the "$C_{1-6}$ alkylthio group" is the same as the above $C_{1-6}$ alkyl. The "$C_{1-6}$ alkylthio group" is preferably a "$C_{1-4}$ alkylthio group", and is more preferably a "$C_{1-3}$ alkylthio group". Specific examples of the "$C_{1-6}$ alkylthio group" include, but are not limited to, a methylthio group, an ethylthio group, a propylthio group, a butylthio group, an isopropylthio group, an isobutylthio group, a tert-butylthio group, a sec-butylthio group, an isopentylthio group, a neopentylthio group, a tert-pentylthio group, and a 1,2-dimethylpropylthio group.

The term "$C_{3-10}$ alicyclic thio" or "$C_{3-10}$ alicyclic thio group" means a ($C_{3-10}$ alicyclic group)-S— group, and the $C_{3-10}$ alicyclic moiety is the same as the above $C_{3-10}$ alicyclic group. The "$C_{3-10}$ alicyclic thio group" is preferably a "$C_{3-6}$ alicyclic thio group". Specific examples of the "$C_{3-6}$ alicyclic thio group" include, but are not limited to, a cyclopropoylthio group, a cyclobutylthio group, a cyclopentylthio group, and a cyclohexylthio group.

The $C_{6-10}$ aryl moiety in the "$C_{6-10}$ arylthio" or "$C_{6-10}$ arylthio group" is the same as the above $C_{6-10}$ aryl group. Examples of the "$C_{6-10}$ arylthio group" preferably include a "$C_6$ or $C_{10}$ arylthio group". Specific examples of the "$C_{6-10}$ aryloxy arylthio group" include, but are not limited to, a phenylthio group, a 1-naphthylthio group, and a 2-naphthylthio group.

The 5-membered or 6-membered heteroaryl moiety in the "5-membered or 6-membered heteroarylthio" or "5-membered or 6-membered heteroarylthio group" is the same as the above "5-membered heteroaryl group" or "6-membered heteroaryl group". Specific examples of the "5-membered or 6-membered heteroarylthio group" include, but are not limited to, a pyrazoylthio group, a triazoylthio group, a thiazoylthio group, a thiadiazoylthio group, a pyridylthio group, and a pyridazoylthio group.

The 4- to 10-membered non-aryl heterocyclic moiety in the "4- to 10-membered non-aryl heterocyclic thio" or "4- to 10-membered non-aryl heterocyclic thio group" is the same as the above "4- to 10-membered non-aryl heterocyclic group". The "4- to 10-membered non-aryl heterocyclic thio group" is preferably a "4- to 6-membered non-aryl heterocyclic thio group". Specific examples of the "4- to 10-membered non-aryl heterocyclic thio group" include, but are not limited to, a tetrahydropyranylthio group and a piperidinylthio group.

The term "$C_{1-6}$ alkylcarbonyl" or "$C_{1-6}$ alkylcarbonyl group" means a carbonyl group substituted with the above "$C_{1-6}$ alkyl group". The "$C_{1-6}$ alkylcarbonyl group" is preferably a "$C_{1-4}$ alkylcarbonyl group" or a "$C_{1-3}$ alkylcarbonyl group". Specific examples of the "$C_{1-6}$ alkylcarbonyl group" include, but are not limited to, an acetyl group, a propionyl group, and a butyryl group.

The term "$C_{1-6}$ alkoxycarbonyl" or "$C_{1-6}$ alkoxycarbonyl group" means a carbonyl group substituted with the above "$C_{1-6}$ alkoxy group". The "$C_{1-6}$ alkoxycarbonyl group" is preferably a "$C_{1-4}$ alkoxycarbonyl group" or a "$C_{1-3}$ alkoxycarbonyl group". Specific examples of the "$C_{1-6}$ alkoxycarbonyl group" include, but are not limited to, a methoxycarbonyl group, an ethoxycarbonyl group, a propoxycarbonyl group, and a butoxycarbonyl group.

The term "$C_{3-10}$ alicyclic carbonyl" or "$C_{3-10}$ alicyclic carbonyl group" means a carbonyl group substituted with the above "$C_{3-10}$ alicyclic group". The "$C_{3-10}$ alicyclic carbonyl group" is preferably a "$C_{3-6}$ alicyclic carbonyl group". Specific examples of the "$C_{3-10}$ alicyclic carbonyl group" include, but are not limited to, a cyclopropoylcarbonyl group and a cyclopentylcarbonyl group.

The term "$C_{6-10}$ arylcarbonyl" or "$C_{6-10}$ arylcarbonyl group" means a carbonyl group substituted with the above "$C_{6-10}$ aryl group". The "$C_{6-10}$ arylcarbonyl group" is preferably a "$C_6$ or $C_{10}$ arylcarbonyl group". Specific examples of the "$C_{6-10}$ arylcarbonyl group" include, but are not limited to, a benzoyl group, a 1-naphthylcarbonyl group, and a 2-naphthylcarbonyl group.

The term "5-membered or 6-membered heteroarylcarbonyl" or "5-membered or 6-membered heteroarylcarbonyl group" means a carbonyl group substituted with the above "5-membered or 6-membered heteroaryl group". Specific examples of the "5-membered or 6-membered heteroarylcarbonyl group" include, but are not limited to, a pyrazoylcarbonyl group, a triazoylcarbonyl group, a thiazoylcarbonyl group, a thiadiazoylcarbonyl group, a pyridylcarbonyl group, and a pyridazoylcarbonyl group.

The "4- to 10-membered non-aryl heterocyclic carbonyl" or "4- to 10-membered non-aryl heterocyclic carbonyl group" means a carbonyl group substituted with the above "4- to 10-membered non-aryl heterocyclic group". The "4- to 10-membered non-aryl heterocyclic carbonyl group" is preferably a "4- to 6-membered non-aryl heterocyclic carbonyl group". Specific examples of the "4- to 10-membered non-aryl heterocyclic carbonyl group" include, but are not limited to, an azetidinylcarbonyl group, a pyrrolidinylcarbonyl group, a piperidinylcarbonyl group, and a morpholinylcarbonyl group.

The term "$C_{1-6}$ alkylsulfonyl" or "$C_{1-6}$ alkylsulfonyl group" means a sulfonyl group substituted with the above "$C_{1-6}$ alkyl group". The "$C_1$-6 alkylsulfonyl group" is preferably a "$C_{1-4}$ alkylsulfonyl group". Specific examples of the "$C_{1-6}$ alkylsulfonyl group" include, but are not limited to, a methylsulfonyl group, a propionylsulfonyl group, and a butyrylsulfonyl group.

The term "$C_{3-10}$ alicyclic sulfonyl" or "$C_{3-10}$ alicyclic sulfonyl group" means a sulfonyl group substituted with the above "$C_{3-10}$ alicyclic group". The "$C_{3-10}$ alicyclic sulfonyl group" is preferably a "$C_{3-6}$ alicyclic sulfonyl group". Specific examples of the "$C_{3-10}$ alicyclic sulfonyl group" include, but are not limited to, a cyclopropoylsulfonyl group, a cyclobutylsulfonyl group, a cyclopentylsulfonyl group, and a cyclohexylsulfonyl group.

The term "$C_{6-10}$ arylsulfonyl" or "$C_{6-10}$ arylsulfonyl group" means a sulfonyl group substituted with the above "$C_{6-10}$ aryl group". The "$C_{6-10}$ arylsulfonyl group" is preferably a "$C_6$ or $C_{10}$ arylsulfonyl group". Specific examples of the "$C_{6-10}$ arylsulfonyl group" include, but are not limited to, a phenylsulfonyl group, a 1-naphthylsulfonyl group, and a 2-naphthylsulfonyl group.

The term "5-membered or 6-membered heteroarylsulfonyl" or "5-membered or 6-membered heteroarylsulfonyl group" means a sulfonyl group substituted with the above "5-membered or 6-membered heteroaryl group". Specific examples of the "5-membered or 6-membered heteroarylsulfonyl group" include, but are not limited to, a pyrazoylsulfonyl group, a triazoylsulfonyl group, a thiazoylsulfonyl group, a thiadiazoylsulfonyl group, a pyridylsulfonyl group, and a pyridazoylsulfonyl group.

In the compound of the present disclosure represented by formula (1) or formula (2), the preferred $R^1$, $R^2$, $R^3$, $R^4$, $R^5$, $R^6$, $R^7$, $R^8$, $R^9$, $R^{10}$, $R^{11}$, $R^{12}$, in, n, $L^1$, $L^2$, Q, X, and Y are as follows, but the technical scope of the present disclosure is not limited to the range of compounds listed below.

Examples of the preferred aspect of $R^1$ include a hydrogen atom.

Examples of the preferred aspect of $R^2$ include a methoxy group.

Examples of the preferred aspect of $R^3$ include a hydrogen atom.

Examples of the preferred aspect of $R^4$ include a $C_{1-6}$ alkyl group, a $C_{3-7}$ alicyclic group, or a $C_{6-10}$ aryl group (the $C_{1-6}$ alkyl group, $C_{3-7}$ alicyclic group, and $C_{6-10}$ aryl group are optionally substituted with one to three substituents that are the same or different, selected from the group consisting of a fluorine atom, a chlorine atom, a $C_{1-6}$ alkyl group, a $C_{3-7}$ alicyclic group, a $C_{6-10}$ aryl group, a 5-membered or 6-membered heteroaryl group, and a 4- to 10-membered non-aryl heterocyclic group).

Examples of the more preferred aspect of $R^4$ include a methyl group, an ethyl group, an isopropyl group, a cyclohexyl group, a cyclohexylmethyl group, a phenyl group, or a benzyl group (the methyl group, ethyl group, isopropyl group, cyclohexyl group, cyclohexylmethyl group, phenyl group, and benzyl group are optionally substituted with one to three substituents that are the same or different, selected from the group consisting of a fluorine atom, a chlorine atom, and a $C_{1-6}$ alkyl group).

Examples of the still more preferred aspect of $R^4$ include a methyl group, an ethyl group, an isopropyl group, a cyclohexyl group, or a phenyl group (the methyl group, ethyl group, isopropyl group, cyclohexyl group, and phenyl group are optionally substituted with one to three substituents that are the same or different, selected from the group consisting of a fluorine atom, a chlorine atom, and a $C_{1-6}$ alkyl group).

Examples of the preferred aspect of $R^5$, $R^6$, and $R^7$ include a hydrogen atom, a $C_{3-6}$ alicyclic group, or a $C_{1-6}$ alkyl group (the $C_{3-6}$ alicyclic group and $C_{1-6}$ alkyl group are optionally substituted with one to three substituents that are the same or different, selected from the group consisting of a halogen atom, a hydroxyl group, a $C_{1-6}$ alkoxy group, a $C_{3-10}$ alicyclic group, a $C_{6-10}$ aryl group, and a 4- to 6-membered non-aryl heterocyclic group).

Examples of the preferred aspect of $R^8$, $R^9$, and $R^{10}$ include a hydrogen atom, a halogen atom, a cyano group, a $C_{1-6}$ alkylsulfonyl group, a $C_{1-6}$ alkyl group, or a $C_{1-6}$ alkoxy group.

Examples of the preferred aspect of $R^{11}$ include a hydrogen atom, a $C_{1-3}$ alkyl group, a formyl group, a $C_{1-3}$ alkylcarbonyl group, a $C_{1-4}$ alkoxycarbonyl group, or a $C_{6-10}$ arylcarbonyl group (the $C_{1-3}$ alkyl group, $C_{1-3}$ alkylcarbonyl group, $C_{1-4}$ alkoxycarbonyl group, and $C_{6-10}$ arylcarbonyl group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group).

Examples of the preferred aspect of $R^2$ include a hydrogen atom or a $C_{1-3}$ alkyl group (the $C_{1-3}$ alkyl group is optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl, and a 5-membered or 6-membered heteroaryloxy group).

Examples of the preferred aspect of in include 1 or 2.

Examples of the more preferred aspect of in include 1.

Examples of the preferred aspect of n include 0, 1, 2, or 3.

Examples of the more preferred aspect of n include 0, 1, or 2.

Examples of the still more preferred aspect of n include 0 or 1.

Examples of the preferred aspect of $L^1$ include —NH—C(═O)—, —C(═O)—NH—, —NH—C(═S)—, —C(═S)—NH—, —NH—C(═O)—$CH_2$—, —C(═O)—NH—$CH_2$—, —NH—C(═O)—$CH_2$—$CH_2$—, —C(═O)—NH—$CH_2$—$CH_2$—, —NH—C(═O)—O—, or —O—C(═O)—NH—.

Examples of the more preferred aspect of $L^1$ include —NH—C(═O)— or —C(═O)—NH—.

Examples of the preferred aspect of $L^2$ include a single bond.

Examples of the preferred aspect of Q include a single bond.

Examples of the preferred aspect of X include a $C_{6-10}$ aryl group or a 5- to 10-membered heteroaryl group (the $C_{6-10}$ aryl group and 5- to 10-membered heteroaryl group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group).

Examples of the more preferred aspect of X include a phenyl group or a 6-membered heteroaryl group (the phenyl group and 6-membered heteroaryl group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group).

Examples of the still more preferred aspect of X include the following formulas (A1), (A2), and (A3):

[Chemical Formula 26]

(A1)

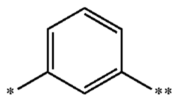

(A2)

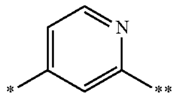

(A3)

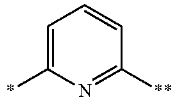

wherein * represents a bonding position with $L^1$ and ** represents a bonding position with Q or Y.

Examples of the preferred aspect of Y include a $C_{6-10}$ aryl group, a 5- to 10-membered heteroaryl group, or a $C_{3-7}$ alicyclic group (the $C_{6-10}$ aryl group, 5- to 10-membered heteroaryl group, and $C_{3-7}$ alicyclic group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group).

Examples of the more preferred aspect of Y include a phenyl group or a cyclohexyl group (the phenyl group and cyclohexyl group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group).

Examples of the still more preferred aspect of Y include the following formulas (B) and (C):

[Chemical Formula 27]

(B)

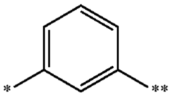

(C)

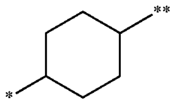

wherein * represents a bonding position with X or Q and ** represents a bonding position with $L^2$ or the oxygen atom.

One aspect of the compound represented by formula (1) may be (A) below.

(A) A compound or pharmaceutically acceptable salt thereof, wherein:

$R^1$ is a hydrogen atom;

$R^2$ is a methoxy group;

$R^3$ is a hydrogen atom;

$R^4$ is a $C_{1-6}$ alkyl group, a $C_{3-7}$ alicyclic group, or a $C_{6-10}$ aryl group (the $C_{1-6}$ alkyl group, $C_{3-7}$ alicyclic group, and $C_{6-10}$ aryl group are optionally substituted with one to three substituents that are the same or different, selected from the group consisting of a fluorine atom, a chlorine atom, a $C_{1-6}$ alkyl group, a $C_{3-7}$ alicyclic group, a $C_{6-10}$ aryl group, a 5-membered or 6-membered heteroaryl group, and a 4- to 10-membered non-aryl heterocyclic group);

m is 0, 1, or 2;

n is 0, 1, 2, or 3;

$L^1$ is —NH—C(═O)—, —C(═O)—NH—, —NH—C(═S)—, —C(═S)—NH—, —NH—C(═O)—$CH_2$—, —C(═O)—NH—$CH_2$—, —NH—C(═O)—$CH_2$—$CH_2$—, —C(═O)—NH—$CH_2$—$CH_2$—, —NH—C(═O)—O—, or —O—C(═O)—NH—;

$L^2$ is a single bond or an optionally substituted $C_{1-6}$ alkyl group;

Q is a single bond;

X is a $C_{6-10}$ aryl group or a 5- to 10-membered heteroaryl group (the $C_{6-10}$ aryl group and 5- to 10-membered heteroaryl group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group);

Y is a $C_{6-10}$ aryl group, a 5- to 10-membered heteroaryl group, or a $C_{3-7}$ alicyclic group (the $C_{6-10}$ aryl group, 6-membered heteroaryl group, and $C_{3-7}$ alicyclic group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group); and X and Y are bonded at a carbon atom on each ring.

One aspect of the compound represented by formula (1) may be (B) below.

(B) A compound or pharmaceutically acceptable salt thereof, wherein:

$R^1$ is a hydrogen atom;

$R^2$ is a methoxy group;

$R^3$ is a hydrogen atom;

$R^4$ is a $C_{1-6}$ alkyl group, a $C_{3-7}$ alicyclic group, or a $C_{6-10}$ aryl group (the $C_{1-6}$ alkyl group, $C_{3-7}$ alicyclic group, and $C_{6-10}$ aryl group are optionally substituted with one to three substituents that are the same or different, selected from the group consisting of a fluorine atom, a chlorine atom, a $C_{1-6}$ alkyl group, a $C_{3-7}$ alicyclic group, a $C_{6-10}$ aryl group, a 5-membered or 6-membered heteroaryl group, and a 4- to 10-membered non-aryl heterocyclic group);

in is 1 or 2;

n is 0, 1, 2, or 3;

$L^1$ is —NH—C(═O)— or —C(═O)—NH—;

$L^2$ is a single bond;

Q is a single bond;

X is a $C_{6-10}$ aryl group or a 5- to 10-membered heteroaryl group (the $C_{6-10}$ aryl group and 5- to 10-membered heteroaryl group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group);

Y is a $C_{6-10}$ aryl group, a 5- to 10-membered heteroaryl group, or a $C_{3-7}$ alicyclic group (the $C_{6-10}$ aryl group, 5- to 10-membered heteroaryl group, and $C_{3-7}$ alicyclic group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group); and X and Y are bonded at a carbon atom on each ring.

One aspect of the compound represented by formula (1) may be (C) below.

(C) A compound or pharmaceutically acceptable salt thereof, wherein:

$R^1$ is a hydrogen atom;

$R^2$ is a methoxy group;

$R^3$ is a hydrogen atom;

$R^4$ is a $C_{1-6}$ alkyl group, a $C_{3-7}$ alicyclic group, or a $C_{6-10}$ aryl group (the $C_{1-6}$ alkyl group, $C_{3-7}$ alicyclic group, and $C_{6-10}$ aryl group are optionally substituted with one to three substituents that are the same or different, selected from the group consisting of a fluorine atom, a chlorine atom, a $C_{1-6}$ alkyl group, a $C_{3-7}$ alicyclic group, a $C_{6-10}$ aryl group, a 5-membered or 6-membered heteroaryl group, and a 4- to 10-membered non-aryl heterocyclic group);

m is 1;

n is 0, 1, 2, or 3;

$L^1$ is —NH—C(═O)— or —C(═O)—NH—;

$L^2$ is a single bond;

Q is a single bond;

X is a phenyl group or a 6-membered heteroaryl group (the phenyl group and 6-membered heteroaryl group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group);

Y is a phenyl group or a cyclohexyl group (the phenyl group and cyclohexyl group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group); and X and Y are bonded at a carbon atom on each ring.

One aspect of the compound represented by formula (1) may be (D) below.

(D) A compound or pharmaceutically acceptable salt thereof, wherein:

$R^1$ is a hydrogen atom;

$R^2$ is a methoxy group;

$R^3$ is a hydrogen atom;

$R^4$ is a $C_{1-6}$ alkyl group, a $C_{3-7}$ alicyclic group, or a $C_{6-10}$ aryl group (the $C_{1-6}$ alkyl group, $C_{3-7}$ alicyclic group, and $C_{6-10}$ aryl group are optionally substituted with one to three substituents that are the same or different, selected from the group consisting of a fluorine atom, a chlorine atom, a $C_{1-6}$ alkyl group, a $C_{3-7}$ alicyclic group, a $C_{6-10}$ aryl group, a 5-membered or 6-membered heteroaryl group, and a 4- to 10-membered non-aryl heterocyclic group);

m is 1;

n is 0, 1, 2, or 3;

$L^1$ is —NH—C(═O)— or —C(═O)—NH—;

$L^2$ is a single bond;

Q is a single bond;

X is a phenyl group or a pyridyl group (the phenyl group and pyridyl group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_{3-10}$ alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group);

Y is a phenyl group or a cyclohexyl group (the phenyl group and cyclohexyl group are optionally substituted with one to three substituents that are the same or different, selected from the group consisting of a halogen atom, a hydroxyl group, a cyano group, a $C_{1-6}$ alkyl group, a $C_{1-6}$ alkylsulfonyl group, a $C_{1-6}$ alkoxy group, a $C_{3-7}$ alicyclic group, a $C_3$-10 alicyclic oxy group, a $C_{6-10}$ aryl group, a 4- to 10-membered non-aryl heterocyclic group, a 4- to 10-membered non-aryl heterocyclic oxy group, a $C_{6-10}$ aryloxy group, a 5-membered or 6-membered heteroaryl group, and a 5-membered or 6-membered heteroaryloxy group); and X and Y are bonded at a carbon atom on each ring.

One aspect of the compound represented by formula (1) may be (E) below.

(E) A compound or pharmaceutically acceptable salt thereof, wherein:

$R^1$ is a hydrogen atom;

$R^2$ is a methoxy group;

$R^3$ is a hydrogen atom;

$R^4$ is a $C_{1-6}$ alkyl group, a $C_{3-7}$ alicyclic group, or a $C_{6-10}$ aryl group (the $C_{1-6}$ alkyl group, $C_{3-7}$ alicyclic group, and $C_{6-10}$ aryl group are optionally substituted with one to three substituents that are the same or different, selected from the group consisting of a fluorine atom, a chlorine atom, a $C_{1-6}$ alkyl group, a $C_{3-7}$ alicyclic group, a $C_{6-10}$ aryl group, a 5-membered or 6-membered heteroaryl group, and a 4- to 10-membered non-aryl heterocyclic group);

m is 1;

n is 0, 1, 2, or 3;

$L^1$ is —NH—C(═O)— or —C(═O)—NH—;

$L^2$ is a single bond;

Q is a single bond;

X is the following formula (A):

[Chemical Formula 28]

(A)

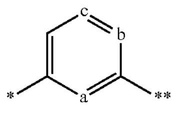

wherein * represents a bonding position with $L^1$ and ** represents a bonding position with Y;

a is $CR^8$ or N;

b is $CR^9$ or N;

c is $CR^{10}$ or N;

$R^8$, $R^9$, and $R^{10}$ are each independently a hydrogen atom, a halogen atom, a cyano group, a $C_{1-6}$ alkylsulfonyl group, a $C_{1-6}$ alkyl group, or a $C_{1-6}$ alkoxy group; and Y is the following formula (B) or (C):

[Chemical Formula 29]

(B)

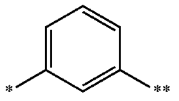

(C)

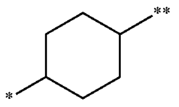

wherein * represents a bonding position with X and ** represents a bonding position with the oxygen atom.

One aspect of the compound represented by formula (1) may be (F) below.

(F) A compound or pharmaceutically acceptable salt thereof, wherein:

$R^1$ is a hydrogen atom;

$R^2$ is a methoxy group;

$R^3$ is a hydrogen atom;

$R^4$ is a methyl group, an ethyl group, an isopropyl group, a cyclohexyl group, a cyclohexylmethyl group, a phenyl group, or a benzyl group (the methyl group, ethyl group, isopropyl group, cyclohexyl group, cyclohexylmethyl group, phenyl group, and benzyl group are optionally substituted with one to three substituents that are the same or different, selected from the group consisting of a fluorine atom, a chlorine atom, and a $C_{1-6}$ alkyl group);

m is 1;

n is 0, 1, 2, or 3;

$L^1$ is —NH—C(═O)— or —C(═O)—NH—;

$L^2$ is a single bond;

Q is a single bond;

X is the following formula (A1), (A2), or (A3):

[Chemical Formula 30]

(A1)

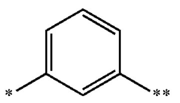

(A2)

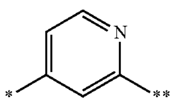

(A3)

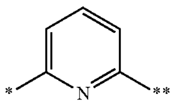

wherein * represents a bonding position with $L^1$ and ** represents a bonding position with Y; and Y is the following formula (B) or (C):

[Chemical Formula 31]

(B)

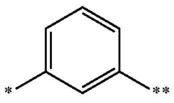

(C)

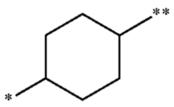

wherein * represents a bonding position with X and ** represents a bonding position with the oxygen atom.

One aspect of the compound represented by formula (1) may be (G) below.

(G) A compound or pharmaceutically acceptable salt thereof, wherein:

$R^1$ is a hydrogen atom;

$R^2$ is a methoxy group;

$R^3$ is a hydrogen atom;

$R^4$ is a methyl group, an ethyl group, an isopropyl group, a cyclohexyl group, or a phenyl group (the methyl group, ethyl group, isopropyl group, cyclohexyl group, and phenyl group are optionally substituted with one to three substituents that are the same or different, selected from the group consisting of a fluorine atom, a chlorine atom, and a $C_{1-6}$ alkyl group);

m is 1;

n is 0, 1, 2, or 3;

$L^1$ is —NH—C(═O)— or —C(═O)—NH—;

$L^2$ is a single bond;

Q is a single bond;

X is the following formula (A1), (A2), or (A3):

[Chemical Formula 32]

(A1)

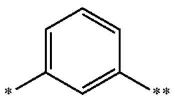

(A2)

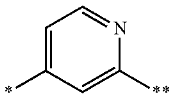

(A3)

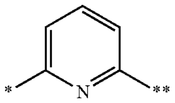

wherein * represents a bonding position with $L^1$ and ** represents a bonding position with Y; and Y is the following formula (B) or (C):

[Chemical Formula 33]

(B)

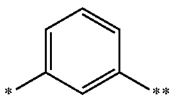

-continued (C)

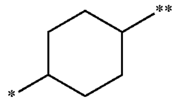

wherein * represents a bonding position with X and ** represents a bonding position with the oxygen atom.

Examples of the "pharmaceutically acceptable salt" include acid addition salts and base addition salts. Examples of the acid addition salt include inorganic acid salts such as hydrochloride salt, hydrobromide salt, sulfate salt, hydroiodide salt, nitrate salt, and phosphate salt, or organic acid salts such as citrate salt, oxalate salt, phthalate salt, fumarate salt, maleate salt, succinate salt, malate salt, acetate salt, formate salt, propionate salt, benzoate salt, trifluoroacetate salt, methanesulfonate salt, benzenesulfonate salt, p-toluenesulfonate salt, and camphorsulfonate salt. In addition, examples of the base addition salt include inorganic base salts such as sodium salt, potassium salt, calcium salt, magnesium salt, barium salt, and aluminum salt, or organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine, and N,N-dibenzylethylamine. Furthermore, examples of the "pharmaceutically acceptable salt" include amino acid salts with basic amino acids or acidic amino acids such as arginine, lysine, ornithine, aspartic acid, or glutamic acid.

Suitable salts of raw material compounds and intermediates and salts acceptable as pharmaceutical raw materials are common non-toxic salts, and for these, in addition to acid addition salts such as organic acid salts (for example, acetate salt, trifluoroacetate salt, maleate salt, fumarate salt, citrate salt, tartrate salt, methanesulfonate salt, benzenesulfonate salt, formate salt, p-toluenesulfonate salt or the like) and inorganic acid salts (for example, hydrochloride salt, hydrobromide salt, hydroiodide salt, sulfate salt, nitrate salt, phosphate salt or the like), salts with amino acids (for example, arginine, aspartic acid, glutamic acid or the like), metal salts such as alkali metal salts (for example, sodium salt, potassium salt or the like) and alkaline earth metal salts (for example, calcium salt, magnesium salt or the like), ammonium salts, organic base salts (for example, trimethylamine salt, triethylamine salt, pyridine salt, picoline salt, dicyclohexylamine salt, N,N'-dibenzylethylenediamine salt or the like), those skilled in the art can appropriately select salts.

When it is desired to acquire a salt of the compound of the present invention, if the compound of the present invention is obtained in the form of salt, it may be purified as it is, or alternatively, if the compound of the present invention is obtained in the free form, it may be dissolved or suspended in an appropriate organic solvent, to which an acid or base is added to form a salt by a normal method.

In the present invention, a deuterated product in which any one or two or more 1H of the compound represented by formula (1) are converted into 2H(D) is also encompassed in the compound represented by formula (1).

A compound represented by formula (1) or pharmaceutically acceptable salt thereof is included in the present invention. In addition, the compound of the present invention may be present in the form of hydrate and/or solvate with various solvents (ethanolate and the like), and these hydrate and/or solvate are also included in the compound of the present invention. Furthermore, all tautomers, all stereoisomers present, and all modes of crystal form of the compound (1) of the present invention, as well as mixtures thereof, are also included in the present invention.

Among the compound (1) of the present invention, some may have optical isomers based on the optically active center, atropisomers based on axial or planar chirality caused by restraint of intramolecular rotation, and the other stereoisomers, tautomers, geometrical isomers, and the like, and all possible isomers including the above and mixtures thereof are encompassed within the scope of the present invention.

In particular, optical isomers and atropisomers can be obtained as racemate, or alternatively, can be obtained as optically active substances when optically active starting materials or intermediates are used. If necessary, at an appropriate stage in the following production methods, corresponding raw material, intermediate, or racemate, the final product, can be resolved into optical enantiomers thereof physically or chemically through known separation methods such as a method using an optically active column and fractional crystallization method. Specifically, for example, in the diastereomer method, two diastereomers are formed from racemate through a reaction using an optically active resolving agent. In general, these different diastereomers have different physical properties, and thus, can be resolved by known methods such as fractional crystallization.

Hereinafter, methods for producing the compound of the present disclosure will be described, but the method for producing the compound of the present disclosure is not limited to them.

The compound of the present disclosure can be produced by, for example, the production methods described below, without being limited to them. These production methods can be appropriately modified based on the knowledge of those skilled in organic synthetic chemistry. In the following production methods, compounds used as raw materials may be used in the form of salt thereof, as long as it does not interfere with the reaction.

In the following production methods, even if the use of a protecting group is not specifically stated, when any functional group other than the reaction point is changed under the reaction conditions, or when it is inappropriate to perform post-reaction treatment, the target compound can be obtained by protecting the functional group other than the reaction point as necessary and deprotecting it after the reaction is terminated or after a series of reactions is carried out. As the protecting groups used in these processes, the normal protecting groups described in the literature (T. W. Greene and P. G. M. Wuts, "Protective Group in Organic Synthesis", $3^{rd}$ Ed., John Wiley and Sons, Inc., New York (1999)) and the like can be used. In addition, the introduction and removal of protecting groups can be carried out by methods conventionally used in organic synthetic chemistry (for example, methods described in the above literature and the like) or by other methods similar thereto.

The starting raw materials and intermediates in the following production methods can be purchased as commercial products, or are available by synthesizing them in accordance with the methods described in known literature or from known compounds in accordance with known methods. In addition, these starting raw materials and intermediates may be used in the form of salt thereof, as long as it does not interfere with the reaction.

The intermediates and target compounds in the following production methods can also be converted to other compounds included in the present disclosure by converting their functional groups as appropriate. The conversion of functional groups at that time can be carried out by methods conventionally used in organic synthetic chemistry (for example, the methods described in R. C. Larock, “Comprehensive Organic Transformations”, $2^{nd}$ Ed., John Wiley and Sons, Inc., New York (1999) and the like) or by other methods similar thereto.

The inert solvent in the following production methods means a solvent that does not react with the raw materials, reagents, bases, acids, catalysts, ligands, and the like used in the reaction (hereinafter, may also be referred to as “raw materials and the like used in the reaction”). Also, even when the solvent used in each step reacts with the raw materials and the like used in the reaction, it can be used as the inert solvent as long as the desired reaction proceeds and the target compound is obtained.

The compound of the present disclosure represented by formula (1) can be produced by, for example, the following production methods 1 to 5.

Production Method 1

Among the compounds represented by formula (1), a compound represented by formula [A1] can be produced by, for example, the production method below.

(In the formula, $R^{41}$ and $R^{42}$ are each $R^4$, which is the same or different; $L^3$ is —NH—C(=O)— or —C(=O)—NH—; and $R^2$, $R^3$, $R^4$, X, and Y are the same as in item 1.)

Step 1-1: Condensation Reaction

Compound a5 is produced by allowing compound a1 to react with compound a2 in an appropriate solvent in the presence of or in the absence of various condensing agents and/or bases. As the condensing agent, various condensing agents used in conventional methods can be used, and examples thereof preferably include propylphosphonic acid anhydride or 1-ethyl-3-(3-dimethylaminopropyl)carbodiimide (including hydrochloride). The base is appropriately selected from the bases and the like listed below, and examples thereof preferably include diisopropylethylamine or triethylamine. The solvent is appropriately selected from the solvents and the like listed below, and examples thereof preferably include tetrahydrofuran, dimethylformamide, or chloroform. The reaction time is normally 5 minutes to 72 hours, and is preferably 30 minutes to 24 hours. The reaction temperature is normally 0° C. to 200° C., and is preferably 0° C. to 100° C.

[Chemical Formula 34]

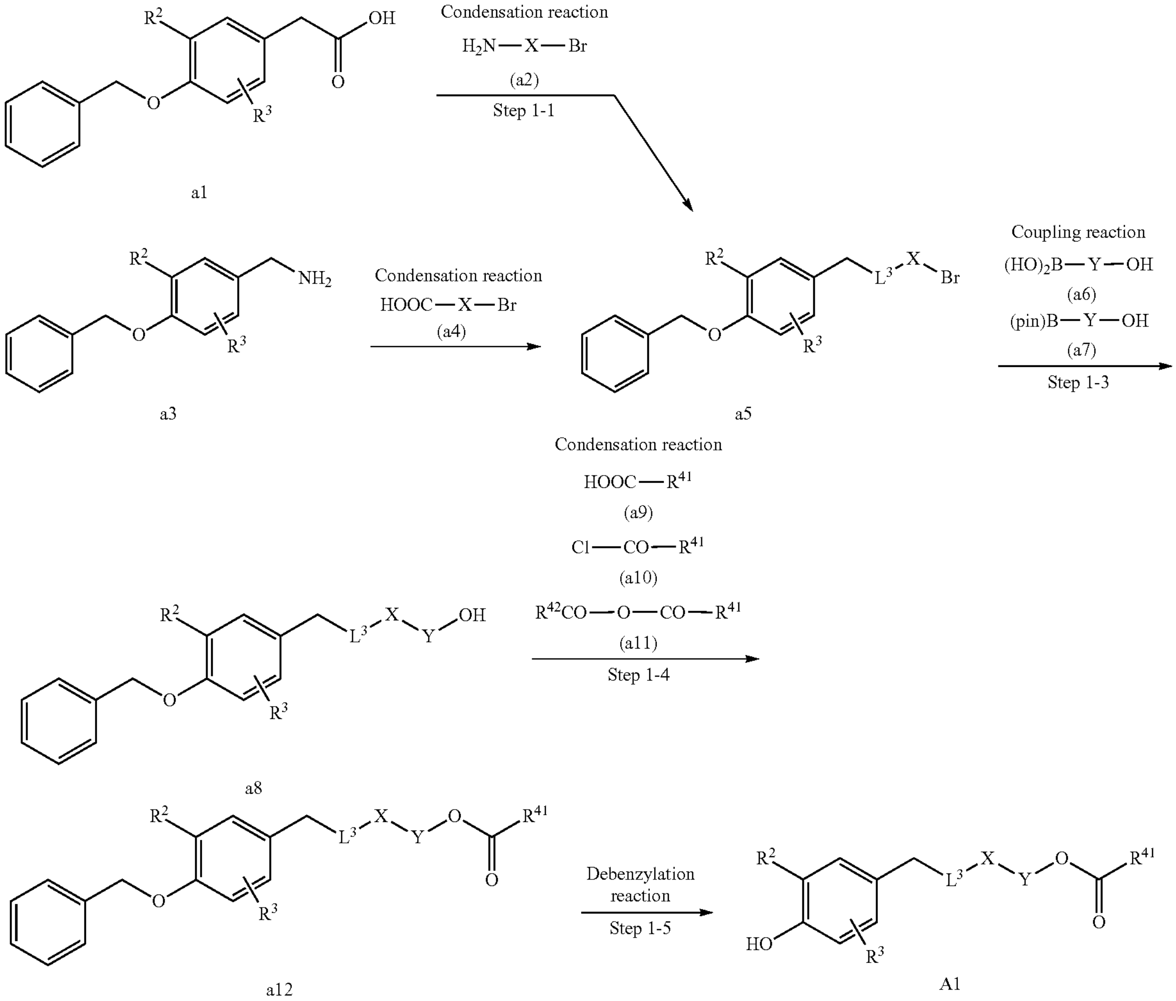

Step 1-2: Condensation Reaction

Compound a5 is produced by allowing compound a3 to react with compound a4 in an appropriate solvent in the presence of or in the absence of various condensing agents and/or bases. As the condensing agent, various condensing agents used in conventional methods can be used, and examples thereof preferably include propylphosphonic acid anhydride or 1-ethyl-3-(3-dimethylaminopropyl)carbodiimide (including hydrochloride). The base is appropriately selected from the bases and the like listed below, and examples thereof preferably include diisopropylethylamine or triethylamine. The solvent is appropriately selected from the solvents and the like listed below, and examples thereof preferably include tetrahydrofuran, dimethylformamide, or chloroform. The reaction time is normally 5 minutes to 72 hours, and is preferably 30 minutes to 24 hours. The reaction temperature is normally 0° C. to 200° C., and is preferably 0° C. to 100° C.

Step 1-3: Coupling Reaction

Compound a8 is produced by coupling compound a5 with compound a6 or a7 in the presence of a catalyst and a base. Examples of the catalyst include transition metals such as palladium, salts thereof, complexes thereof, and supports such as polymers having them supported thereon. The base is appropriately selected from the bases and the like listed below, and examples thereof preferably include sodium carbonate and potassium carbonate. The solvent is appropriately selected from the solvents and the like listed below, and examples thereof preferably include a mixed solvent of 1,2-dimethoxyethane and water. The reaction time is normally 5 minutes to 72 hours, and is preferably 30 minutes to 24 hours. The reaction temperature is normally 0° C. to 200° C., and is preferably 20° C. to 150° C. The reaction temperature is normally 0° C. to 200° C., and is preferably 0° C. to 100° C.

Step 1-4: Condensation Reaction

Compound a12 is produced by allowing compound a8 to react with compound a9, a10, or a11 in an appropriate solvent in the presence of or in the absence of various condensing agents and/or bases. As the condensing agent, various condensing agents used in conventional methods can be used, and examples thereof preferably include 1-ethyl-3-(3-dimethylaminopropyl)carbodiimide (including hydrochloride). The base is appropriately selected from the bases and the like listed below, and examples thereof preferably include diisopropylethylamine or triethylamine. The solvent is appropriately selected from the solvents and the like listed below, and examples thereof preferably include tetrahydrofuran, dimethylformamide, or chloroform. The reaction time is normally 5 minutes to 72 hours, and is preferably 30 minutes to 24 hours. The reaction temperature is normally 0° C. to 200° C., and is preferably 0° C. to 100° C.

Step 1-5: Debenzylation Reaction

Compound A1 is produced by reducing compound a12 in the presence of a catalyst. As the reducing agent, hydrogen, salts of formic acid such as ammonium formate, and hydrazine can be used, for example. Examples of the catalyst include transition metals such as palladium, nickel, rhodium, cobalt, and platinum, salts thereof, complexes thereof, and supports such as polymers having them supported thereon. The solvent is appropriately selected from the solvents and the like listed below, and examples thereof preferably include ethyl acetate, ethanol, or methanol. The reaction time is normally 5 minutes to 72 hours, and is preferably 30 minutes to 24 hours. The reaction temperature is normally 0° C. to 200° C., and is preferably 0° C. to 100° C.

Compound a1 used can be any of those commercially available, or can be produced in accordance with known methods, such as the method described in ACS Chem Neurosci. 2018, 9, 587-602.

Compound a3 used can be any of those commercially available, or can be produced in accordance with known methods, such as the method described in Nature Commun. 2018, 9, 4123.

Production Method 2

Among the compounds represented by formula (1), a compound represented by formula [A2] can be produced by, for example, the production method below.

[Chemical Formula 35]

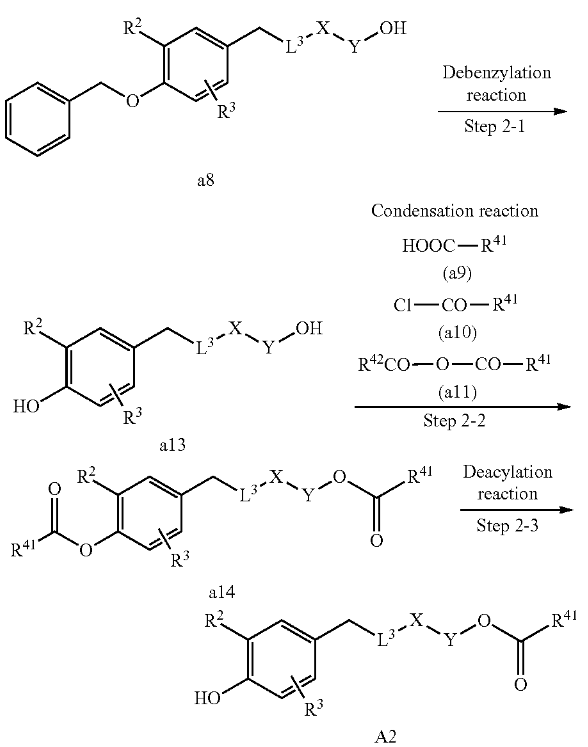

a8 a13 a14

A2

(In the formula, $R^{41}$ and $R^{42}$ are each $R^4$, which is the same or different; $L^3$ is —NH—C(═O)— or —C(═O)—NH—; and $R^2$, $R^3$, $R^4$, X, and Y are the same as in item 1.)

Step 2-1: Debenzylation Reaction

Compound a13 is produced by reducing compound a8 in the presence of a catalyst. As the reducing agent, hydrogen, salts of formic acid such as ammonium formate, and hydrazine can be used, for example. Examples of the catalyst include transition metals such as palladium, nickel, rhodium, cobalt, and platinum, salts thereof, complexes thereof, and supports such as polymers having them supported thereon. The solvent is appropriately selected from the solvents and the like listed below, and examples thereof preferably include ethyl acetate, ethanol, or methanol. The reaction time is normally 5 minutes to 72 hours, and is preferably 30 minutes to 24 hours. The reaction temperature is normally 0° C. to 200° C., and is preferably 0° C. to 100° C.

Step 2-2: Condensation Reaction

Compound a14 is produced by allowing compound a13 to react with compound a9, a10, or all in an appropriate solvent in the presence of or in the absence of various condensing agents and/or bases. As the condensing agent, various condensing agents used in conventional methods can be used, and examples thereof preferably include propylphosphonic acid anhydride or 1-ethyl-3-(3-dimethylaminopropyl)carbodiimide (including hydrochloride). The base is appropriately selected from the bases and the like listed below, and examples thereof preferably include diisopropylethylamine or triethylamine. The solvent is appropriately selected from the solvents and the like listed below, and examples thereof preferably include tetrahydrofuran, dimethylformamide, or chloroform. The reaction time is normally 5 minutes to 72 hours, and is preferably 30 minutes to 24 hours. The reaction temperature is normally 0° C. to 200° C., and is preferably 0° C. to 100° C.

Step 2-3: Deacylation Reaction

Compound A2 is produced by allowing compound a14 to react with various bases in an appropriate solvent. The base is appropriately selected from the bases and the like listed below, and examples thereof preferably include ammonia. The solvent is appropriately selected from the solvents and the like listed below, and examples thereof preferably include 2-propanol or tetrahydrofuran. The reaction time is normally 5 minutes to 72 hours, and is preferably 30 minutes to 24 hours. The reaction temperature is normally 0° C. to 200° C., and is preferably 0° C. to 100° C.

Production Method 3

The compound represented by formula [a13] can be produced by, for example, the following production method.

[Chemical Formula 36]

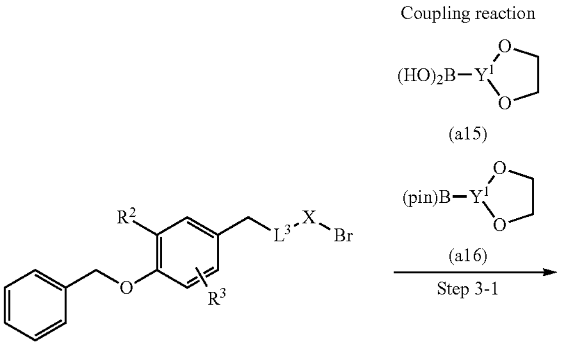

a5

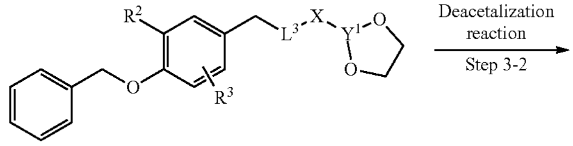

a17

-continued

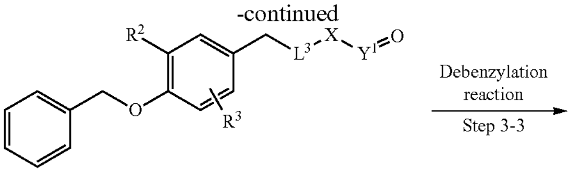

a18

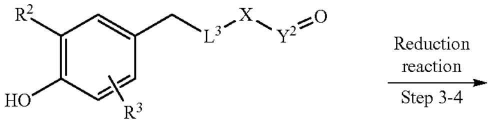

a19

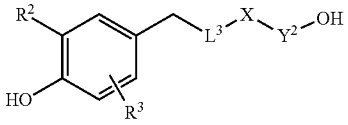

a13

(In the formula, $Y^1$ is a $C_{3-10}$ alicyclic group having an unsaturated bond; $Y^2$ is a $C_{3-10}$ alicyclic group; $L^3$ is —NH—C(=O)— or —C(=O)—NH—; $R^2$, $R^3$, and X are the same as in item 1; and a15, a16, and a17 represent compounds in which the carbonyl group on $Y^1$ is protected as an acetal.)

Step 3-1: Coupling Reaction

Compound a17 is produced by coupling compound a5 with compound a15 or a16 in the presence of a catalyst and abase. Examples of the catalyst include transition metals such as palladium, salts thereof, complexes thereof, and supports such as polymers having them supported thereon. The base is appropriately selected from the bases and the like listed below, and examples thereof preferably include sodium carbonate and potassium carbonate. The solvent is appropriately selected from the solvents and the like listed below, and examples thereof preferably include a mixed solvent of 1,2-dimethoxyethane and water. The reaction time is normally 5 minutes to 72 hours, and is preferably 30 minutes to 24 hours. The reaction temperature is normally 0° C. to 200° C., and is preferably 20° C. to 150° C. The reaction temperature is normally 0° C. to 200° C., and is preferably 0° C. to 100° C.

Step 3-2: Deacetalization Reaction

Compound a18 is produced by allowing compound a17 to react with various acids in an appropriate solvent. Examples of the acid include hydrochloric acid, trifluoroacetic acid, acetic acid, and sulfuric acid. The solvent is appropriately selected from the solvents and the like listed below, and examples thereof preferably include tetrahydrofuran or acetone. The reaction time is normally 5 minutes to 72 hours, and is preferably 30 minutes to 24 hours. The reaction temperature is normally 0° C. to 200° C., and is preferably 0° C. to 100° C.

Step 3-3: Debenzylation Reaction

Compound a19 is produced by reducing compound a18 in the presence of a catalyst. As the reducing agent, hydrogen, salts of formic acid such as ammonium formate, and hydrazine can be used, for example. Examples of the catalyst include transition metals such as palladium, nickel, rhodium, cobalt, and platinum, salts thereof, complexes thereof, and supports such as polymers having them supported thereon. The solvent is appropriately selected from the solvents and the like listed below, and examples thereof preferably include ethyl acetate, ethanol, or methanol. The reaction time is normally 5 minutes to 72 hours, and is preferably 30 minutes to 24 hours. The reaction temperature is normally 0° C. to 200° C., and is preferably 0° C. to 100° C.

Step 3-4: Reduction Reaction

Compound a13 is produced by reducing compound a19 using a reducing agent in the presence of a catalyst and/or a base. The reaction can also be carried out using only a reducing agent. As the reducing agent, hydrogen, salts of formic acid such as sodium formate, hydrazine, sodium borohydride or lithium tri-sec-butylborohydride, and the like can be used, for example. Examples of the catalyst include transition metals such as ruthenium, palladium, nickel, rhodium, cobalt, and platinum, salts thereof, complexes thereof, and supports such as polymers having them supported thereon. The base is appropriately selected from the bases and the like listed below, and examples thereof preferably include potassium tert-butoxide, potassium hydroxide, and triethylamine. The solvent is appropriately selected from the solvents and the like listed below, and examples thereof preferably include tetrahydrofuran, 2-propanol, ethanol, methanol, or dimethylformamide. The reaction time is normally 5 minutes to 72 hours, and is preferably 30 minutes to 24 hours. The reaction temperature is normally −80° C. to 200° C., and is preferably −80° C. to 100° C. It is more preferably 0° C. to 100° C.

Production Method 4

Among the compounds represented by formula (1), a compound represented by formula [A3] can be produced by, for example, the production method below.

(In the formula, $R^{41}$ and $R^{42}$ are each $R^4$, which is the same or different; $L^3$ is —NH—C(═O)— or —C(═O)—NH—; and $R^1$, $R^2$, $R^3$, $R^4$, X, and Y are the same as in item 1.)

Step 4-1: Condensation Reaction

Compound a22 is produced by allowing compound a20 to react with compound a2 in an appropriate solvent in the presence of or in the absence of various condensing agents and/or bases. As the condensing agent, various condensing agents used in conventional methods can be used, and examples thereof preferably include propylphosphonic acid anhydride or 1-ethyl-3-(3-dimethylaminopropyl)carbodiimide (including hydrochloride). The base is appropriately selected from the bases and the like listed below, and examples thereof preferably include diisopropylethylamine or triethylamine. The solvent is appropriately selected from the solvents and the like listed below, and examples thereof preferably include tetrahydrofuran, dimethylformamide, or chloroform. The reaction time is normally 5 minutes to 72 hours, and is preferably 30 minutes to 24 hours. The reaction temperature is normally 0° C. to 200° C., and is preferably 0° C. to 100° C.

Step 4-2: Condensation Reaction

Compound a22 is produced by allowing compound a21 to react with compound a4 in an appropriate solvent in the presence of or in the absence of various condensing agents and/or bases. As the condensing agent, various condensing agents used in conventional methods can be used, and examples thereof preferably include propylphosphonic acid anhydride or 1-ethyl-3-(3-dimethylaminopropyl)carbodiim

[Chemical Formula 37]

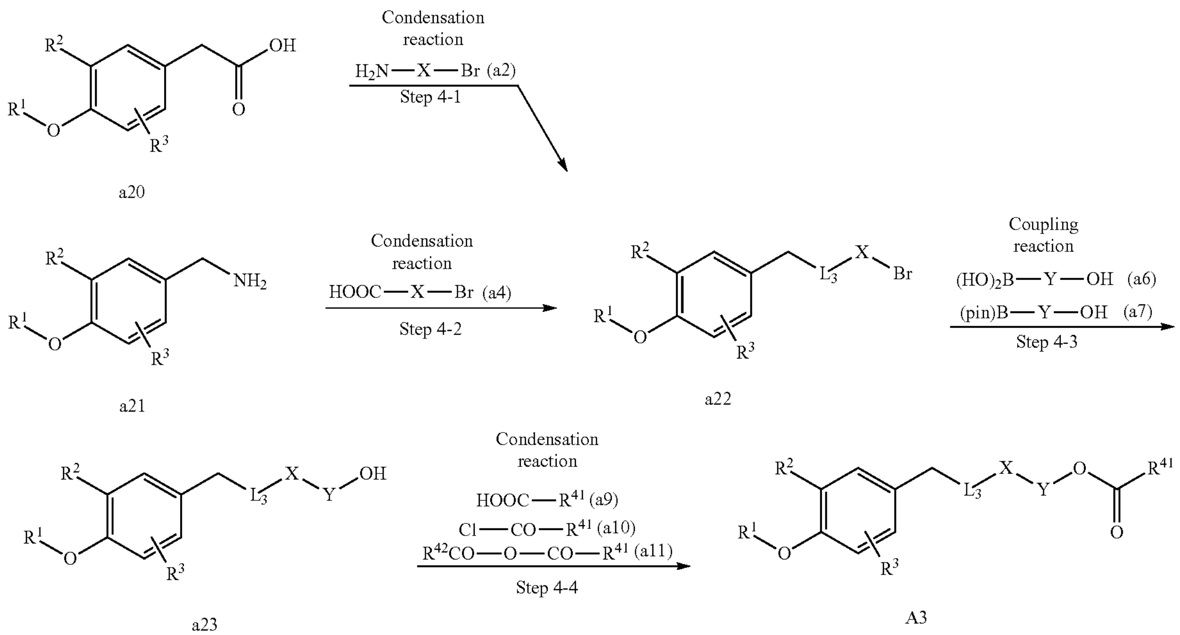

a20 a21 a22 a23 A3 ide (including hydrochloride). The base is appropriately selected from the bases and the like listed below, and examples thereof preferably include diisopropylethylamine or triethylamine. The solvent is appropriately selected from the solvents and the like listed below, and examples thereof preferably include tetrahydrofuran, dimethylformamide, or chloroform. The reaction time is normally 5 minutes to 72 hours, and is preferably 30 minutes to 24 hours. The reaction temperature is normally 0° C. to 200° C., and is preferably 0° C. to 100° C.

Step 4-3: Coupling Reaction

Compound a23 is produced by coupling compound a22 with compound a6 or a7 in the presence of a catalyst and a base. Examples of the catalyst include transition metals such as palladium, salts thereof, complexes thereof, and supports such as polymers having them supported thereon. The base is appropriately selected from the bases and the like listed below, and examples thereof preferably include sodium carbonate and potassium carbonate. The solvent is appropriately selected from the solvents and the like listed below, and examples thereof preferably include a mixed solvent of 1,2-dimethoxyethane and water. The reaction time is normally 5 minutes to 72 hours, and is preferably 30 minutes to 24 hours. The reaction temperature is normally 0° C. to 200° C., and is preferably 20° C. to 150° C. The reaction temperature is normally 0° C. to 200° C., and is preferably 0° C. to 100° C.

Step 4-4: Condensation Reaction

Compound A3 is produced by allowing compound a23 to react with compound a9, a10, or all in an appropriate solvent in the presence of or in the absence of various condensing agents and/or bases. As the condensing agent, various condensing agents used in conventional methods can be used, and examples thereof preferably include 1-ethyl-3-(3-dimethylaminopropyl)carbodiimide (including hydrochloride). The base is appropriately selected from the bases and the like listed below, and examples thereof preferably include diisopropylethylamine or triethylamine. The solvent is appropriately selected from the solvents and the like listed below, and examples thereof preferably include tetrahydrofuran, dimethylformamide, or chloroform. The reaction time is normally 5 minutes to 72 hours, and is preferably 30 minutes to 24 hours. The reaction temperature is normally 0° C. to 200° C., and is preferably 0° C. to 100° C.

Compound a20 used can be any of those commercially available, or can be produced in accordance with known methods, such as the method described in ACS Chem Neurosci. 2018, 9, 587-602.

Compound a21 used can be any of those commercially available, or can be produced in accordance with known methods, such as the method described in Nature Commun. 2018, 9, 4123.

Production Method 5

The compound represented by formula [a23] can be produced by, for example, the following production method.

[Chemical Formula 38]

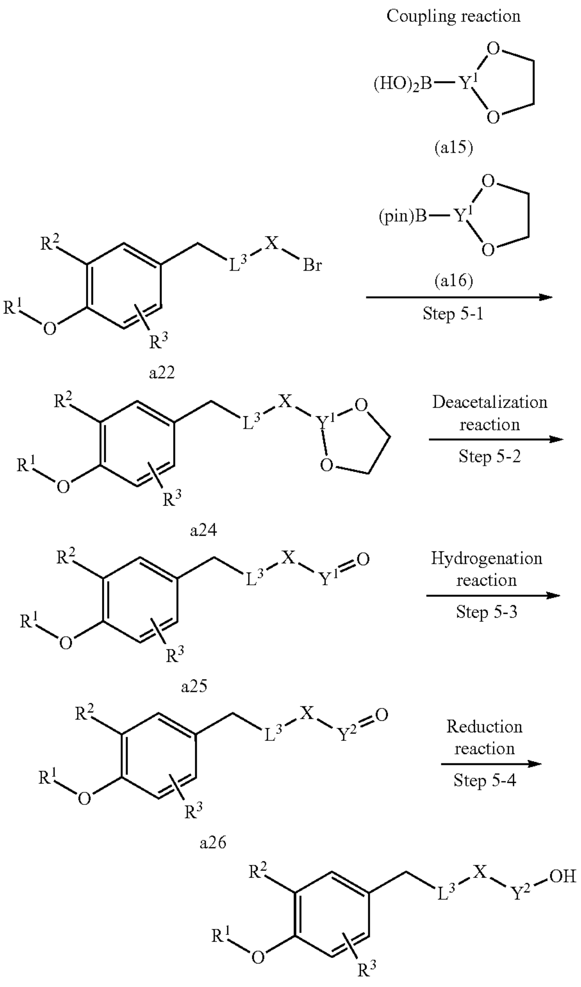

(a15) (a16) a22 a24 a25 a26 a23

(In the formula, $Y^1$ is a $C_{3-10}$ alicyclic group having an unsaturated bond; $Y^2$ is a $C_{3-10}$ alicyclic group; $L^3$ is —NH—C(═O)— or —C(═O)—NH—; $R^1$, $R^2$, $R^3$, and X are the same as in item 1; and a15, a16, and a24 represent compounds in which the carbonyl group on $Y^1$ is protected as an acetal.)

Step 5-1: Coupling Reaction

Compound a24 is produced by coupling compound a22 with compound a15 or a16 in the presence of a catalyst and abase. Examples of the catalyst include transition metals such as palladium, salts thereof, complexes thereof, and supports such as polymers having them supported thereon. The base is appropriately selected from the bases and the like listed below, and examples thereof preferably include sodium carbonate and potassium carbonate. The solvent is appropriately selected from the solvents and the like listed below, and examples thereof preferably include a mixed solvent of 1,2-dimethoxyethane and water. The reaction time is normally 5 minutes to 72 hours, and is preferably 30 minutes to 24 hours. The reaction temperature is normally 0° C. to 200° C., and is preferably 20° C. to 150° C. The reaction temperature is normally 0° C. to 200° C., and is preferably 0° C. to 100° C.

Step 5-2: Deacetalization Reaction

Compound a25 is produced by allowing compound a24 to react with various acids in an appropriate solvent. Examples of the acid include hydrochloric acid, trifluoroacetic acid, acetic acid, and sulfuric acid. The solvent is appropriately selected from the solvents and the like listed below, and examples thereof preferably include tetrahydrofuran or acetone. The reaction time is normally 5 minutes to 72 hours, and is preferably 30 minutes to 24 hours. The reaction temperature is normally 0° C. to 200° C., and is preferably 0° C. to 100° C.

Step 5-3: Hydrogenation Reaction

Compound a26 is produced by reducing compound a25 in the presence of a catalyst. As the reducing agent, hydrogen, salts of formic acid such as ammonium formate, and hydrazine can be used, for example. Examples of the catalyst include transition metals such as palladium, nickel, rhodium, cobalt, and platinum, salts thereof, complexes thereof, and supports such as polymers having them supported thereon. The solvent is appropriately selected from the solvents and the like listed below, and examples thereof preferably include ethyl acetate, ethanol, or methanol. The reaction time is normally 5 minutes to 72 hours, and is preferably 30 minutes to 24 hours. The reaction temperature is normally 0° C. to 200° C., and is preferably 0° C. to 100° C.

Step 5-4: Reduction Reaction

Compound a23 is produced by reducing compound a26 using a reducing agent in the presence of a catalyst and/or a base. The reaction can also be carried out using only a reducing agent. As the reducing agent, hydrogen, salts of formic acid such as sodium formate, hydrazine, sodium borohydride or lithium tri-sec-butylborohydride, and the like can be used, for example. Examples of the catalyst include transition metals such as ruthenium, palladium, nickel, rhodium, cobalt, and platinum, salts thereof, complexes thereof, and supports such as polymers having them supported thereon. The base is appropriately selected from the bases and the like listed below, and examples thereof preferably include potassium tert-butoxide, potassium hydroxide, and triethylamine. The solvent is appropriately selected from the solvents and the like listed below, and examples thereof preferably include tetrahydrofuran, 2-propanol, ethanol, methanol, or dimethylformamide. The reaction time is normally 5 minutes to 72 hours, and is preferably 30 minutes to 24 hours. The reaction temperature is normally −80° C. to 200° C., and is preferably −80° C. to 100° C. It is more preferably 0° C. to 100° C.

The bases used in each step of the above production methods should be appropriately selected depending on reactions, types of raw material compounds, and the like, and examples thereof include alkali bicarbonates such as sodium bicarbonate and potassium bicarbonate; alkali carbonates such as sodium carbonate, potassium carbonate, and cesium carbonate; metal fluorides such as potassium fluoride and cesium fluoride; metal hydrides such as sodium hydride and potassium hydride; alkali metal hydroxides such as sodium hydroxide and potassium hydroxide; alkali metal alkoxides such as sodium methoxide and sodium tert-butoxide; organometallic bases such as butyllithium, lithium diisopropylamide, and lithium (bistrimethylsilyl)amide; and organic bases such as triethylamine, diisopropylethylamine, pyridine, 4-dimethylaminopyridine (DMAP), 1,8-diazabicyclo[5.4.0]-7-undecene (DBU), and 1,4-diazabicyclo[2.2.2]octane (DABCO).

The solvents used in each step of the above production methods should be appropriately selected depending on reactions, types of raw material compounds, and the like, and examples thereof include alcohols such as methanol, ethanol, and 2-propanol; ketones such as acetone and methyl ketone; halogenated hydrocarbons such as methylene chloride and chloroform; ethers such as tetrahydrofuran (THF) and dioxane; aromatic hydrocarbons such as toluene, benzene, and xylene; aliphatic hydrocarbons such as hexane and heptane; esters such as ethyl acetate and propyl acetate; amides such as N,N-dimethylformamide (DMF) and N-methyl-2-pyrrolidone; sulfoxides such as dimethylsulfoxide (DMSO); and nitriles such as acetonitrile, and one of these solvents may be used singly, or two or more of them may be mixed for use. In addition, depending on the type of reactions, organic bases may be used as the solvent.

The compound of the present disclosure represented by formula (1) or intermediates thereof can be separated and purified by methods known to those skilled in the art. Examples thereof include extraction, partitioning, reprecipitation, column chromatography (for example, silica gel column chromatography, ion exchange column chromatography, or preparative liquid chromatography) or recrystallization.

As the recrystallization solvent, for example, alcohol solvents such as methanol, ethanol, or 2-propanol; ether solvents such as diethyl ether; ester solvents such as ethyl acetate; aromatic hydrocarbon solvents such as benzene or toluene; ketone solvents such as acetone; halogenated solvents such as dichloromethane or chloroform; hydrocarbon solvents such as hexane; aprotic solvents such as dimethylformamide or acetonitrile; water; or mixed solvents thereof can be used. As another purification method, the method described in The Experimental Chemistry (edited by The Chemical Society of Japan, Maruzen), vol. 1 and the like can be used. In addition, determination of the molecular structure of the compound of the present disclosure can be readily carried out by making reference to the structure originating from each raw material compound and through spectroscopic approaches such as nuclear magnetic resonance, infrared absorption technique, and circular dichroism spectroscopy, and mass spectrometry.

In addition, the intermediates or end products in the above production methods can also be derivatized into other compounds included in the present disclosure by properly converting their functional groups, also in particular, by extending various side chains from an amino group, hydroxyl group, carbonyl group, halogen atom, or the like, and upon this, by carrying out the protection and deprotection described below as necessary. The conversion of functional groups and extension of side chains can be carried out by general methods that are normally performed (for example, see Comprehensive Organic Transformations, R. C. Larock, John Wiley & Sons Inc. (1999) and the like).

As the protecting group for the amino group, for example, an alkylcarbonyl group (for example, an acetyl group and a propionyl group), a formyl group, a phenylcarbonyl group, an alkyloxycarbonyl group (for example, a methoxycarbonyl group, an ethoxycarbonyl group, and a tert-butoxycarbonyl group), a phenyloxycarbonyl group, an arylalkyloxycarbonyl group (for example, a benzyloxycarbonyl group), a trityl group, a phthaloyl group, a tosyl group, and a benzyl are used.

As the protecting group for the carboxyl group, for example, an alkyl group (for example, a methyl group, an ethyl group, a propyl group, an isopropyl group, a butyl group, and a tert-butyl group), a phenyl group, a benzyl group, a trityl group, and a silyl group (for example, a trimethylsilyl group and a tert-butyldimethylsilyl group) are used.

As the protecting group for the hydroxy group, for example, a methyl group, a tert-butyl group, an allyl group, a substituted methyl group (for example, a methoxymethyl group and a methoxyethoxymethyl group), an ethoxyethyl group, a tetrahydropyranyl group, a tetrahydrofuranyl group, a trityl group, an arylalkyl group (for example, a benzyl group), an alkylcarbonyl group (for example, an acetyl group and a propionyl group), a formyl group, a benzoyl group, an arylalkyloxycarbonyl group (for example, a benzyloxycarbonyl group), and a silyl group (for example, a trimethylsilyl group and a tert-butyldimethylsilyl group) are used.

Protection of the carbonyl group can be carried out by converting the carbonyl group to an acyclic ketal (dimethyl ketal, diethyl ketal, or the like) or a cyclic ketal (1,3-dioxolane, 1,3-dioxane, or the like).

The compound of the present disclosure represented by formula (1) or pharmaceutically acceptable salt thereof may have asymmetry or may have a substituent having an asymmetric carbon, and optical isomers are present in such a compound. M fixtures of these isomers, as well as isolated ones, are also encompassed in the compound of the present disclosure, and they can be produced according to normal methods.

Examples of the production method include a method of using a raw material having an asymmetric point or a method of introducing asymmetry in the midway stage. For example, in the case of optical isomers, by using optically active raw materials or by carrying out optical resolution or the like at an appropriate stage during the production process, optical isomers can be obtained. Examples of the optical resolution method include, when the compound represented by formula (1) or an intermediate thereof has a basic functional group, diastereomer method, in which a salt is formed using an optically active acid (for example, a monocarboxylic acid such as mandelic acid, N-benzyloxyalanine, and lactic acid; a dicarboxylic acid such as tartaric acid, o-diisopropylidene tartaric acid, and malic acid; or a sulfonic acid such as camphorsulfonic acid and bromocamphorsulfonic acid) in an inert solvent (for example, an alcohol solvent such as methanol, ethanol, and 2-propanol; an ether solvent such as diethyl ether; an ester solvent such as ethyl acetate; a hydrocarbon solvent such as toluene; an aprotic solvent such as acetonitrile; or a mixed solvent of two or more selected from the above solvents).

When the compound of the present disclosure represented by formula (1) or an intermediate thereof has an acidic functional group such as a carboxyl group, optical resolution can also be carried out by using an optically active amine (for example, an organic amine such as 1-phenylethylamine, quinine, quinidine, cinchonidine, cinchonine, and strychnine) to form a salt.

The temperature at which the salt is formed is selected from the range of −50° C. to the boiling point of the solvent, preferably from the range of 0° C. to the boiling point, and more preferably from the range of room temperature to the boiling point of the solvent. In order to improve optical purity, it is desirable that the temperature be once raised to the vicinity of the boiling point of the solvent. Upon separating the precipitated salt by filtration, the yield can be improved by cooling the reaction solution as necessary. The amount of the optically active acid or amine to be used is in the range of about 0.5 to about 2.0 equivalent relative to the substrate, and preferably, the range around 1 equivalent is appropriate. As necessary, an optically active salt with high purity can also be obtained by allowing a crystal to be recrystallized in an inert solvent (for example, an alcohol solvent such as methanol, ethanol, and 2-propanol; an ether solvent such as diethyl ether; an ester solvent such as ethyl acetate; a hydrocarbon solvent such as toluene; an aprotic solvent such as acetonitrile; or a mixed solvent of two or more selected from the above solvents). In addition, as necessary, by treating a salt that has been optically resolved with an acid or base through a normal method, a free form can also be obtained.

Among the raw materials and intermediates in the production methods described above, those, the production method of which is not expressly described, are commercially available compounds, or can be synthesized from commercially available compounds by methods known to those skilled in the art or methods equivalent thereto.

The term “disorder or disease in which TRPV1 is involved” refers to a disorder or disease caused by the increased activity of TRPV1-expressing nerve cells, and examples thereof include dysphagia, pain, skin disease, respiratory disease, digestive disease, urological disease, diabetes, and obesity. Examples of the pain include neuropathic pain, post-herpetic neuralgia, and pain due to gonarthrosis. Examples of the skin disease include psoriasis, atopic dermatitis, primary hyperhidrosis, and alopecia. Examples of the respiratory disease include cough and asthma. Examples of the digestive disease include acute gastritis, acute gastric mucosal lesions, and fecal incontinence. Examples of the urological disease include cystitis and overactive bladder. The “disorder or disease in which TRPV1 is involved” is preferably dysphagia.

The present disclosure provides a pharmaceutical composition containing the compound of the present invention or pharmaceutically acceptable salt thereof as an active ingredient, wherein the composition is for treating or preventing dysphagia. “Dysphagia” refers to a condition in which it becomes difficult to chew or swallow food or drink due to disease, aging, or other causes. Specific examples thereof include swallowing asynergy, difficulty in swallowing, dysphagia, pain on swallowing, aphagia, and cricopharyngeal muscle dysfunction. It also includes dysphagia due to cerebrovascular diseases such as cerebral infarction and cerebral hemorrhage, neurodegenerative diseases such as Parkinson’s disease and ALS, and dementia such as Alzheimer-type. Furthermore, it also includes situations in which swallowing function is decreased due to therapeutic drugs such as analgesics, antipsychotics, antihistamines, and anticholinergics.

The effect of the compound of the present disclosure on dysphagia can be evaluated using the swallowing function of dysphagia model animals as an indicator. Similar to dysphagia in humans, it has been reported that dysphagia occurs in aged animals, cerebral infarction model animals, and Parkinson’s disease model animals, and the effect can be evaluated in these models. (Dysphagia (2014) 29: 61-67, Dysphagia. 2015 June; 30(3): 328-42, Dysphagia. 2013 March; 28(1): 95-104).

Note that, in the present disclosure, “preventing” is the act of administering the active ingredient of the present disclosure to a healthy person who has not developed a disease or exhibits a mild symptom, and is intended to prevent the onset of a disease, for example. “Treating” is the act of administering the active ingredient of the present disclosure to a person (patient) who has been diagnosed by a physician as developing a disease.

The route of administration of the compound of the present disclosure may be oral administration, parenteral administration, or intrarectal administration, and its daily dosage varies depending on the type of compound, the method of administration, the symptom and age of the patient, and other factors. For example, in the case of oral administration, the compound of the present disclosure can be administered normally at a dose of about 0.01 to 1000 mg, still more preferably about 0.1 to 500 mg, per kg body weight of human or mammal, divided into one to several doses. In the case of parenteral administration such as intravenous infusion, for example, the compound of the present disclosure can be administered normally at a dose of about 0.01 mg to 300 mg, still more preferably about 0.01 mg to 100 mg, per kg body weight of human or mammal.

The compound of the present disclosure can be administered through oral administration or parenteral administration, directly or as a formulation using an appropriate dosage form. Examples of the dosage form include, but are not limited to, tablet, capsule, powder, granule, liquid, suspension, injection, patch, and poultice. The formulations are produced by known methods, using a pharmaceutically acceptable additive. For the additive, an excipient, a disintegrating agent, a binder, a glidant, a lubricant, a coating agent, a solubilizing agent, a solubilization aid, a thickening agent, a dispersing agent, a stabilizer, a sweetening agent, a perfume, and the like can be used according to purposes. Specifically, examples thereof include lactose, mannitol, crystalline cellulose, low substituted hydroxypropyl cellulose, corn starch, partially pregelatinized starch, carmellose calcium, croscarmellose sodium, hydroxypropyl cellulose, hydroxypropyl methylcellulose, polyvinyl alcohol, magnesium stearate, sodium stearyl fumarate, polyethylene glycol, propylene glycol, titanium oxide, and talc.

The compound of the present disclosure can be administered in combination with an agent that potentially improves swallowing function, and can be administered in order to treat or prevent dysphagia. Examples of such agents include a L-Dopa formulation in Parkinson's disease, an immunoglobulin formulation in sporadic inclusion body myositis, and Miglustat, a glucosylceramide synthase inhibitor, in Niemann-Pick disease type C, as well as an ACE inhibitor, cilostazol, nicergoline, and hangekobokuto as a drug that potentially improves the swallowing reflex. In the present disclosure, drugs that can be used in combination with the compound of the present invention are abbreviated as other agents.

Duration of administration of the compound of the present invention and the concomitant agent is not limited, and they may be administered to the target of administration simultaneously, or may be administered at different times. Alternatively, the compound of the present invention and the concomitant agent may be formed into a combined agent. The dosage of the concomitant agent can be appropriately selected on the basis of the clinically used dose. In addition, the mixing ratio of the compound of the present invention and the concomitant agent can be appropriately selected depending on target of administration, route of administration, target disease, symptom, combination, and other factors. For example, when the target of administration is human, 0.01 to 100 parts by weight of the concomitant agent may be used relative to 1 part by weight of the compound of the present invention. It can also be used in combination with an agent (concomitant agent) such as an antiemetic, a sleep inducing drug, and an anticonvulsant for the purpose of suppressing its side effects.

In the present specification, the term "or" is used when "at least one or more" of the items listed in the text can be employed. The same applies to "or". When stated herein as "within the range between two values", that range includes the two values themselves as well.

The references cited herein, including scientific literature, patents, and patent applications, are hereby incorporated by reference in their entirety to the same extent as if each were specifically described herein.

The present disclosure has been described above, with preferred embodiments shown for ease of understanding. Hereinafter, the present disclosure will be described based on Examples, but the above description and the following Examples are provided solely for illustrative purposes and are not provided for the purpose of limiting the present disclosure. Accordingly, the scope of the present disclosure is neither limited to the embodiments nor to the Examples specifically described herein, but is limited only by the claims.

EXAMPLES

Hereinafter, the present disclosure will be explained further specifically with reference to Reference Examples, Examples, and Test Examples, but the present disclosure is not limited to them, of course. Note that the names of compounds shown in the following Reference Examples and Examples do not necessarily follow the IUPAC nomenclature of chemistry.

In order to simplify description of the specification, abbreviations as shown below may be used in Examples and the tables in Examples. As an abbreviation used for a substituent, pin means pinacol. For symbols used for NMR, s means a singlet, d means a doublet, dd means a doublet of doublets, t means a triplet, q means a quartet, n means a multiplet, br means broad, brs means a broad singlet, and J means the binding constant.

High performance liquid chromatography-mass spectrometer; measurement conditions for LCMS are as follows, and the observed value of mass spectrometry [MS (m/z)] is shown as $MH^+$, and the retention time is shown as Rt (min).

Measurement Conditions

Detection equipment: ACQUITY (R) SQ detector (Waters Corporation)

HPLC: ACQUITY UPLC (R) SYSTEM

Column: Waters ACQUITY UPLC (R) BEH C18 (1.7 μm, 2.1 mm×30 mm)

Solvent:

solution A; 0.05% formic acid/$H_2O$, solution B; acetonitrile

Gradient Condition:

0.0 to 1.3 min (linear gradient from B 10% to 95%)

1.3 to 1.5 min (B 10%)

Flow rate: 0.8 ml/min

UV: 220 nm and 254 nm

Column temperature: 40° C.

Reference Example 1

2-[4-(Benzyloxy)-3-methoxyphenyl]-N-(6-bromopyridin-2-yl)acetamide

[Chemical Formula 39]

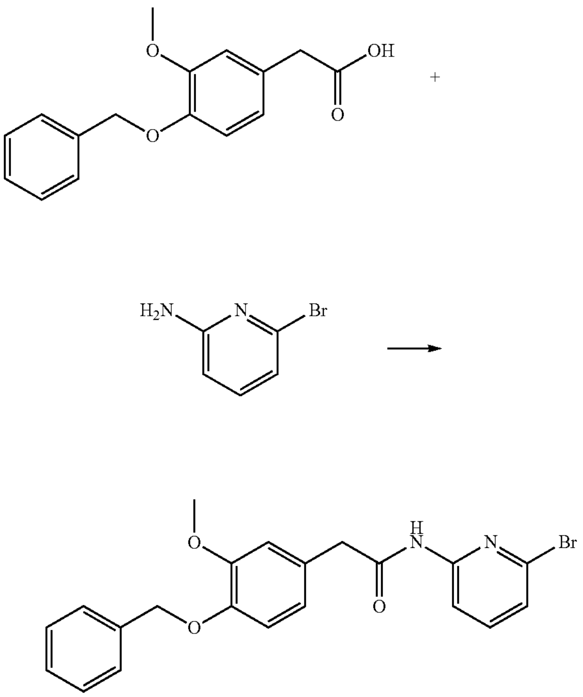

Reference Example 1

To a solution of 4-benzyloxy-3-methoxyphenylacetic acid (4.0 g) and 6-bromopyridin-2-amine (2.8 g) in 1,2-dimethoxyethane (30 ml) were added N,N-diisopropylethylamine (5.1 ml) and 50% propylphosphonic acid anhydride in ethyl acetate solution (10.5 ml), and the mixture was stirred at room temperature for 1.5 hours. Water was added to the reaction solution, which was then extracted with ethyl acetate. The obtained organic layer was washed with water and saturated saline solution, dried over sodium sulfate, filtered, and concentrated under reduced pressure, and the produced solid was washed with diethyl ether to afford Reference Example 1 (4.0 g).

LC-MS, m/z; 427.08 $(M+H)^+$ ESI, Rt; 1.071 (min)

Reference Example 2

2-[4-(Benzyloxy)-3-methoxyphenyl]-N-[6-(3-hydroxyphenyl)pyridin-2-yl]acetamide hydrochloride

[Chemical Formula 40]

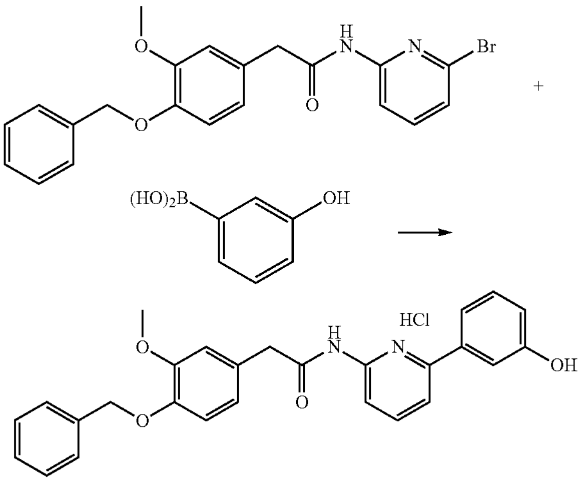

Reference Example 2

To a solution of 2-[4-(benzyloxy)-3-methoxyphenyl]-N-(6-bromopyridin-2-yl)acetamide (8.61 g), 3-hydroxyphenylboronic acid (3.06 g), and potassium carbonate (5.57 g) in 1,2-dimethoxyethane (200 ml)/water (40 ml) was added dichlorobis(di-tert-butyl(4-dimethylaminophenyl)phosphine)palladium(11) (0.71 g), and the mixture was subjected to heating reflux for 2 hours. The reaction solution was concentrated, ethyl acetate was then added thereto, and the organic layer was washed with water and saturated saline solution. Activated carbon was added, the mixture was dried over sodium sulfate, filtered, and concentrated under reduced pressure, and tetrahydrofuran (100 ml) was added to the produced crude product. Thereafter, 4 mol/L hydrogen chloride, cyclopentyl methyl ether solution (30 ml) was added, and the mixture was stirred under room temperature conditions for 30 minutes. After concentrating the reaction solution, the obtained solid was washed with diethyl ether to afford Reference Example 2 (8.58 g).

LC-MS, m/z; 441.25 $(M+H)^+$ ESI, Rt; 0.998 (min)

Example 1 and Reference Example 3

3-{6-[2-(4-Hydroxy-3-methoxyphenyl)acetamido]pyridin-2-yl}phenyl 2-methylpropanoate

[Chemical Formula 41]

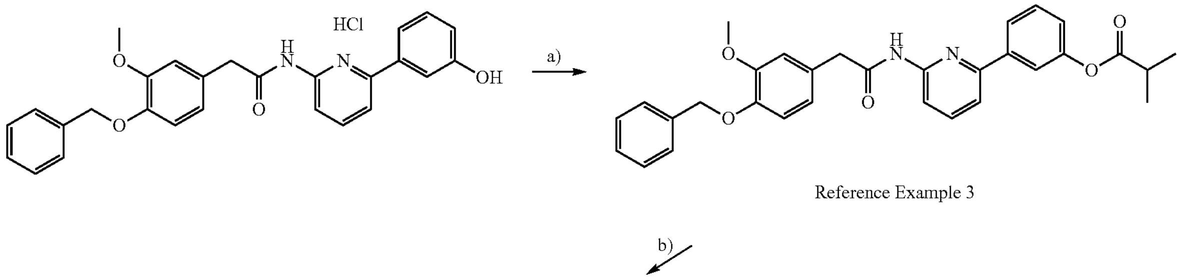

Reference Example 3

-continued

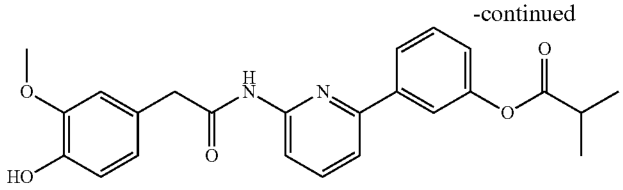

Example 1 a) Production of 3-(6-{2-[4-(benzyloxy)-3-methoxy-phenyl]acetamido}pyridin-2-yl)phenyl 2-methylpropanoate Reference Example 3

To a solution of 2-[4-(benzyloxy)-3-methoxyphenyl]-N-[6-(3-hydroxyphenyl)pyridin-2-yl]acetamide hydrochloride (1.0 g) and triethylamine (0.791 ml) in tetrahydrofuran (23 ml) was added isobutyryl chloride (0.263 ml), and the mixture was stirred at room temperature for 3 hours. Water was added to the reaction solution, which was extracted with ethyl acetate, and the organic layer was then washed with saturated aqueous sodium bicarbonate solution and saturated saline solution. It was dried over sodium sulfate, filtered, and concentrated under reduced pressure to afford a crude product of Reference Example 3.

LC-MS, m/z; 511.34 $(M+H)^+$ ESI, Rt; 1.234 (min)

b) Production of 3-{6-[2-(4-hydroxy-3-methoxyphenyl)acetamido]pyridin-2-yl}phenyl 2-methylpropanoate Example 1

To a solution of 3-(6-{2-[4-(benzyloxy)-3-methoxyphenyl]acetamido}pyridin-2-yl)phenyl 2-methylpropanoate (1.159 g) in ethyl acetate (30 ml) was added palladium-activated carbon (Pd 20%) (1.0 g), and the mixture was stirred under a hydrogen atmosphere at room temperature for 5 hours. The reaction solution was purged with nitrogen, then filtered through celite, and concentrated under reduced pressure, and hexane was added to the residue thus obtained to afford a crude product solid. The obtained solid was recrystallized from 2-propanol to afford Example 1 (352 mg).

LC-MS, m/z; 421.2 $(M+H)^+$ ESI, Rt; 0.993 (min)

$^1$H-NMR (400 MHz, $CD_3OD$) δ: 8.07 (1H, d, J=8.0 Hz), 7.91 (1H, dd, J=1.4, 7.8 Hz), 7.83-7.79 (2H, m), 7.61 (1H, d, J=7.2 Hz), 7.48 (1H, t, J=7.8 Hz), 7.14-7.10 (1H, m), 6.97 (1H, d, J=2.0 Hz), 6.81 (1H, dd, J=2.0, 8.4 Hz), 6.76 (1H, d, J=7.6 Hz), 3.86 (3H, s), 3.67 (2H, s), 2.86 (11H, p, J=6.9 Hz), 1.33 (6H, d, J=6.8 Hz).

Reference Example 4

N-{[4-(Benzyloxy)-3-methoxyphenyl]methyl}-3-bromobenzamide

[Chemical Formula 42]

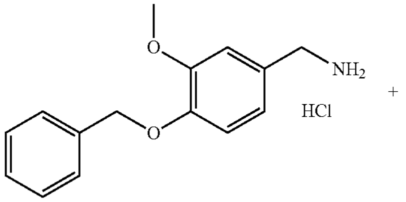

-continued

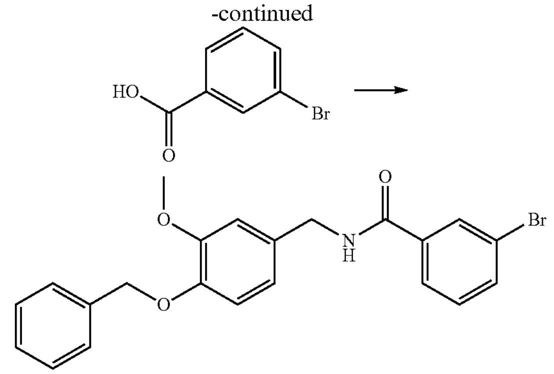

Reference Example 4

To a solution of (4-(benzyloxy)-3-methoxyphenyl)methanamine hydrochloride (5.0 g), and 3-bromobenzoic acid (3.95 g), and O-(7-azabenzotriazol-1-yl)-N,N,N',N'-tetramethyluronium hexafluorophosphate (6.8 g) in dimethylformamide (36 ml) was added N,N-diisopropylethylamine (6.87 ml), and the mixture was stirred under room temperature conditions for 24 hours. Water was added to the reaction solution, which was then extracted with ethyl acetate. The obtained organic layer was washed with water and saturated saline solution, dried over sodium sulfate, filtered, and concentrated under reduced pressure. The obtained crude product was purified by silica gel column chromatography (eluting solution; hexane:ethyl acetate), and the obtained solid was washed with hexane to afford Reference Example 4 (8.0 g).

LC-MS, m/z; 426.13 $(M+H)^+$ ESI, Rt; 1.029 (min)

Reference Example 5

N-{[4-(Benzyloxy)-3-methoxyphenyl]methyl}-3'-hydroxy[1,1'-biphenyl]-3-carboxamide

[Chemical Formula 43]

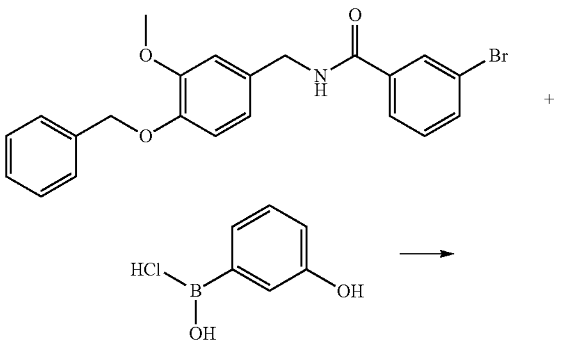

-continued

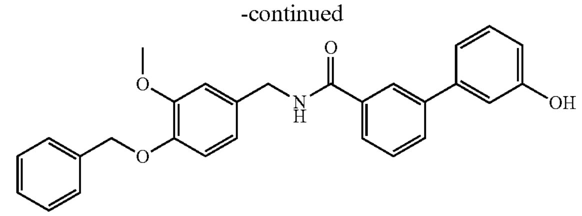

Reference Example 5

To 1,2-dimethoxyethane (70 ml)/water (7 ml) solution were added N-{[4-(benzyloxy)-3-methoxyphenyl]methyl}-3-bromobenzamide (3.0 g), 3-hydroxyphenylboronic acid (1.65 g), (1,1-bis(diphenylphosphino)ferrocene)dichloropalladium(II) (0.575 g), and cesium carbonate (4.59 g), and the mixture was stirred at 100° C. for 5 hours. The reaction solution was filtered through celite, ethyl acetate was added, and the organic layer was washed with water and saturated saline solution. It was dried over sodium sulfate, filtered, and concentrated under reduced pressure, the obtained crude product was purified by silica gel column chromatography (eluting solution; hexane:ethyl acetate), and the obtained solid was washed with hexane/ethyl acetate=10:1 solution to afford Reference Example 5 (2.62 g). LC-MS, m/z; 440.30 $(M+H)^+$ ESI, Rt; 0.955 (min)

Reference Examples 6 to 8

2-(4-Hydroxy-3-methoxyphenyl)-N-(3-(4-oxocyclohexyl)phenyl)acetamide

[Chemical Formula 44]

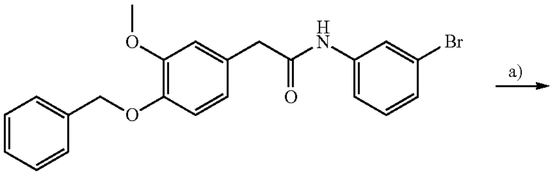

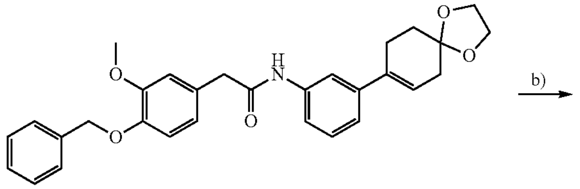

Reference Example 6

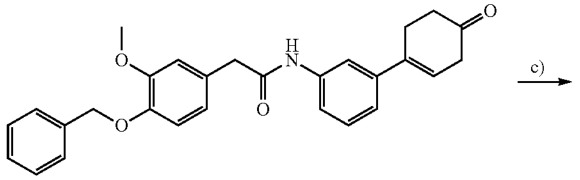

Reference Example 7

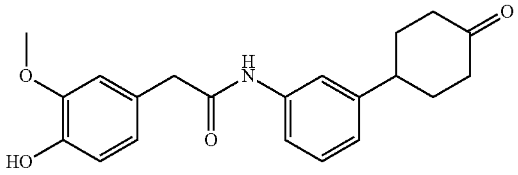

Reference Example 8 a) Production of 2-[4-(benzyloxy)-3-methoxyphenyl]-N-[3-(1,4-dioxaspiro[4.5]dec-7-en-8-yl)phenyl]acetamide (Reference Example 6)

To a solution of 2-(4-(benzyloxy)-3-methoxyphenyl)-N-(3-bromophenyl)acetamide (500 mg), 1,4-dioxaspiro[4,5]dec-7-en-8-phenylboronic acid pinacol ester (343 mg), and potassium carbonate (486 mg) in 1,2-dimethoxyethane (5 ml)/water (1 ml) was added dichlorobis(di-tert-butyl(4-dimethylaminophenyl)phosphine)palladium(II) (42 mg), and the mixture was subjected to heating reflux for 3 hours. The reaction solution was concentrated, chloroform was added, and the organic layer was washed with water, saturated aqueous sodium bicarbonate solution, and saturated saline solution. It was dried over sodium sulfate, filtered, and concentrated under reduced pressure, and the obtained crude product (693 mg) of Reference Example 6 was used for the next reaction as is.

LC-MS, m/z; 486.37 $(M+H)^+$ ESI, Rt; 1.058 (min)

b) Production of 2-[4-(benzyloxy)-3-methoxyphenyl]-N-(4'-oxo-2',3',4',5'-tetrahydro[1,1'-biphenyl]-3-yl)acetamide (Reference Example 7)

To a solution of the crude product (693 mg) of 2-[4-(benzyloxy)-3-methoxyphenyl]-N-[3-(1,4-dioxaspiro[4.5]dec-7-en-8-yl)phenyl]acetamide in tetrahydrofuran (30 ml) was added 5 mol/L hydrochloric acid (30 ml), and the mixture was stirred at room temperature for 1 hour. Water was added to the reaction solution, which was then extracted with ethyl acetate. The obtained organic layer was washed with water and saturated saline solution, dried over sodium sulfate, filtered, and concentrated under reduced pressure. The obtained crude product (570 mg) of Reference Example 7 was used for the next reaction as is.

LC-MS, m/z; 442.31 $(M+H)^+$ ESI, Rt; 0.982 (min)

c) Production of 2-(4-hydroxy-3-methoxyphenyl)-N-(3-(4-oxocyclohexyl)phenyl)acetamide (Reference Example 8)

To a solution of the crude product (570 mg) of 2-[4-(benzyloxy)-3-methoxyphenyl]-N-(4'-oxo-2',3',4',5'-tetrahydro[1,1'-biphenyl]-3-yl)acetamide in ethyl acetate (10 ml) was added palladium-activated carbon (Pd 20%) (250 mg), and the mixture was stirred under a hydrogen atmosphere at room temperature for 7 hours. The reaction solution was purged with nitrogen, then filtered through celite, and concentrated under reduced pressure, diethyl ether was added to the residue thus obtained, and Reference Example 8 (202 mg) was obtained by separating the precipitated solid by filtration.

LC-MS, m/z; 354.14 $(M+H)^+$ ESI, Rt; 0.678 (min)

Reference Example 9

N-{3-[(cis)-4-Hydroxycyclohexyl]phenyl}-2-(4-hydroxy-3-methoxyphenyl)acetamide

[Chemical Formula 45]

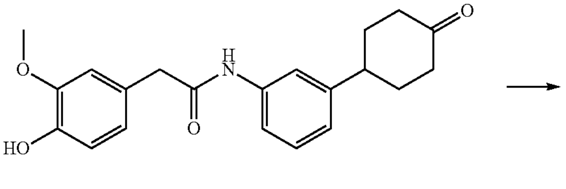

-continued

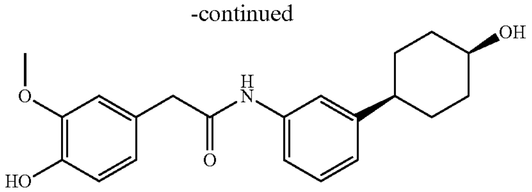

Reference Example 9

To a solution of dichlorobis(triphenylphophine)(1,2-ethanediamine)ruthenium(II) (492 mg) in 2-propanol (115 ml) were added potassium tert-butoxide (2.92 g) and tetrahydrofuran (115 ml). Subsequently, Reference Example 8 (2.3 g) was added, and the mixture was stirred under a hydrogen atmosphere at room temperature for 5.5 hours. The reaction solution was purged with nitrogen, then filtered through celite, and concentrated under reduced pressure. The obtained residue was dissolved in ethyl acetate, washed with 1 mol/L hydrochloric acid and saturated saline solution, and dried over sodium sulfate. The solvent was distilled off under reduced pressure, and the obtained residue was then purified by silica gel column chromatography (eluting solution; hexane:ethyl acetate) to afford Reference Example 9 (1.2 g).

LC-MS, m/z; 356.3 $(M+H)^+$ ESI, Rt; 0.683 (min)

-continued

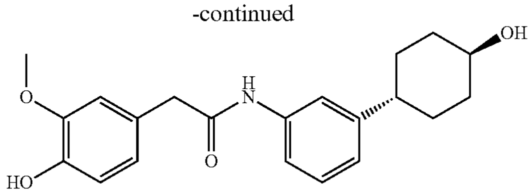

Reference Example 10

To a solution of 2-(4-hydroxy-3-methoxyphenyl)-N-(3-(4-oxocyclohexyl)phenyl)acetamide (500 mg) in tetrahydrofuran (14 ml) was added sodium borohydride (107 mg). After stirring the mixture at room temperature for 1.5 hours, saturated aqueous ammonium chloride solution was added to the reaction solution, the mixture was extracted with ethyl acetate, and the obtained organic layer was washed with water and saturated saline solution, dried over sodium sulfate, filtered, and concentrated under reduced pressure. The obtained residue was purified with methyl tert-butyl ether to afford Reference Example 10 (276 mg).

LC-MS, m/z; 356.2 $(M+H)^+$ ESI, Rt; 0.632 (min)

Reference Example 11

4-[2-(3-{(cis)-4-[(Cyclohexanecarbonyl)oxy]cyclohexyl}anilino)-2-oxoethyl]-2-methoxyphenyl cyclohexanecarboxylate

[Chemical Formula 47]

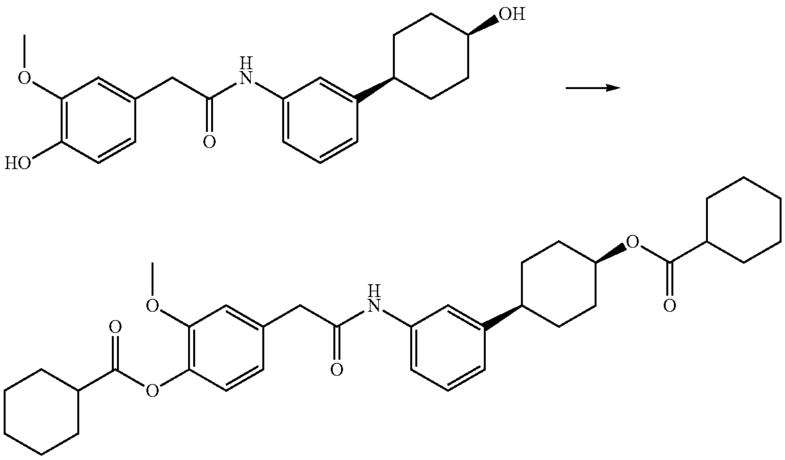

Reference Example 11

Reference Example 10

N-{3-[(trans)-4-Hydroxycyclohexyl]phenyl}-2-(4-hydroxy-3-methoxyphenyl)acetamide

[Chemical Formula 46]

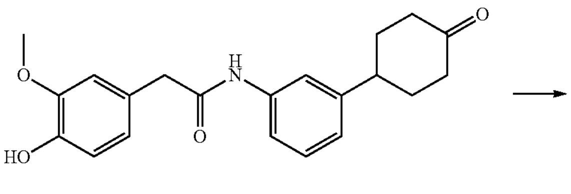

To a solution of N-{3-[(cis)-4-hydroxycyclohexyl]phenyl}-2-(4-hydroxy-3-methoxyphenyl)acetamide (1.0 g) and triethylamine (1.6 ml) in tetrahydrofuran (14 ml) was added cyclohexanecarbonyl chloride (1.1 ml). After stirring the mixture at room temperature for 4 days, water was added to the reaction solution, the mixture was extracted with chloroform, and the obtained organic layer was washed with water and saturated saline solution. It was dried over sodium sulfate, filtered, and concentrated under reduced pressure, the obtained residue was purified by silica gel column chromatography (eluting solution; hexane:ethyl acetate), and the obtained solid was washed with hexane to afford Reference Example 11 (1.05 g).

LC-MS, m/z; 576.39 $(M+H)^+$ ESI, Rt; 1.436 (min)

Reference Example 12

3'-Hydroxy-N-[(4-hydroxy-3-methoxyphenyl)methyl][1,1'-biphenyl]-3-carboxamide

[Chemical Formula 48]

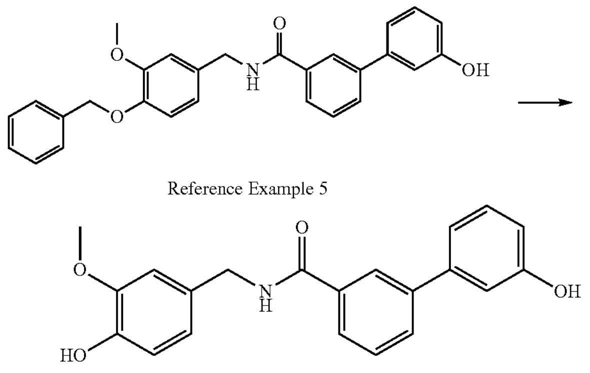

Reference Example 12

To a solution of N-{[4-(benzyloxy)-3-methoxyphenyl]methyl}-3'-hydroxy[1,1'-biphenyl]-3-carboxamide (250 mg) in ethyl acetate (10 ml) and ethanol (10 ml) was added palladium-activated carbon (Pd 20%) (50 mg), and the mixture was stirred under a hydrogen atmosphere at room temperature for 4 hours. The reaction solution was purged with nitrogen, then filtered through celite, and concentrated under reduced pressure, and the residue thus obtained was purified by silica gel column chromatography (eluting solution; hexane:ethyl acetate) to afford Reference Example 18 (171 mg).

LC-MS, m/z; 350.2 $(M+H)^+$ ESI, Rt; 0.684 (min)

Reference Examples 13 to 19

The compounds shown in Table 1 were obtained by the same method as in Reference Example 12, using corresponding raw material compounds.

TABLE 1

| Reference Example No. | Structural formula and LC-MS |
|---|---|
| 13 | 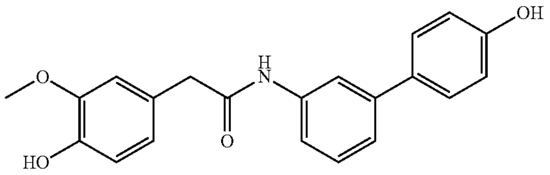 [SMILES: COc1cc(CC(=O)Nc2cccc(-c3ccc(O)cc3)c2)ccc1O] m/z; 350.1 $(M + H)^+$ ESI, Rt; 0.688 (min) |
| 14 | 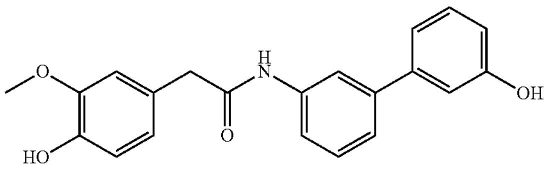 m/z; 350.4 $(M + H)^+$ ESI, Rt; 0.930 (min) |
| 15 | 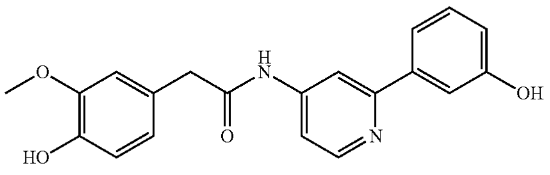 [SMILES: COc1cc(CC(=O)Nc2cccc(-c3cccc(O)c3)c2)ccc1O] m/z; 351.2 $(M + H)^+$ ESI, Rt; 0.415 (min) |
| 16 | 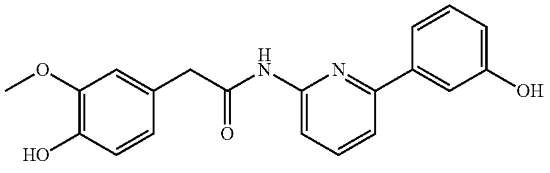 [SMILES: COc1cc(CC(=O)Nc2cccc(-c3cccc(O)c3)n2)ccc1O] m/z; 351.2 $(M + H)^+$ ESI, Rt; 0.684 (min) |

TABLE 1-continued

| Reference Example No. | Structural formula and LC-MS |
|---|---|
| 17 | 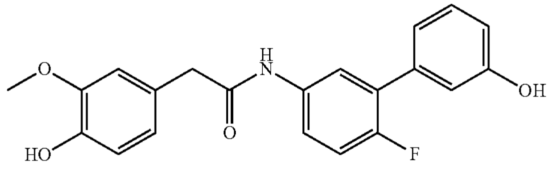 [SMILES: COc1cc(CC(=O)Nc2ccc(F)c(-c3cccc(O)c3)c2)ccc1O]<br>m/z; 368.1 (M + H)$^+$ ESI, Rt; 0.723 (min) |
| 18 | 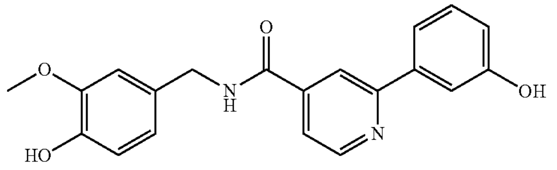 [SMILES: COc1cc(CNC(=O)c2ccnc(-c3cccc(O)c3)c2)ccc1O]<br>m/z; 351.2 (M + H)$^+$ ESI, Rt; 0.570 (min) |
| 19 | 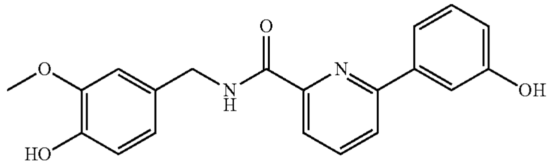 [SMILES: COc1cc(CNC(=O)c2cccc(-c3cccc(O)c3)n2)ccc1O]<br>m/z; 351.2 (M + H)$^+$ ESI, Rt; 0.680 (min) |

Example 2 cis-4-{3-[2-(4-Hydroxy-3-methoxyphenyl)acetamido]phenyl}cyclohexyl cyclohexanecarboxylate

[Chemical Formula 49]

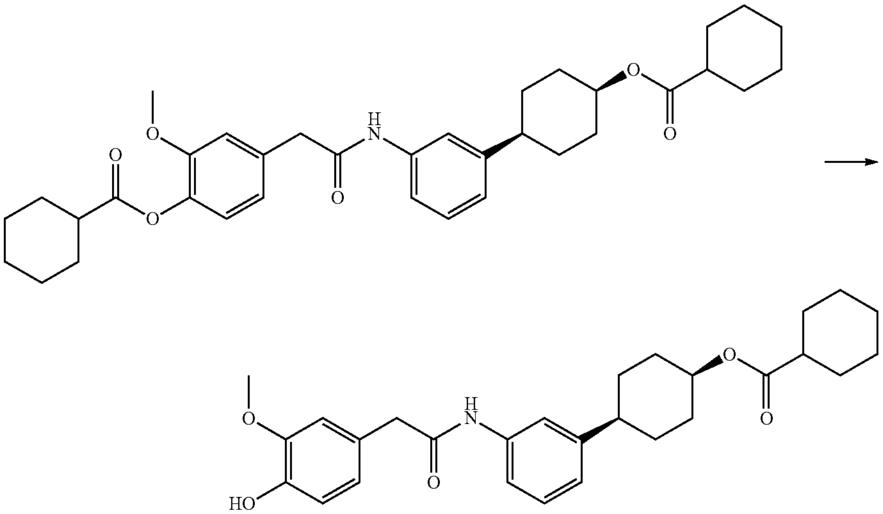

Example 2

To a solution of 4-[2-(3-{(cis)-4-[(cyclohexanecarbonyl)oxy]cyclohexyl}anilino)-2-oxoethyl]-2-methoxyphenyl cyclohexanecarboxylate (0.91 g) in 2-propanol (330 ml) was added 28 to 30% aqueous ammonia (110 ml). After stirring the mixture at room temperature for 1 day, 1 mol/L hydrochloric acid was added to the reaction solution, the mixture was extracted with ethyl acetate, and the obtained organic layer was washed with water and saturated saline solution. Thereafter, it was dried over sodium sulfate, filtered, and concentrated under reduced pressure, and the obtained solid was washed with diethyl ether and recrystallized from acetonitrile to afford Example 2 (469 mg).

$^1$H-NMR (400 MHz, $CD_3OD$) b: 7.45 (1H, t, J=1.8 Hz), 7.39-7.35 (1H, m), 7.22 (1H, t, J=7.6 Hz), 6.97 (1H, d, J=8.0 Hz), 6.94 (1H, d, J=1.2 Hz), 6.78 (1H, dd, J=2.0, 6.0 Hz), 6.75 (1H, d, J=8.0 Hz), 5.04 (1H, s), 3.86 (3H, s), 3.57 (2H, s), 2.63-2.54 (1H, m), 2.42-2.33 (1H, m), 2.00-1.89 (4H, m), 1.85-1.63 (9H, m), 1.55-1.43 (2H, m), 1.43-1.25 (3H, m).

LC-MS, m/z; 466.3 $(M+H)^+$ ESI, Rt; 1.134 (min)

Example 49

3-{4-[2-(4-Hydroxy-3-methoxyphenyl)acetamido]pyridin-2-yl}phenyl 2-methylpropanoate hydrochloride

[Chemical Formula 50]

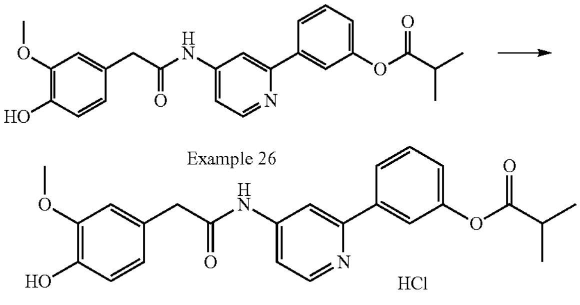

Example 26

Example 49

To a mixed solution of 3-{4-[2-(4-hydroxy-3-methoxyphenyl)acetamido]pyridin-2-yl}phenyl 2-methylpropanoate (2.5 g) in ethyl acetate (50 ml)/tetrahydrofuran (10 ml) was added 4 mol/L hydrogen chloride, ethyl acetate solution (10 ml), and the mixture was stirred under room temperature conditions. After concentrating the reaction solution, the obtained solid was washed with diethyl ether to afford Example 49 (1.97 g).

1H-NMR (400 MHz, $CD_3OD$) δ: 8.51 (111, d, J=6.4 Hz), 8.22 (111, d, J=2.0 Hz), 7.86 (1H, d, J=6.4 Hz), 7.75 (111, d, J=8.4 Hz), 7.63-7.58 (2H, m), 7.29 (1H, dd, J=2.6, 7.8 Hz), 6.94 (1H, d, J=1.6 Hz), 6.81-6.75 (2H, m), 3.86 (3H, s), 3.70 (2H, s), 2.87 (1H, p, J=7.0 Hz), 1.33 (6H, d, J=7.2 Hz).

LC-MS, m/z; 421.3 $(M+H)^+$ ESI, Rt; 0.707 (min)

Examples 3 to 48

The compounds shown in Table 2 were obtained by the same method as in Examples 1, 2, and 49, using corresponding raw material compounds.

TABLE 2

| Example No. | Structural formula and $^1$H-NMR |
|---|---|
| 3 | 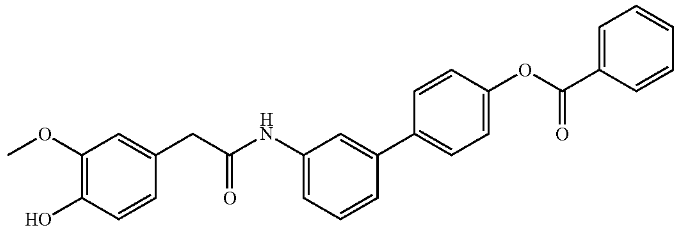 [SMILES: COc1cc(CC(=O)Nc2cccc(-c3ccc(OC(=O)c4ccccc4)cc3)c2)ccc1O] (400 MHz, $CD_3OD$) δ: 8.20 (2H, d, J = 8.0 Hz), 7.88 (1H, s), 7.73-7.67 (3H, m), 7.60-7.53 (3H, m), 7.43-7.38 (2H, m), 7.31 (2H, d, J = 8.8 Hz), 6.97 (1H, d, J = 2.0 Hz), 6.81 (1H, dd, J = 1.6, 8.0 Hz), 6.76 (1H, d, J = 8.4 Hz), 3.87 (3H, s), 3.61 (2H, s). |
| 4 | 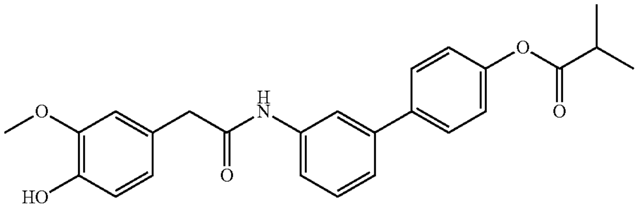 [SMILES: COc1cc(CC(=O)Nc2cccc(-c3ccc(OC(=O)C(C)C)cc3)c2)ccc1O] (400 MHz, $CD_3OD$) δ: 7.85 (1H. t, J = 2.2 Hz), 7.63 (2H, d, J = 8.8 Hz), 7.53 (1H, td, J = 2.1, 7.2 Hz), 7.40-7.33 (2H, m), 7.14 (2H, d, J = 8.4 Hz), 6.96 (1H, d, J = 2.0 Hz), 6.80 (1H, dd, J = 1.8, 8.0 Hz), 6.76 (1H, d, J = 8.0 Hz), 3.86 (3H, s), 3.61 (2H, s), 2.84 (1H, p, J = 7.1 Hz) 1.31 (6H, d, J = 6.8 Hz). |
| 5 | 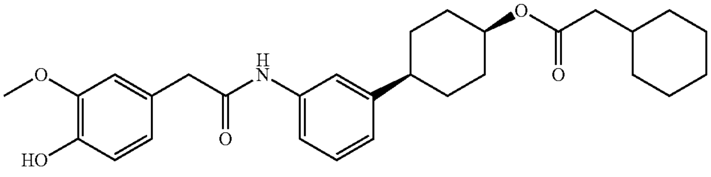 [SMILES: COc1cc(CC(=O)Nc2cccc([C@H]3CC[C@@H](OC(=O)CC4CCCCC4)CC3)c2)ccc1O] (400 MHz, $CD_3OD$) δ: 7.47 (1H, s), 7.35 (1H, d, J = 8.4 Hz), 7.22 (1H, t, J = 7.6 Hz), 6.97 (1H, d, J = 8.0 Hz), 6.94 (1H, s), 6.80-6.73 (2H, m), 5.06 (1H, s), 3.86 (3H, s), 3.57 (2H, s), 2.58 (1H, t, J = 11.8 Hz), 2.24 (2H, d, J = 7.2 Hz), 1.97 (2H, d, J = 11.6 Hz), 1.87-1.61 (12H, m), 1.37-1.11 (3H, m), 1.09-0.95 (2H, m). |

TABLE 2-continued

| Example No. | Structural formula and $^1$H-NMR |
|---|---|
| 6 | 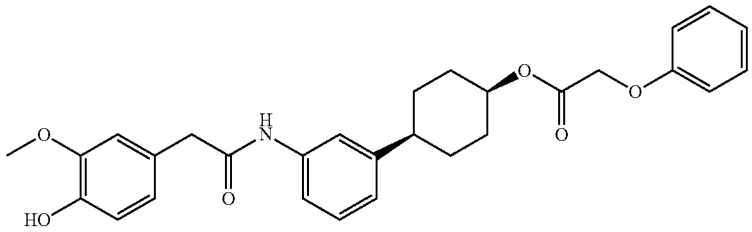 [SMILES: COc1cc(CC(=O)Nc2cccc([C@H]3CC[C@@H](OC(=O)COc4ccccc4)CC3)c2)ccc1O] (400 MHz, $CDCl_3$) δ: 7.21-7.09 (5H, m), 7.05 (1H, s), 6.91-6.83 (4H, m), 6.77-6.72 (3H, m), 5.61 (1H, brs) 5.15 (1H, s), 4.61 (2H, s), 3.82 (3H, s), 3.59 (2H, s), 2.45-2.35 (1H, m), 1.92 (2H, d, J = 10.4 Hz), 1.59-1.45 (6H, m). |
| 7 | 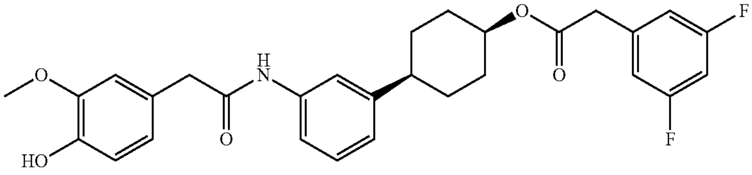 [SMILES: COc1cc(CC(=O)Nc2cccc([C@H]3CC[C@@H](OC(=O)Cc4cc(F)cc(F)c4)CC3)c2)ccc1O] (400 MHz, $CD_3OD$) δ: 7.41 (1H, t, J = 1.8 Hz), 7.34 (1H, td, J = 1.2, 8.0 Hz), 7.21 (1H, t, J = 8.0 Hz), 6.99-6.94 (3H, m), 6.90 (1H, d, J = 8.0 Hz), 6.86-6.74 (3H, m), 5.07 (1H, s), 3.85 (3H, s), 3.74 (2H, s), 3.58 (2H, s), 2.57-2.52 (1H, m), 1.96-1.93 (2H, m), 1.72-1.60 (6H, m). |
| 8 | 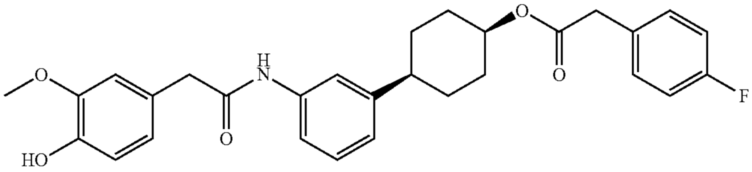 [SMILES: COc1cc(CC(=O)Nc2cccc([C@H]3CC[C@@H](OC(=O)Cc4ccc(F)cc4)CC3)c2)ccc1O] (400 MHz, $CD_3OD$) δ: 7.45 (1H, t, J = 1.8 Hz), 7.37-7.28 (3H, m), 7.21 (1H, t, J = 7.6 Hz), 7.07-7.02 (2H, m), 6.95 (1H, d, J = 2.0 Hz), 6.86 (1H, d, J = 7.6 Hz), 6.80 (1H, dd, J = 1.8, 8.6 Hz), 6.75 (1H, d, J = 8.0 Hz), 5.04 (1H, s), 3.85 (3H, s), 3.67 (2H, s), 3.59 (2H, s), 2.59-2.47 (1H, m), 1.96-1.90 (2H, m), 1.70-1.56 (6H, m). |
| 9 | 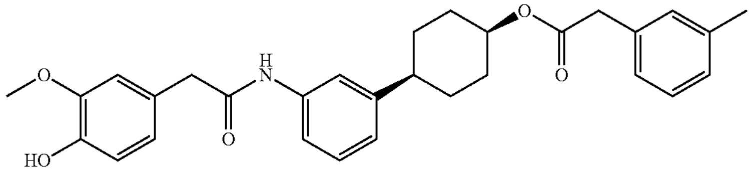 (400 MHz, $CD_3OD$) δ: 7.40 (1H, t, J = 1.8 Hz), 7.35-7.31 (1H, m), 7.23-7.09 (4H, m), 7.03 (1H, d, J = 7.6 Hz), 6.96 (1H, d, J = 1.6 Hz), 8.85 (1H, d, J = 8.0 Hz), 6.80 (1H, dd, J = 1.6, 8.0 Hz), 6.76 (1H, d, J = 8.4 Hz), 5.02 (1H, s), 3.85 (3H, s), 3.62 (2H, s), 3.58 (2H, s), 2.57-2.45 (1H, m), 2.28 (3H, s), 1.96-1.88 (2H, m), 1.70-1.55 (6H, m). |
| 10 | 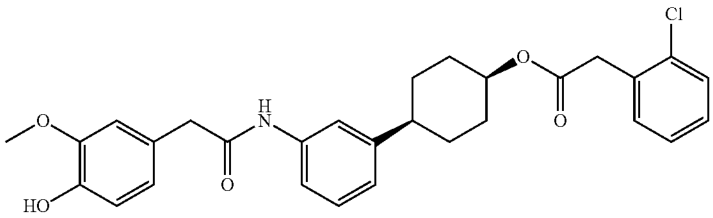 (400 MHz, $CD_3OD$) δ: 7.41-7.36 (2H, m), 7.33-7.17 (5H, m), 6.96 (1H, s), 6.82-6.74 (3H, m), 5.06 (1H, s), 3.86-3.83 (5H, m), 3.58 (2H, s), 2.54-2.44 (1H, m), 1.97-1.88 (2H, m), 1.69-1.49 (6H, m). |

TABLE 2-continued

| Example No. | Structural formula and $^{1}$H-NMR |
|---|---|
| 11 | 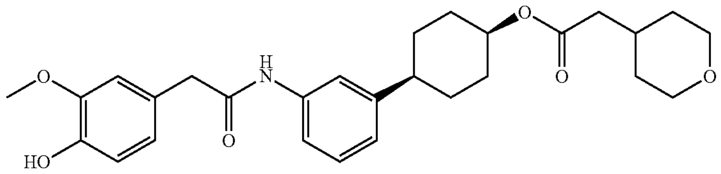 [SMILES: COc1cc(CC(=O)Nc2cccc([C@H]3CC[C@@H](OC(=O)CC4CCOCC4)CC3)c2)ccc1O] (400 MHz, $CD_3OD$) δ: 7.50 (1H, t, J = 1.8 Hz), 7.35-7.32 (1H, m), 7.21 (1H, t, J = 7.8 Hz), 6.97 (1H, d, J = 7.6 Hz), 6.94 (1H, J = 1,6 Hz), 6.69 (1H, dd, J = 1.8, 8,2 Hz), 6.75 (1H, d, 7.6 Hz), 5.08 (1H, s), 3.92 (2H, dd, J = 3.4, 10.6 Hz), 3.86 (3H, s), 3.57 (2H, s), 3,43 (2H, dt, J = 2.0, 7.8 Hz), 2.64-2.54 (1H, m), 2.32 (2H, d, J = 7.2 Hz), 2.11-1.93 (3H, m), 1.83-1.64 (8H, m), 1.42-1.28 (2H, m) |
| 12 | 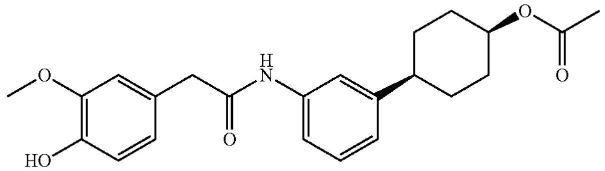 [SMILES: COc1cc(CC(=O)Nc2cccc([C@H]3CC[C@@H](OC(C)=O)CC3)c2)ccc1O] (400 MHz, $CD_3OD$) δ: 7.45 (1H, s), 7.37 (1H, d, J = 8.0 Hz), 7.21 (1H. t, J = 7.8 Hz), 6.98 (1H, d, J = 8.0 Hz), 6.94 (1H, d, J = 2.0 Hz), 6.78 (1H, dd, J = 1.6, 8.0 Hz), 6,75 (1H, d, J = 8.0 Hz), 5.05 (1H, s), 3.86 (3H, s), 3.57 (2H, s), 2.63-2.53 (1H, m), 2.08 (3H, s), 1.98 (2H, d, J = 10 Hz), 1.83-1.65 (6H, m). |
| 13 | 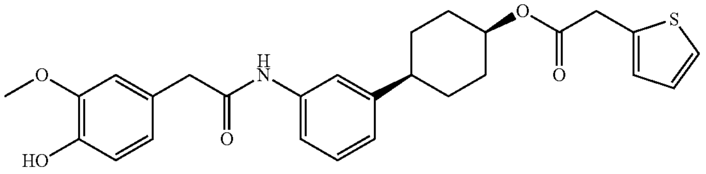 [SMILES: COc1cc(CC(=O)Nc2cccc([C@H]3CC[C@@H](OC(=O)Cc4cccs4)CC3)c2)ccc1O] (400 MHz, $CD_3OD$) δ: 7.44 (1H, t, J = 1.8 Hz), 7.33-7.30 (1H, m), 7.24-7.18 (2H, m), 6.99-6.95 (2H, m), 6.94-6.90 (2H, m), 6.80 (1H, dd, J = 1.8, 8.2 Hz), 6.76 (1H, d, J = 7.6 Hz), 5.06 (1H, s), 3.90 (2H, s), 3.85 (3H, s), 3.58 (2H, s), 2.57-2.49 (1H, m), 2.00-1.92 (2H, m), 1.73-1.59 (6H, m) |
| 14 | 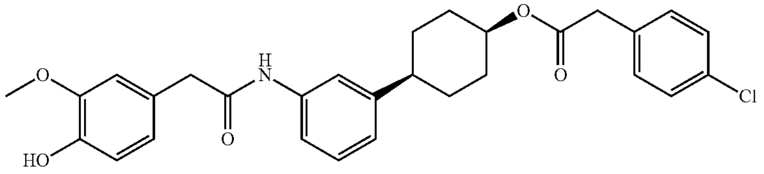 [SMILES: COc1cc(CC(=O)Nc2cccc([C@H]3CC[C@@H](OC(=O)Cc4ccc(Cl)cc4)CC3)c2)ccc1O] (400 MHz, $CD_3OD$) δ: 7.45 (1H, t, J = 2.0 Hz), 7.33-7.28 (5H, m), 7.22 (1H, t, J = 7.8 Hz), 6.95 (1H, d, J = 2.0 Hz), 6.84 (1H, d, J = 7.2 Hz), 6.80 (1H, dd, J = 2.0, 8.4 Hz), 6.75 (1H, d, J = 8.4 Hz), 5.04 (1H, s), 3.85 (3H, s), 3.68 (2H, s), 3.59 (2H, s), 2.56-2.47 (1H, m), 1.96-1.89 (2H, m), 1.69-1.55 (6H, m) |
| 15 | 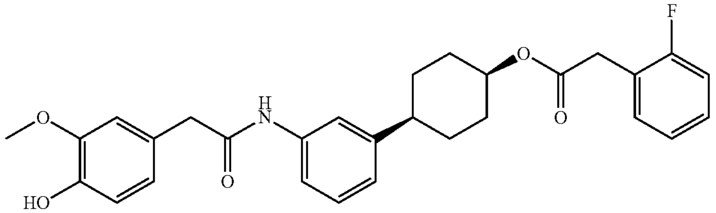 [SMILES: COc1cc(CC(=O)Nc2cccc([C@H]3CC[C@@H](OC(=O)Cc4ccccc4F)CC3)c2)ccc1O] (400 MHz, $CD_3OD$) δ: 7.37-7.31 (3H, m), 7.27-7.18 (2H, m), 7.13-7.05 (2H, m), 6.96 (1H, d, J = 1.6 Hz), 6.84-6.75 (3H, m), 5.05 (1H, s), 3.85 (3H, s), 3.74 (2H, d, J = 1.2 Hz), 3.58 (2H, s), 2.54-2.46 (1H, m), 1.97-1.89 (2H, m), 1.70-1.53 (6H, m). |

TABLE 2-continued

| Example No. | Structural formula and $^{1}$H-NMR |
| --- | --- |
| 16 | 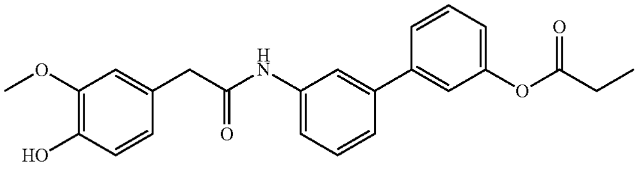 [SMILES: CCC(=O)Oc1cccc(-c2cccc(NC(=O)Cc3ccc(O)c(OC)c3)c2)c1] (400 MHz, $CD_3OD$) δ: 7.85 (1H, s), 7.56-7.31 (6H, m), 7.09-7.05 (1H, m), 6.95 (1H, m), 6.82-6.73 (2H, m), 3.85 (3H, s), 3.60 (2H, s), 2.63 (2H, q, J = 7.6 Hz), 1.26-1.21 (3H, m). |
| 17 | 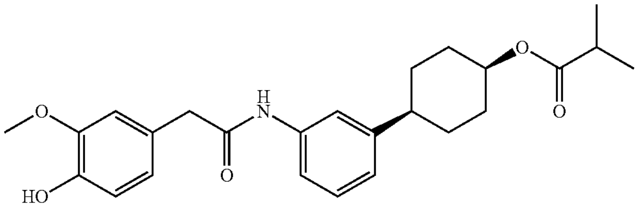 [SMILES: COc1cc(CC(=O)Nc2cccc([C@H]3CC[C@@H](OC(=O)C(C)C)CC3)c2)ccc1O] (400 MHz, $CD_3OD$) δ: 7.44 (1H, t, J = 1.8 Hz), 7.39-7.36 (1H, m), 7.21 (1H, t, J = 8.0 Hz), 6.97 (1H, d, J = 8.0 Hz), 6.94 (1H, d, J = 1.6 Hz), 6.78 (1H, dd, J = J = 2.2, 8.2 Hz), 6.75 (1H, d, J = 8.4 Hz), 5.04 (1H, s), 3.86 (3H, s), 3.57 (2H, s), 2.64-2.55 (2H, m), 2.01-1.94 (2H, m), 1.82-1.66 (6H, m), 1.20 (6H, d, J = 7.2 Hz). |
| 18 | 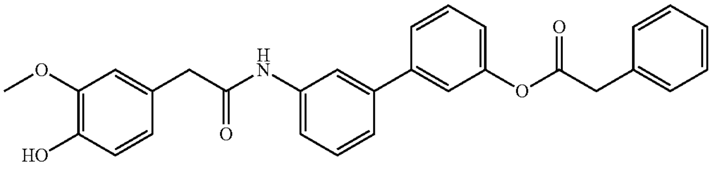 [SMILES: COc1cc(CC(=O)Nc2cccc(-c3cccc(OC(=O)Cc4ccccc4)c3)c2)ccc1O] (400 MHz, $CD_3OD$) δ: 7.83 (1H, t, J = 1.8 Hz), 7.57-7.53 (1H, m), 7.50-7.27 (10H, m), 7.07-7.03 (1H, m), 6.95 (1H, d, J = 2.0 Hz), 6.79 (1H, dd, J = 2.0, 8.0 Hz), 6.76 (1H, d, J = 7.6 Hz), 3.93 (2H, s), 3.86 (3H, s), 3.60 (2H, s). |
| 19 | 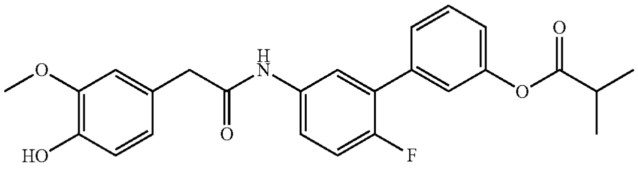 [SMILES: COc1cc(CC(=O)Nc2ccc(F)c(-c3cccc(OC(=O)C(C)C)c3)c2)ccc1O] (400 MHz, $CDCl_3$) δ: 7.45 (1H, s), 7.39-7.22 (4H, m), 7.13 (1H, d, J = 2.0 Hz), 7.00-6.90 (2H, m), 6.80 (1H, d, J = 7.4 Hz), 6.73-6.65 (2H, m), 5.78 (1H, s), 3.75 (3H, s), 3.52 (2H, s), 2.73 (1H, p, J = 6.9 Hz), 1.23 (6H, d, J = 6.8 Hz). |
| 20 | 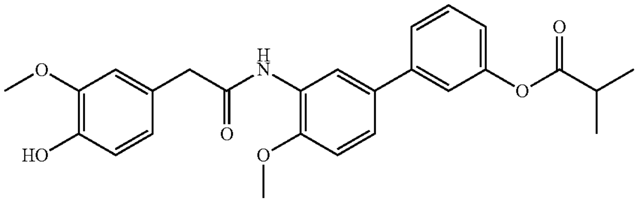 [SMILES: COc1cc(CC(=O)Nc2cc(-c3cccc(OC(=O)C(C)C)c3)ccc2OC)ccc1O] (400 MHz, $CDCl_3$) δ: 8.57 (1H, d, J = 2.4 Hz), 7.81 (1H, s), 7.35 (1H, td, J = 1.2, 7.6 Hz), 7.30 (1H, t, J = 7.8 Hz), 7.19 (1H, t, J = 1.8 Hz), 7.16 (1H, dd, J = 2.2, 8.2 Hz), 6.94-6.91 (1H, m), 6.87 (1H, d, J = 8.4 Hz), 6.79-6.74 (3H, m), 5.65 (1H, s), 3.82 (3H, s), 3.69 (3H, s), 3.61 (2H, s), 2.74 (1H, p, J = 7.0 Hz), 1.25 (6H, d, J = 6.8 Hz). |

TABLE 2-continued

| Example No. | Structural formula and $^1$H-NMR |
| --- | --- |
| 21 | 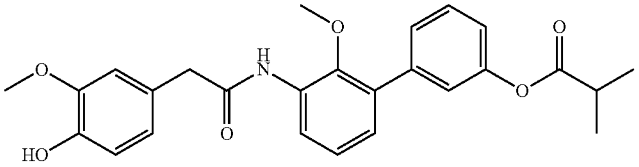 [SMILES: COc1cc(CC(=O)Nc2cccc(-c3cccc(OC(=O)C(C)C)c3)c2OC)ccc1O] (400 MHz, $CDCl_3$) δ: 8.29 (1H, dd, J = 1.6, 8.0 Hz), 7.94 (1H, s), 7.32 (1H, t, J = 7.8 Hz), 7.27 (1H, td, J = 1.4, 8.0 Hz), 7.15 (1H, t, J = 1.8 Hz), 7.05 (1H, t, J = 8.0 Hz), 6.99-6.93 (2H, m), 6.88 (1H, d, J = 8.4 Hz), 6.80-6.75 (2H, m), 5.65 (1H, s), 3.81 (3H, s), 3.63 (2H, s), 3.02 (3H, s), 2.73 (1H, p, J = 6.9 Hz), 1.24 (6H, d, J = 7.2 Hz). |
| 22 | 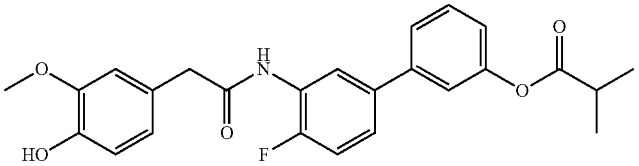 [SMILES: COc1cc(CC(=O)Nc2cc(-c3cccc(OC(=O)C(C)C)c3)ccc2F)ccc1O] (400 MHz, $CDCl_3$) δ: 8.46 (1H, dd, J = 2.4, 7.6 Hz), 7.43 (1H, s), 7.34-7.31 (2H, m), 7.19-7.12 (2H, m), 7.02-6.94 (2H, m), 6.86 (1H, d, J = 8.8 Hz), 6.77-6.73 (2H, m), 5.66 (1H, s), 3.82 (3H, s), 3.63 (2H, s), 2.47 (1H, p, J = 7.0 Hz), 1.25 (6H, d, J = 7.2 Hz). |
| 23 | 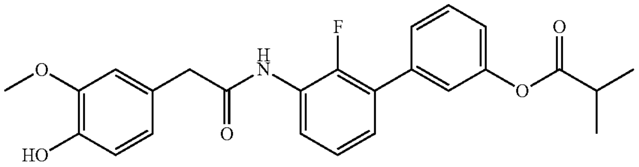 [SMILES: COc1cc(CC(=O)Nc2cccc(-c3cccc(OC(=O)C(C)C)c3)c2F)ccc1O] (400 MHz, $CDCl_3$) δ: 8.21 (1H, t, J = 7.6 Hz), 7.49 (1H, s), 7.33 (1H, t, J = 7.8 Hz), 7.23 (1H, dd, J = 1.0, 7.8 Hz), 7.12-6.97 (4H, m), 6.85 (1H, d, J = 8.4 Hz), 6.77-6.72 (2H, m), 5.71 (1H, s), 3.79 (3H, s), 3.62 (2H, s), 2.73 (1H, p, J = 7.0 Hz), 1.24 (6H, d, J = 7.2 Hz). |
| 24 | 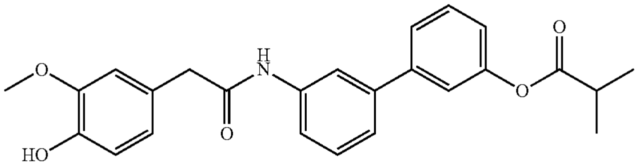 [SMILES: COc1cc(CC(=O)Nc2cccc(-c3cccc(OC(=O)C(C)C)c3)c2)ccc1O] (400 MHz, $CD_3OD$) δ: 7.86-7.84 (1H, m), 7.55 (1H, td, J = 1.8, 8.0 Hz), 7.51-7.43 (2H, m), 7.41-7.33 (2H, m), 7.30 (1H, t, J = 1.8 Hz), 7.08-7.04 (1H, m), 6.96 (1H, d, J = 2.0 Hz), 6.80 (1H, dd, J = 2.0, 8.0 Hz), 6.76 (1H, d, J = 7.6 Hz), 3.86 (3H, s), 3.60 (2H, s), 2.85 (1H, p, J = 7.0 Hz) 1.32 (6H, d, J = 7.2 Hz). |
| 25 | 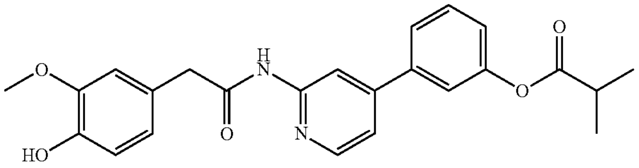 [SMILES: COc1cc(CC(=O)Nc2cc(-c3cccc(OC(=O)C(C)C)c3)ccn2)ccc1O] (400 MHz, $CDCl_3$) δ: 8.43 (1H, s), 8.18 (1H, dd, J = 0.4, 5.2 Hz), 8.02 (1H, s), 7,46 (1H, td, J = 1.5, 8.0 Hz), 7.39 (1H, t, J = 7.8 Hz), 7.30 (1H, t, J = 2.0 Hz), 7.17 (1H, dd, J = 1.4, 5.6 Hz), 7.10-7.06 (1H, m), 6.84 (1H, d, J = 8.0 Hz), 6.77-6.73 (2H, m), 6.09 (1H, s), 3.78 (3H, s), 3.63 (2H, s), 2.76 (1H, p, J = 7.0 Hz), 1.27 (6H, d, J = 7.2 Hz). |

TABLE 2-continued

| Example No. | Structural formula and ¹H-NMR |
|---|---|
| 26 | 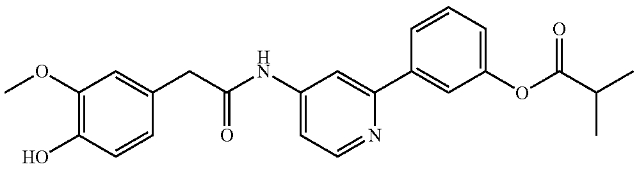 [SMILES: COc1cc(CC(=O)Nc2ccnc(-c3cccc(OC(=O)C(C)C)c3)c2)ccc1O]<br>(400 MHz, CDCl3) δ: 8.51 (1H, d, J = 6.0 Hz), 7.80-7.76 (2H, m), 7.68 (1H, t, J = 1.8 Hz), 7.42 (1H, t, J = 8.0 Hz), 7.32 (1H, dd, J = 1.8, 5.8 Hz), 7.27 (1H, s), 7.11-7.09 (1H, m), 6.95 (1H, d, J = 7.6 Hz), 6.84-6.79 (2H, m), 5.67 (1H, s), 3.90 (3H, s), 3.69 (2H, s), 2.82-2.78 (1H, m), 1.31 (6H, d, J = 6.8 Hz). |
| 27 | 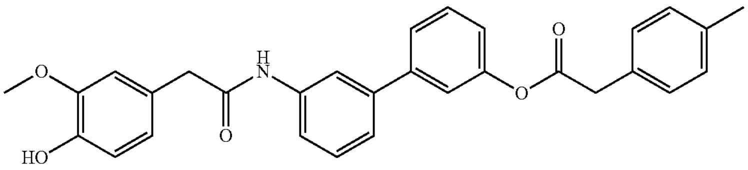<br>(400 MHz, $CD_3OD$) δ: 7.82 (1H, s), 7.55 (1H, d, J = 8.0 Hz), 7.49-7.25 (7H, m), 7.17 (2H, d, J = 8.0 Hz), 7.06-7.02 (1H, m), 6.95 (1H, d, J = 1.2 Hz), 6.81-6.74 (2H, m), 3.87 (2H, s), 3.86 (3H, s), 3.60 (2H, s), 2.33 (3H, s). |
| 28 | 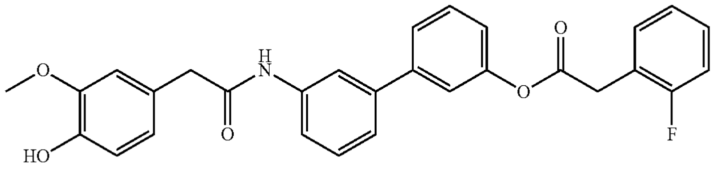 [SMILES: COc1cc(CC(=O)Nc2cccc(-c3cccc(OC(=O)Cc4ccccc4F)c3)c2)ccc1O]<br>(400 MHz, $CD_3OD$) δ: 7.83 (1H, t, J = 18 Hz), 7.57-7.53 (1H, m), 7.50-7.30 (7H, m), 7.20-7.05 (2H, m), 6.95 (1H, d, J = 2.0 Hz), 6.82-6.74 (2H, m), 3.99 (2H, s), 3.85 (3H, s), 3.60 (2H, s). |
| 29 | 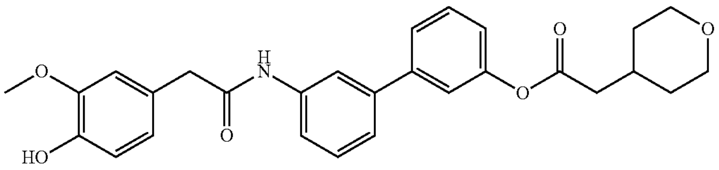 [SMILES: COc1cc(CC(=O)Nc2cccc(-c3cccc(OC(=O)CC4CCOCC4)c3)c2)ccc1O]<br>(400 MHz, $CD_3OD$) δ: 7.86-7.85 (1H, m), 7.56-7.30 (6H, m), 7.09-7.05 (1H, m), 6.96 (1H, d, J = 1.2 Hz), 6.82-6.74 (2H, m), 3.95 (2H, dd, J = 3.4, 10.6 Hz), 3.86 (3H, s), 3.60 (2H, s), 3.47 (2H, dt, J = 2.1, 11.6 Hz), 2.56 (2H, d, J = 6.8 Hz), 2.20-2.10 (1H, m), 1.81-1.74 (2H, m), 1.49-1.37 (2H, m). |
| 30 | 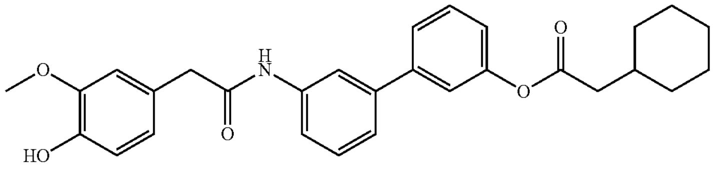 [SMILES: COc1cc(CC(=O)Nc2cccc(-c3cccc(OC(=O)CC4CCCCC4)c3)c2)ccc1O]<br>(400 MHz, $CD_3OD$) δ: 7.84 (1H, t, J = 1.8 Hz), 7.55 (1H, td, J = 1.6, 8.0 Hz), 7.51-7.33 (4H, m), 7.29 (1H, t, J = 1.8 Hz), 7.07-7.03 (1H, m), 6.96 (1H, d, J = 2.0 Hz), 6.80 (1H, dd, J = 2.0, 8.0 Hz), 6.76 (1H, d, J = 7.6 Hz), 3.86 (3H, s), 3.60 (2H, s), 2.48 (2H, d, J = 6.8 Hz), 1.95-1.82 (3H, m), 1.80-1.67 (3H, m), 1.40-1.20 (3H, m), 1.16-1.06 (2H, m). |

TABLE 2-continued

| Example No. | Structural formula and $^1$H-NMR |
|---|---|
| 31 | 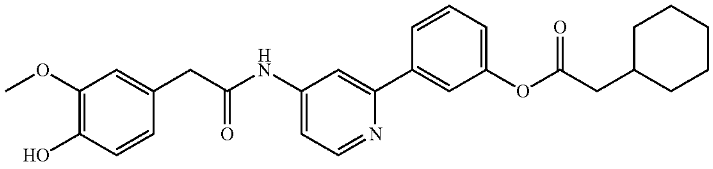 [SMILES: COc1cc(CC(=O)Nc2ccnc(-c3cccc(OC(=O)CC4CCCCC4)c3)c2)ccc1O] (400 MHz, $CDCl_3$) δ: 8.45 (1H, d, J = 6.0 Hz), 7.82 (1H, d, J = 1.6 Hz), 7.76-7.64 (3H, m), 7.40 (1H, t, J = 8.0 Hz), 7.32 (1H, dd, J = 2.0, 6.0 Hz), 7.11-7.07 (1H, m), 6.91 (1H, d, J = 8.8 Hz), 6.81-6.77 (2H, m), 3.86 (3H, s), 3.66 (2H, s), 2.42 (2H, d, J = 6.8 Hz), 1.96-1.78 (3H, m), 1.75-1.62 (3H, m), 1.35-1.00 (5H, m). |
| 32 | 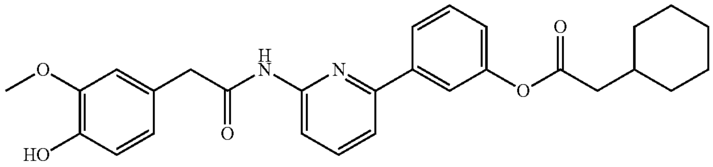 [SMILES: COc1cc(CC(=O)Nc2cccc(-c3cccc(OC(=O)CC4CCCCC4)c3)n2)ccc1O] (400 MHz, $CDCl_3$) δ: 8.16 (1H, d, J = 8.4 Hz), 8.03 (1H, brs), 7.74-7.71 (2H, m), 7.61 (1H, t, J = 2.0 Hz), 7.43-7.39 (2H, m), 7.11-7.07 (1H, m), 6.91 (1H, d, J = 8.8 Hz), 6.83-6.80 (2H, m), 5.70 (1H, s), 3.87 (3H, s), 3.66 (2H, s), 2.43 (2H, d, J = 6.8 Hz), 1.96-1.82 (3H, m), 1.77-1.64 (3H, m), 1.37-1.14 (3H, m), 1.12-1.01 (2H, m). |
| 33 | 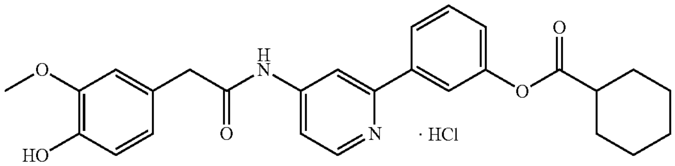 [SMILES: COc1cc(CC(=O)Nc2ccnc(-c3cccc(OC(=O)C4CCCCC4)c3)c2)ccc1O] (400 MHz, $CD_3OD$) δ: 8.56 (1H, d, J = 6.4 Hz), 8.32 (1H, d, J = 2.0 Hz), 8.06 (1H, dd, J = 2.4, 6.8 Hz), 7.74-7.71 (1H, m), 7.67 (1H, t, J = 8.0 Hz), 7.61 (1H, t, J = 1.8 Hz), 7.38 (1h, ddd, J = 1.2, 2.4, 8.0 Hz), 6.94 (1H, d, J = 1.2 Hz), 6.81-6.75 (2H, m), 3.86 (3H, s), 3,74 (2H, s), 2.70-2.61 (1H, m), 2.12-2.04 (2H, m), 1.88-1.80 (2H, m), 1.76-1.68 (1H, m), 1.66-1.55 (2H, m), 1.49-1.27 (3H, m). |
| 34 | 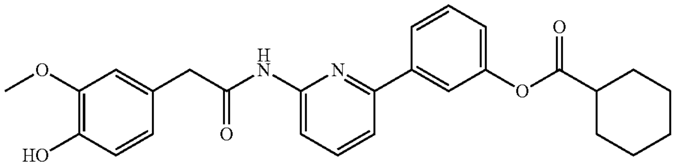 [SMILES: COc1cc(CC(=O)Nc2cccc(-c3cccc(OC(=O)C4CCCCC4)c3)n2)ccc1O] (400 MHz, $CDCl_3$) δ: 8.16 (1H, d, J = 8.4 Hz), 8.09 (1H, brs), 7.76-7.70 (2H, m), 7.60 (1H, t, J = 2.0 Hz), 7.44-7.39 (2H, m), 7.08 (1H, dd, J = 2.4, 8.0 Hz), 6.91 (1H, d, J = 8.4 Hz), 6.85-6.81 (2H, m), 5.65 (1H, s), 3,88 (3H, s), 3.67 (2H, s), 2.56 (1H, tt, J = 3.6, 11.2 Hz), 2.11-2.02 (2H, m), 1.85-1.77 (2H, m), 1.72-1.66 (1H, m), 1.64-1.53 (2H, m), 1.42-1.26 (3H, m). |
| 35 | 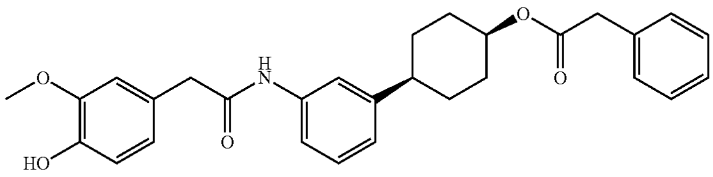 [SMILES: COc1cc(CC(=O)Nc2cccc([C@H]3CC[C@@H](OC(=O)Cc4ccccc4)CC3)c2)ccc1O] (400 MHz, $CDCl_3$) δ: 7.27-7.21 (4H, m), 7.17-7.12 (4H, m), 7.05 (1H, brs), 6.88 (1H, d, J = 8.0 Hz), 6.81-6.74 (3H, m), 5.61 (1H, brs), 5.01 (1H, s), 3.82 (3H, s), 3.60 (2H, s), 3.58 (2H, s), 2.44-2.35 (1H, m), 1.92-1.81 (2H, m), .157-1.45 (6H, m). |

TABLE 2-continued

| Example No. | Structural formula and $^1$H-NMR |
| --- | --- |
| 36 | 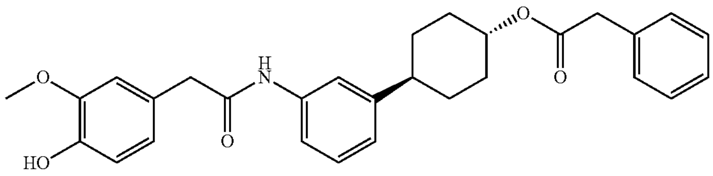 [SMILES: COc1cc(CC(=O)Nc2cccc([C@H]3CC[C@H](OC(=O)Cc4ccccc4)CC3)c2)ccc1O]<br>(400 MHz, $CD_3OD$) δ: 7.41 (1H, s), 7.37-7.16 (7H, m), 6.99-6.92 (2H, m), 6.79-6.72 (2H, m), 4.80-4.71 (1H, m), 3.85 (3H, s), 3.61 (2H, s). 3..56 (2H, s), 2.56-2.46 (1H, m), 2.09-2.00 (2H, m), 1.95-1.87 (2H, m), 1.65-1.45 (4H, m). |
| 37 | 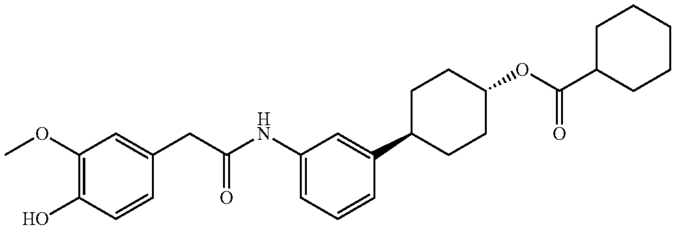 [SMILES: COc1cc(CC(=O)Nc2cccc([C@H]3CC[C@H](OC(=O)C4CCCCC4)CC3)c2)ccc1O]<br>(400 MHz, DMSO-$d_6$) δ: 9.67 (1H, s), 8.79 (1H, s), 7.48 (1H, s), 7.38 (1H, d, J = 8.0 Hz), 7.18 (1H, t, J = 8.0 Hz), 6.93-6.87 (2H, m), 6.69 (2H, s), 4.71-4.60 (1H, m), 3.74 (3H, s), 3.47 (2H, s), 2.30-2.22 (1H, m), 1.99-1.91 (2H, m), 1.85-1.74 (4H, m), 1.68-1.21 (12H, m). |
| 38 | 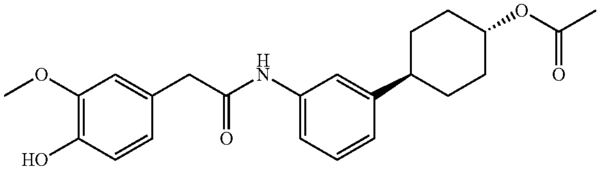 [SMILES: COc1cc(CC(=O)Nc2cccc([C@H]3CC[C@H](OC(C)=O)CC3)c2)ccc1O]<br>(400 MHz, DMSO-$d_6$) δ: 9.67 (1H, s), 8.79 (1H, s), 7.48 (1H, s), 7.37 (1H, d, J = 8.4 Hz), 7.18 (1H, t, J = 8.0 Hz), 6.92-6.88 (2H, m), 6.69 (2H, s), 4.70-4.60 (1H, m), 3.74 (3H, s), 3.47 (2H, s), 2.01-1.92 (5H, m), 1.84-1.77 (2H, m), 1.53-1.43 (4H, m). |
| 39 | 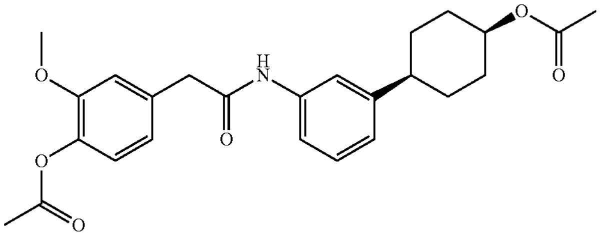 [SMILES: COc1cc(CC(=O)Nc2cccc([C@H]3CC[C@@H](OC(C)=O)CC3)c2)ccc1OC(C)=O]<br>(400 MHz, $CD_3OD$) δ: 7.46 (1H, t, J = 2.0 Hz), 7.39-7.35 (1H, m), 7.22 (1H, t, J = 7.6 Hz), 7.10 (1H, d, J = 2.0 Hz), 6.99 (1H, d, J = 8.0 Hz), 6.93 (1H, dd, J = 2.0, 8.0 Hz), 5.07-5.03 (1H, m), 3,83 (3H, s), 3.67 (2H, s), 2.63-2.54 (1H, m), 2.25 (3H, s), 2.08 (3H, s), 2.02-1.95 (2H, m), 1.86-1.65 (6H, m). |
| 40 | 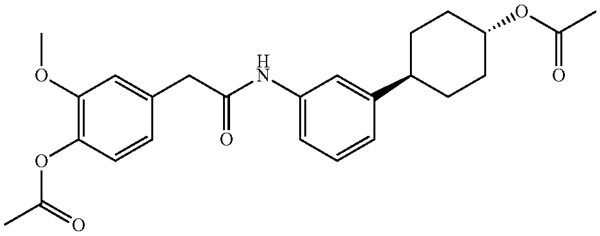 [SMILES: COc1cc(CC(=O)Nc2cccc([C@H]3CC[C@H](OC(C)=O)CC3)c2)ccc1OC(C)=O]<br>(400 MHz, $CD_3OD$) δ: 7.43 (1H, t, J = 2.2 Hz), 7.39-7.35 (1H, m), 7.21 (1H, t, J = 8.0 Hz), 7.10 (1H, d, J = 2.0 Hz), 6.98 (1H, d, J = 8.8 Hz), 6.93 (1H, dd, J = 1.8, 7.8 Hz), 4.78-4.69 (1H, m), 3.83 (3H, s), 3.67 (2H, s), 2.57-2.48 (1H, m), 2.25 (3H, s), 2.11-2.05 (2H, m), 2.02 (3H, s), 1.96-1.88 (2H, m), 1.66-1.46 (4H, m). |

TABLE 2-continued

| Example No. | Structural formula and $^1$H-NMR |
| --- | --- |
| 41 | 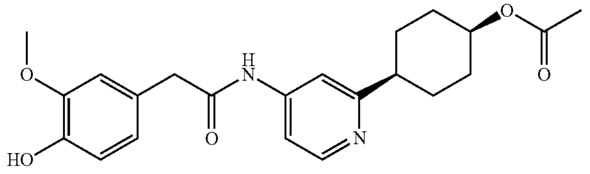 [SMILES: COc1cc(CC(=O)Nc2ccnc([C@H]3CC[C@@H](OC(C)=O)CC3)c2)ccc1O] (400 MHz, $CD_3OD$) δ: 8.28 (1H, d, J = 5.6 Hz), 7.58 (1H, d, J = 1.6 Hz), 7.50-7.44 (1H, m), 6.92 (1H, s), 6.77-6.75 (2H, m), 5.08-5.04 (1H, m), 3.90 (3H, s), 3.61 (2H, s), 2.78-2.69 (1H, m), 2.08 (3H, s), 2.04-1.66 (8H, m). |
| 42 | 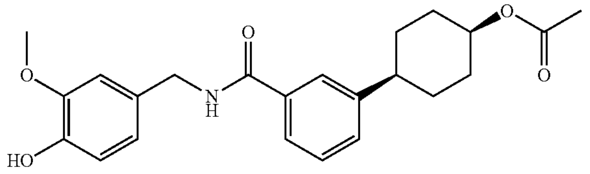 [SMILES: COc1cc(CNC(=O)c2cccc([C@H]3CC[C@@H](OC(C)=O)CC3)c2)ccc1O] (400 MHz, $CD_3OD$) δ: 7.74 (1H, t, J = 1.8 Hz), 7.67-7.63 (1H, m), 7.44-7.35 (2H, m), 6.96 (1H, d, J = 1.6 Hz), 6.80 (1H, dd, J = 1.6, 7.8 Hz), 6.75 (1H, d, J = 8.0 Hz), 5.06 (1H, s), 4..48 (2H, s), 3.84 (3H, s), 2.73-2.64 (1H, m), 2.08 (3H, s), 2.04-1.97 (2H, m), 1.92-1.67 (6H, m). |
| 43 | 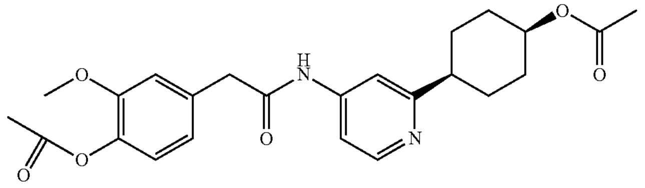 [SMILES: COc1cc(CC(=O)Nc2ccnc([C@H]3CC[C@@H](OC(C)=O)CC3)c2)ccc1OC(C)=O] (400 MHz, $CD_3OD$) δ: 8.29 (1H, d, J = 5.6 Hz), 7.58 (1H, d, J = 2.0 Hz), 7.49-7.45 (1H, m), 7.08 (1H, d, J = 2.0 Hz), 6.99 (1H, d, J = 8.4 Hz), 6.92 (1H, dd, J = 2.0, 8.0 Hz), 5.08-5.04 (1H, m), 3.83 (3H, s), 3.72 (2H, s), 2.79-2.69 (1H, m), 2.25 (3H, s), 2.08 (3H, s), 2.04-1.96 (2H, m), 1.94-1.82 (2H, m), 1.79-1.67 (4H, m). |
| 44 | 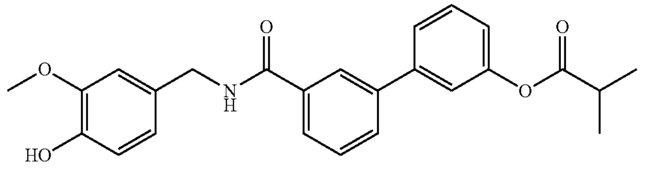 [SMILES: COc1cc(CNC(=O)c2cccc(-c3cccc(OC(=O)C(C)C)c3)c2)ccc1O] (400 MHz, $CD_3OD$) δ: 8.10 (1H, t, J = 1.6 Hz), 7.82 (1H, td, J = 1.6, 8.4 Hz), 7.82-7.79 (1H, m), 7.59-7.53 (2H, m), 7.49 (1H, t, J = 7.8 Hz), 7.40 (1H, t, J = 1.8 Hz), 7.11-7.07 (1H, m), 6.97 (1H, d, J = 2.0 Hz), 6.82 (1H, dd, J = 1.8, 8.2 Hz), 6.76 (1H, d, J = 8.0 Hz), 4.51 (2H, s), 3.84 (3H, s), 2.85 (1H, p, J = 7.1 Hz), 1.32 (6H, d, J = 6.8 Hz). |
| 45 | 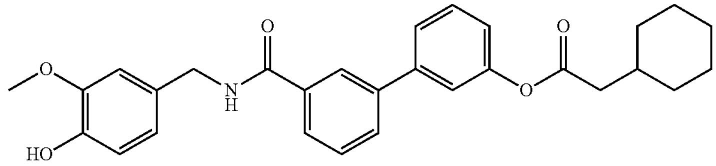 [SMILES: COc1cc(CNC(=O)c2cccc(-c3cccc(OC(=O)CC4CCCCC4)c3)c2)ccc1O] (400 MHz, $CD_3OD$) δ: 8.10 (1H, t, J = 2.2 Hz), 7.84 (1H, d, J = 8.0 Hz), 7.80 (1H, d, J = 8.0 Hz), 7.58-7.46 (3H, m), 7.85 (1H, t, J = 1.8 Hz), 7.11-7.07 (1H, m), 6.97 (1H, d, J = 2.0 Hz), 6.82 (1H, dd, J = 2.0, 8.0 Hz), 6,76 (1H, d, J = 7.6 Hz), 4.50 (2H, s), 3.84 (3H, s), 2.48 (2H, d, J = 7.6 Hz), 1.94-1.66 (6H, m), 1.40-1.21 (3H, m), 1.14-1.07 (2H, m). |

TABLE 2-continued

| Example No. | Structural formula and $^1$H-NMR |
|---|---|
| 46 | 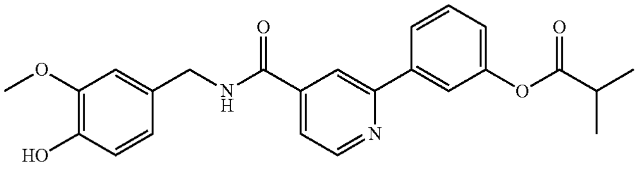 [SMILES: COc1cc(CNC(=O)c2ccnc(-c3cccc(OC(=O)C(C)C)c3)c2)ccc1O] (400 MHz, $CD_3OD$) δ: 8.57 (1H, d, J = 4.0 H), 8.24 (1H, s), 7.94 (1H, dd, J = 1.6, 8.0 Hz), 7.78 (1H, t, J = 1.8 Hz), 7.73 (1H, dd, J = 1.4, 5.0 Hz), 7.54 (1H, t, J = 7.8 Hz), 7.21-7.17 (1H, m), 6.98 (1H, d, J = 1.6 Hz), 6.83 1H, dd, J = 1.6, 8.0 Hz), 6.76 (1H, d, J = 8.0 Hz), 4.52 (2H, s), 3.85 (3H, s), 2.86 (1H, p, J = 6.8 Hz), 1.33 (6H, d, J = 6.4 Hz). |
| 47 | 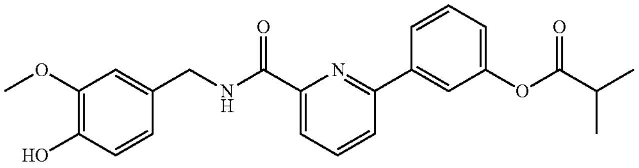 [SMILES: COc1cc(CNC(=O)c2cccc(-c3cccc(OC(=O)C(C)C)c3)n2)ccc1O] (400 MHz, $CD_3OD$) δ: 8.10-8.01 (4H, m), 7.91 (1H, t, J = 1.8 Hz), 7.53 (1H, t, J = 8.0 Hz), 7.16, (1H, dd, J = 2.8, 8.0 Hz), 7.00 (1H, d, J = 2.0 Hz), 8.85 (1H, dd, J = 2.2, 8.2 Hz), 6.76 (1H, d, J = 8.0 Hz), 4.57 (2H, s), 3.84 (3H, s), 2.86 (1H, p, J = 7.1 Hz), 1.32 (6H, d, J = 7.2 Hz). |
| 48 | 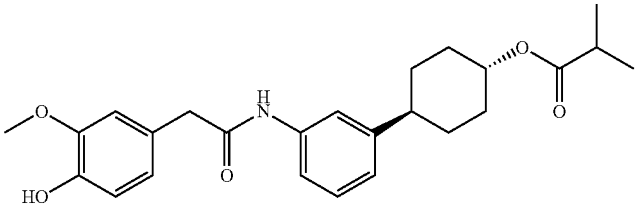 [SMILES: COc1cc(CC(=O)Nc2cccc([C@H]3CC[C@H](OC(=O)C(C)C)CC3)c2)ccc1O] (400 MHz, DMSO-$d_6$) δ: 9.67 (1H, s), 8.79 (1H, s), 7.50-7.46 (1H, m), 7.38 (1H, d, J = 7.6 Hz), 7.18 (1H, t, J = 7.8 Hz), 6.94-6.87 (2H, m), 6.69 (2H, s), 4.70-4.60 (1H, m), 3.74 (3H, s), 3.47 (2H, s), 2.00-1.91 (2H, m), 1.86-1.76 (2H, m), 1.58-1.39 (4H, m), 1.07 (6H, d, J = 7.2 Hz). |

Test Examples

In the following, the results of pharmacological tests of representative compounds of the present invention are shown and the pharmacological actions of such compounds are described; however, the present invention is not limited to these Test Examples.

Test Example 1: Evaluation of Agonistic Properties Using Human TRPV1 Transiently Expressing Cells (1) Generation of Human TRPV1 Transiently Expressing Cells Human TRPV1 transiently expressing cells were generated and subjected to culture. Specifically, HEK293 cells (cat #CCL-82.2, ATCC) were used as host cells. Human TRPV1 and apoaequorin were transiently expressed by introducing the mammalian cell expression pcDNA3.1 vector (cat #v790-20, Invitrogen) into which the TRPV1 gene (GenBank NP_542435.2) had been inserted.

The Dulbecco's Modified Eagle's Medium (DMEM) medium (cat #11550-043, Thermo Fisher Scientific) containing 10% inactivated fetal bovine serum (cat #10270-106, Thermo Fisher Scientific) was used as the medium, and the culture was carried out in tissue culture dishes (cat #3020-100, Iwaki). During the culture, cells were collected every 2 to 3 days by treating with PBS containing 10% 2.5 g/l-trypsin/1 mol/L EDTA solution, phenol red (cat #32777-44, Nacalai Tesque), and passage culture was carried out.

Three days after the passage, cells were collected with 10% trypsin-PBS treatment at a state of about 80% confluency, suspended in a DMEM medium containing 10% fetal bovine serum to 4000 cells/35 μl/well, and seeded into 384-well plates (cat #353962, FALCON).

The day after seeding, Viviren (cat #E6492, Promega) was added (15 μl/well) to a final concentration of 4.5 μM/HBSS (cat #14065-056, Thermo Fisher Scientific)/90 mM HEPES (cat #17514-15, Nacalai Tesque)/0.1% BSA (cat #01281-84, Nacalai Tesque), and after centrifugation, the samples were allowed to stand at room temperature for 2 hours under light-shielded conditions.

(2) Preparation of Test Compounds

For the test compounds, dimethyl sulfoxide solutions were produced at a concentration 1000 times the final concentration, and from these solutions, solutions at concentration 10 times the final concentration were prepared with Hanks/20 mmol/L HEPES/0.10% BSA (cat #01281-84, Nacalai Tesque).

(3) Evaluation of TRPV1-Agonistic Properties

FDSS7000 (Hamamatsu Photonics K.K.) was used for detection of TRPV1 agonist-stimulated luminescence signals. The test compounds were added to plates to which the cells and luminescent substrates had been added. The luminescence signals (center wavelength: 465 nm) after addition of the test compounds were measured, and the Rlu (Max-Min) was calculated. Data on TRPV1-agonistic activity of the representative compounds are shown in Tables 3 and 4.

TABLE 3

| Example | TRPV1 $EC_{50}$ (nM) | Example | TRPV1 $EC_{50}$ (nM) | Example | TRPV1 $EC_{50}$ (nM) |
|---|---|---|---|---|---|
| 1 | 2.6 | 2 | 4.5 | 3 | 340.7 |
| 4 | 33.6 | 5 | 61.2 | 6 | 5.3 |
| 7 | 5.6 | 8 | 6.1 | 9 | 2.0 |
| 10 | 4.8 | 11 | 21.3 | 12 | 6.3 |
| 13 | 9.0 | 14 | 6.3 | 15 | 4.6 |
| 16 | 6.3 | 17 | 2.6 | 18 | 5.4 |
| 19 | 2.7 | 20 | 35.1 | 21 | 6753.0 |
| 22 | 6.8 | 23 | 15.2 | 24 | 3.9 |
| 25 | 38.0 | 26 | 2.3 | 27 | 11.1 |
| 28 | 8.8 | 29 | 13.2 | 30 | 7.2 |
| 31 | 14.9 | 32 | 11.6 | 33 | 12.5 |
| 34 | 12.8 | 35 | 8.2 | 36 | 57.5 |
| 37 | 73.1 | 38 | 18.9 | 39 | 282.4 |
| 40 | 480.1 | 41 | 95.1 | 42 | 83.1 |
| 43 | 3079.0 | 44 | 10.2 | 45 | 31.3 |
| 46 | 4.3 | 47 | 148.3 | 48 | 32.1 |

TABLE 4

| Reference Example | TRPV1 $EC_{50}$ (nM) | Reference Example | TRPV1 $EC_{50}$ (nM) | Reference Example | TRPV1 $EC_{50}$ (nM) |
|---|---|---|---|---|---|
| 9 | 2688 | 10 | 8062 | 12 | 3292 |
| 13 | 606 | 14 | 1654 | 15 | 4562 |
| 16 | 1005 | 17 | 7017 | 18 | 6107 |
| 19 | 2720 | | | | |

As shown in the tables above, the compounds of the present invention had TRPV-1-agonistic activity in the evaluation test for TRPV-1-agonistic properties. In particular, Examples 1, 2, 9, 10, 15, 17, 19, 24, 26, and 46 exhibited a stronger TRPV-1-agonistic activity.

Test Example 2: Evaluation of Improving Effect of Swallowing in Rat Haloperidol-Induced Dysphagia Model This test is for evaluating the effect of improving dysphagia of drugs. Haloperidol causes a decrease in the swallowing reflex due to inhibition of dopamine D2 receptors and is therefore used not only as a model for dysphagia induced by drugs such as antipsychotics, but also as a model for dysphagia in the context of neurodegenerative diseases such as Parkinson's disease and as a model for other dysphagia in which the swallowing reflex is decreased. Haloperidol was administered to Crl:CD(SD) male rats (8 rats per group, 8 weeks old, body weight 280 to 310 g: at the time of arrival). Specifically, it was administered subcutaneously on the back using a polypropylene disposable syringe (Terumo Corporation) fitted with a 23 G injection needle (Terumo Corporation). The volume of fluid administered was calculated at 5 ml/kg based on the body weight closest to the day of administration, and the number of times of administration was twice a day (12±2 hours apart) for 7 days, 14 times in total, to generate models. The number of swallows was measured in the morning on the day after the 7th day of administration. The anesthetic was administered intraperitoneally to the animals using a polypropylene disposable syringe (Terumo Corporation) fitted with a 25 g injection needle (Terumo Corporation) [the volume of fluid administered: calculated at 2.3 ml/kg based on the body weight on that day. Ketamine (90 mg/kg) and xylazine (10 mg/kg) contained]. After the induction of anesthesia, the animals were sheared under the jaw with clippers and held in a supine position on a heat pad kept at 37° C. to prevent limb movement. A rat sonde was inserted once into the animals' mouths, and the tip of the sonde was retained in the pharynx. While maintaining this condition, 0.1 ml of the test substance administration solution was injected. After the injection, one swallowing movement induced by the swallowing reflex was measured as one swallowing. Two measurements were performed per case, and the average value of the first and second measurements was calculated. Note that the vehicle used was 0.01% ethanol. The results are shown in FIG. 1.

Test Example 3: Evaluation of Taste Aversion by Drinking Water

This test is for evaluating the taste aversion of drugs. The test was carried out by, while keeping Crl:CD(SD) rats (8 rats per group, 8 weeks old at the time of arrival) in home cages, adding the test substance solutions to water bottles. Two water bottles per cage were prepared, each filled with vehicle (sterile water containing 0.05% ethanol) and the test substance solution, and kept overnight, and the amount of water consumed during that period was measured. The proportion of water consumed with the test substance was calculated from the total amount of water consumed from the two water bottles, and the evaluation of taste aversion was carried out. It can be evaluated that the larger the proportion of water consumed with the test substance, the smaller the taste aversion and the smaller the stimulatory properties caused by the test substance. The results are shown in Table 5.

TABLE 5

| % Vehicle | Capsaicin | Example 12 | Example 2 | Example 26 | Example 1 |
|---|---|---|---|---|---|
| Vehicle | 100 | 100 | 100 | 100 | 100 |
| 0.3 μM | 71 | — | — | — | — |
| 1 μM | 13 | 103 | 94 | 113 | 90 |
| 3 μM | 9 | 31 | 80 | 86 | 66 |
| 10 μM | — | 22 | 71 | 55 | 35 |

Test Example 4: Evaluation Test for Metabolic Stability to S9

The compounds were added to a reaction solution in which the liver S9 fraction was diluted with phosphate buffer, and incubation was initiated at 37° C. (final compound concentration 10 nM, final volume 300 μL). After incubation for 15 minutes, the reaction was stopped by adding the reaction solution to acetonitrile, and centrifugation was carried out. After filtering the supernatant through a filter, the amount of compounds was determined using LC/MS/MS. From the amount of compounds obtained, the residual rate 15 minutes after the initiation of the reaction was calculated relative to the amount of compounds before the initiation of the reaction (0 minutes). The results are shown in Table 6.

TABLE 6

| Example | Residual rate (%) | Example | Residual rate (%) |
|---|---|---|---|
| 1 | <1 | 2 | 1 |
| 3 | <1 | 4 | <1 |
| 5 | 90 | 6 | 1 |
| 7 | 100 | 8 | 89 |

TABLE 6-continued

| Example | Residual rate (%) | Example | Residual rate (%) |
|---|---|---|---|
| 9 | 88 | 10 | 67 |
| 11 | 91 | 12 | 2 |
| 13 | 89 | 14 | 11 |
| 15 | 69 | 16 | <1 |
| 17 | <1 | 18 | <1 |
| 19 | <1 | 20 | <1 |
| 21 | <1 | 22 | <1 |
| 23 | <1 | 24 | <1 |
| 25 | <1 | 26 | <1 |
| 27 | <1 | 28 | <1 |
| 29 | <1 | 30 | <1 |
| 31 | <1 | 32 | 2 |
| 33 | <1 | 34 | <1 |
| 44 | <1 | 45 | <1 |
| 46 | <1 | 47 | <1 |

Test Example 5: Evaluation of Effect of Increasing Swallowing in Normal Rats This test is for evaluating the effect of increasing swallowing function of drugs. It has been reported that induction of the swallowing reflex in normal rats using NaCl-containing water suppresses the number of swallows, and the increase in swallowing function was evaluated using a NaCl-containing solvent. After the induction of anesthesia in Crl:CD(SD) male rats (7 to 8 rats per group, 8 to 9 weeks old, body weight 280 to 310 g: at the time of arrival), the animals were sheared under the jaw with clippers and held in a supine position on a heat pad kept at 37° C. to prevent limb movement. A rat sonde was inserted into the animals' mouths, and the tip of the sonde was retained in the pharynx. Under this condition, the test substance administration solution was administered at 12 ml/h for 10 seconds using an infusion pump, and the swallowing movements were measured for 30 seconds from the initiation of administration. Note that the vehicle used was saline solution containing 1% ethanol and 0.1% Tween 80. The results are shown in Table 7. The number of swallowings was significantly increased in capsaicin, Example 12, Example 2, and Example 49 compared to the solvent administered group (Dunnett's test: * indicates $P<0.05$,  indicates $P<0.01$, and * indicates $P<0.001$).

TABLE 7

| | Average | Standard error |
|---|---|---|
| Vehicle | 3.1 | 0.8 |
| Capsaicin | 14.1* | 2.7 |
| Example 12 | 19.4** | 2.7 |
| Example 2 | 17.8*** | 3.3 |
| Example 1 | 7.6 | 2.5 |
| Example 49 | 15.0* | 3.1 |

Test Example 6: Evaluation with Respect to Desensitization of Effect of Increasing Swallowing in Normal Rats TRPV1 agonists are known to induce TRPV1 desensitization when given at high doses or repeatedly. Using the same method as in Test Example 5, the effect of drugs on normal swallowing function in rats to induce desensitization was investigated. After the induction of anesthesia in Crl:CD(SD) male rats (7 to 8 rats per group, 8 to 9 weeks old, body weight 280 to 310 g: at the time of arrival), the animals were sheared under the jaw with clippers and held in a supine position on a heat pad kept at 37° C. to prevent limb movement. A sonde was inserted into the animals' mouths, and the tip of the sonde was retained in the pharynx. Under this condition, the test substance administration solution was administered at 12 ml/h for 10 seconds using an infusion pump, and the swallowing movements were measured for 30 seconds from the initiation of administration. Thereafter, the same test was performed about 5 minutes later, and the evaluation was repeated for a total of five times. Note that the vehicle used was saline solution containing 1% ethanol and 0.1% Tween 80. The results are shown in Table 8. For capsaicin, the number of swallows was significantly reduced at the 4th and 5th administrations compared to the 1st administration (Dunnett's test: ** indicates $P<0.01$). On the other hand, no significant difference was seen in Example 49.

TABLE 8

| | First time | Second time | Third time | Fourth time | Fifth time |
|---|---|---|---|---|---|
| Capsaicin (10 µM) | | | | | |
| Average | 18.2 | 13.2 | 14 | 9.7** | 9.5** |
| Standard error | 1.6 | 2.1 | 2.7 | 2.2 | 2.4 |
| Example 49 (10 µM) | | | | | |
| average | 12.3 | 12.4 | 12.9 | 11.3 | 14.4 |
| Standard error | 1.0 | 1.4 | 1.4 | 1.3 | 1.6 |
| Example 49 (30 µM) | | | | | |
| Average | 17.1 | 13.9 | 14.1 | 12.4 | 12.7 |
| Standard error | 1.1 | 2.0 | 2.4 | 2.6 | 2.1 |

Test Example 7: Evaluation with Respect to Test for Eye Stimulatory Properties in Normal Rats It has been reported that TRPV1 agonists have stimulatory properties and that administration of TRPV1 agonist solutions to the eye can induce wiping behavior. The stimulatory properties of the compounds were investigated using normal rats. Crl:CD(SD) male rats (5 rats per group, 8 weeks old, body weight 271 to 320 g) were held unanesthetized and 10 µL was dropped into the right eye using a micropipette. The animals were immediately returned to the observation cage and their wiping behavior was observed for 1 minute. The number of wiping behaviors is shown in Table 9. Capsaicin significantly increased the number of wiping behaviors at concentrations of 30 µM and more (Dunnett's test: * indicates $P<0.05$ and ** indicates $P<0.01$). On the other hand, no significant difference was seen in Example 12, Example 2, Example 1, and Example 49.

TABLE 9

| Group Concentration (μM) | Control | Capsaicin | Example 2 | Example 12 | Example 1 | Example 49 |
|---|---|---|---|---|---|---|
| | Number of eye-wiping (Average ± Standard deviation) | | | | | |
| 0 | 0.6 ± 0.5 | | | — | | |
| 1 | — | 2.0 ± 2.3 | 0.6 ± 0.9 | — | — | 0.0 ± 0.0 |
| 3 | | 0.2 ± 0.4 | 0.2 ± 0.4 | 0.0 ± 0.0 | 1.0 ± 1.0 | 0.0 ± 0.0 |
| 10 | | 6.4 ± 6.3* | 1.6 ± 2.2 | 1.0 ± 1.7 | 0.0 ± 0.0 | 0.2 ± 0.4 |
| 30 | | 6.4 ± 4.4** | 1.0 ± 1.4 | 1.0 ± 1.2 | 0.0 ± 0.0 | 0.6 ± 1.3 |
| 100 | | 21.4 ± 9.7** | 6.0 ± 5.0 | 1.4 ± 1.3 | 0.6 ± 1.3 | 2.0 ± 4.5 |
| 300 | | — | — | 1.6 ± 0.5 | 0.8 ± 1.1 | — |

As described above, the compound of the present invention is a potent TRPV1 agonist and demonstrates the effect of improving the swallowing reflex in the haloperidol-induced dysphagia animal model used as a dysphagia model. Since it improves the decreased swallowing reflex by antagonizing dopamine D2 receptors, it is useful as a therapeutic drug for drug-induced dysphagia due to administration of antipsychotics and other drugs, as well as for dysphagia due to neurodegenerative diseases such as Parkinson's disease, cerebrovascular diseases in which the swallowing reflex is decreased, and aging, for example.

INDUSTRIAL APPLICABILITY

Since the compound of the present disclosure exhibits TRPV1-agonistic properties, it is useful as a therapeutic drug for dysphagia induced by agents, dysphagia in the context of neurodegenerative diseases such as Parkinson's disease, and dysphagia in which the swallowing reflex is decreased due to various causes such as cerebrovascular diseases and aging.

The invention claimed is:

1. A compound or pharmaceutically acceptable salt thereof, having a structure:

3-{6-[2-(4-hydroxy-3-methoxyphenyl)acetamido]pyridin-2-yl}phenyl 2-methylpropanoate;

cis-4-{3-[2-(4-hydroxy-3-methoxyphenyl)acetamido) phenyl}cyclohexyl cyclohexanecarboxylate;

cis-4-{3-[2-(4-hydroxy-3-methoxyphenyl)acetamido] phenyl}cyclohexyl (3-methylphenyl)acetate;

cis-4-{3-[2-(4-hydroxy-3-methoxyphenyl)acetamido] phenyl}cyclohexyl (2-chlorophenyl)acetate;

cis-4-{3-[2-(4-hydroxy-3-methoxyphenyl)acetamido] phenyl}cyclohexyl acetate;

cis-4-{3-[2-(4-hydroxy-3-methoxyphenyl)acetamido] phenyl}cyclohexyl (2-fluorophenyl)acetate;

cis-4-{3-[2-(4-hydroxy-3-methoxyphenyl)acetamido] phenyl}cyclohexyl (2-methylpropanoate;

2'-fluoro-5'-[2-(4-hydroxy-3'-methoxyphenyl)acetamido] [1,1'-biphenyl-3-yl 2-methylpropanoate;

3'-[2-(4-hydroxy-3-methoxyphenyl)acetamido][1,1'-biphenyl]-3-yl 2-methylpropanoate;

3'-{4-[2-(4-hydroxy-3-methoxyphenyl)acetamido]pyridin-2-yl}phenyl 2-methylpropanoate;

3-(4-{[(4-hydroxy-3-methoxyphenyl)methyl] carbamoyl}pyridin-2-yl)phenyl 2-methylpropanoate; or 3-{4-2-4-hydroxy-3-methoxyphenyl)acetamido]pyridin-2-yl}phenyl 2-methylpropanoate hydrochloride.

2. A pharmaceutical composition, comprising:

the compound or pharmaceutically acceptable salt thereof according to claim 1.

3. A method for treating or preventing a disorder or disease in which TRPV1 is involved, the method comprising:

administering to a patient in need thereof a therapeutically or prophylactically effective amount of the compound or pharmaceutically acceptable salt thereof according to claim 1.

4. A pharmaceutical composition, comprising:

the compound or pharmaceutically acceptable salt thereof according to claim 1; and at least one agent.

5. A method for treating or preventing a disorder or disease in which TRPV1 is involved, the method comprising:

administering to a patient in need thereof a therapeutically or prophylactically effective amount of the compound or pharmaceutically acceptable salt thereof according to claim 1 and at least one agent.

6. A method for treating or preventing dysphagia, comprising:

administering to a patient in need thereof a therapeutically or prophylactically effective amount of the compound or pharmaceutically acceptable salt thereof according to claim 1 and at least one agent.

7. The compound or pharmaceutically acceptable salt of claim 1, having a structure:

3-{6-[2-(4-hydroxy-3-methoxyphenyl)acetamido]pyridin-2-yl}phenyl 2-methylpropanoate.

8. The compound or pharmaceutically acceptable salt of claim 1, having a structure:

cis-4-{3-[2-(4-hydroxy-3-methoxyphenyl)acetamido] phenyl}cyclohexyl cyclohexanecarboxylate.

9. The compound or pharmaceutically acceptable salt of claim 1, having a structure:

cis-4-{3-[2-(4-hydroxy-3-methoxyphenyl)acetamido] phenyl}cyclohexyl (3-methylphenyl)acetate.

10. The compound or pharmaceutically acceptable salt of claim 1, having a structure:

cis-4-{3-[2-(4-hydroxy-3-methoxyphenyl)acetamido] phenyl}cyclohexyl (2-chlorophenyl)acetate.

11. The compound or pharmaceutically acceptable salt of claim 1, having a structure:

cis-4-{3-[2-(4-hydroxy-3-methoxyphenyl)acetamido] phenyl}cyclohexyl acetate.

12. The compound or pharmaceutically acceptable salt of claim 1, having a structure:

cis-4-{3-[2-(4-hydroxy-3-methoxyphenyl)acetamido] phenyl}cyclohexyl (2-fluorophenyl)acetate.

13. The compound or pharmaceutically acceptable salt of claim 1, having a structure:

cis-4-{3-[2-(4-hydroxy-3-methoxyphenyl)acetamido] phenyl}cyclohexyl 2-methylpropanoate.

14. The compound or pharmaceutically acceptable salt of claim 1, having a structure:

2'-fluoro-5'-[2-(4-hydroxy-3-methoxyphenyl)acetamido][1,1'-biphenyl]-3-yl 2-methylpropanoate.

15. The compound or pharmaceutically acceptable salt of claim 1, having a structure:

3'-[2-(4-hydroxy-3-methoxyphenyl)acetamido][1,1'-biphenyl]-3-yl 2-methylpropanoate.

16. The compound or pharmaceutically acceptable salt of claim 1, having a structure:

3-{4-[2-(4-hydroxy-3-methoxyphenyl)acetamido]pyridin-2-yl}phenyl 2-methylpropanoate.

17. The compound or pharmaceutically acceptable salt of claim 1, having a structure:

3-(4-{[(4-hydroxy-3-methoxyphenyl)methyl]carbamoyl}pyridin-2-yl)phenyl 2-methylpropanoate.

18. The compound or pharmaceutically acceptable salt of claim 1, having a structure:

3-{4-[2-(4-hydroxy-3-methoxyphenyl)acetamido]pyridin-2-yl}phenyl 2-methylpropanoate hydrochloride.

19. A method for treating or preventing a disorder or disease in which TRPV1 is involved, the method comprising:

administering to a patient in need thereof a therapeutically or prophylactically effective amount of the compound or pharmaceutically acceptable salt thereof according to claim 7.

20. A method for treating or preventing a disorder or disease in which TRPV1 is involved, the method comprising:

administering to a patient in need thereof a therapeutically or prophylactically effective amount of the compound or pharmaceutically acceptable salt thereof according to claim 8.

21. A method for treating or preventing a disorder or disease in which TRPV1 is involved, the method comprising:

administering to a patient in need thereof a therapeutically or prophylactically effective amount of the compound or pharmaceutically acceptable salt thereof according to claim 9.

22. A method for treating or preventing a disorder or disease in which TRPV1 is involved, the method comprising:

administering to a patient in need thereof a therapeutically or prophylactically effective amount of the compound or pharmaceutically acceptable salt thereof according to claim 10.

23. A method for treating or preventing a disorder or disease in which TRPV1 is involved, the method comprising:

administering to a patient in need thereof a therapeutically or prophylactically effective amount of the compound or pharmaceutically acceptable salt thereof according to claim 11.

24. A method for treating or preventing a disorder or disease in which TRPV1 is involved, the method comprising:

administering to a patient in need thereof a therapeutically or prophylactically effective amount of the compound or pharmaceutically acceptable salt thereof according to claim 12.

25. A method for treating or preventing a disorder or disease in which TRPV1 is involved, the method comprising:

administering to a patient in need thereof a therapeutically or prophylactically effective amount of the compound or pharmaceutically acceptable salt thereof according to claim 13.

26. A method for treating or preventing a disorder or disease in which TRPV1 is involved, the method comprising:

administering to a patient in need thereof a therapeutically or prophylactically effective amount of the compound or pharmaceutically acceptable salt thereof according to claim 14.

27. A method for treating or preventing a disorder or disease in which TRPV1 is involved, the method comprising:

administering to a patient in need thereof a therapeutically or prophylactically effective amount of the compound or pharmaceutically acceptable salt thereof according to claim 15.

* * * * *